United States Patent
Bewick-Sonntag et al.

(10) Patent No.: US 12,310,825 B2
(45) Date of Patent: *May 27, 2025

(54) ABSORBENT ARTICLE WITH CONFORMING FEATURES

(71) Applicant: The Procter & Gamble Company, Cincinnati, OH (US)

(72) Inventors: Christopher Philip Bewick-Sonntag, Cincinnati, OH (US); Shirdish Poondru, Cincinnati, OH (US); John Lee Hammons, Hamilton, OH (US); Kelyn Anne Arora, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/497,104

(22) Filed: Oct. 30, 2023

(65) Prior Publication Data
US 2024/0099900 A1    Mar. 28, 2024

Related U.S. Application Data

(63) Continuation of application No. 16/181,640, filed on Nov. 6, 2018, now Pat. No. 11,857,397.
(Continued)

(51) Int. Cl.
*A61F 13/15*    (2006.01)
*A61F 13/472*   (2006.01)
(Continued)

(52) U.S. Cl.
CPC .. *A61F 13/15699* (2013.01); *A61F 13/15203* (2013.01); *A61F 13/15707* (2013.01);
(Continued)

(58) Field of Classification Search
CPC .......... A61F 13/15699; A61F 13/15203; A61F 13/15707; A61F 13/15723;
(Continued)

(56) References Cited

U.S. PATENT DOCUMENTS

| | | | |
|---|---|---|---|
| 3,815,601 A | 6/1974 | Schaefer | |
| 3,884,000 A | 5/1975 | Faleij | |

(Continued)

FOREIGN PATENT DOCUMENTS

| | | |
|---|---|---|
| CA | 2250138 A1 | 3/1997 |
| CN | 1343484 A | 4/2002 |

(Continued)

OTHER PUBLICATIONS

All Office Actions; U.S. Appl. No. 16/181,621, filed Nov. 6, 2018.
(Continued)

*Primary Examiner* — Jacqueline F Stephens
(74) *Attorney, Agent, or Firm* — Sarah M. DeCristofaro

(57) ABSTRACT

A disposable absorbent article is described herein. The disposable absorbent article includes a topsheet, a backsheet, and an absorbent system disposed between the topsheet and the backsheet. At least a portion of the has a plurality of conforming features such that the absorbent article has a blot residual value of less than 30 mg and a bending stiffness of less than 12.

20 Claims, 52 Drawing Sheets

Related U.S. Application Data

(60) Provisional application No. 62/581,813, filed on Nov. 6, 2017.

(51) Int. Cl.

| | | |
|---|---|---|
| *A61F 13/49* | (2006.01) | |
| *A61F 13/511* | (2006.01) | |
| *A61F 13/512* | (2006.01) | |
| *A61F 13/53* | (2006.01) | |
| *A61F 13/536* | (2006.01) | |
| *A61F 13/537* | (2006.01) | |
| *B32B 5/02* | (2006.01) | |
| *B32B 37/20* | (2006.01) | |
| *B32B 38/00* | (2006.01) | |
| *B32B 38/06* | (2006.01) | |
| *D04H 1/00* | (2006.01) | |
| *D04H 1/04* | (2012.01) | |
| *D04H 1/425* | (2012.01) | |
| *D04H 1/732* | (2012.01) | |
| *D04H 3/015* | (2012.01) | |
| *D04H 11/00* | (2006.01) | |
| *A61F 13/51* | (2006.01) | |

(52) U.S. Cl.
CPC .. *A61F 13/15723* (2013.01); *A61F 13/15731* (2013.01); *A61F 13/15804* (2013.01); *A61F 13/472* (2013.01); *A61F 13/49011* (2013.01); *A61F 13/51108* (2013.01); *A61F 13/5116* (2013.01); *A61F 13/5121* (2013.01); *A61F 13/53* (2013.01); *A61F 13/536* (2013.01); *A61F 13/537* (2013.01); *A61F 13/53747* (2013.01); *B32B 5/022* (2013.01); *B32B 37/20* (2013.01); *B32B 38/0004* (2013.01); *B32B 38/06* (2013.01); *D04H 1/00* (2013.01); *D04H 1/04* (2013.01); *D04H 1/425* (2013.01); *D04H 1/732* (2013.01); *D04H 3/015* (2013.01); *D04H 11/00* (2013.01); *A61F 2013/15406* (2013.01); *A61F 2013/15715* (2013.01); *A61F 2013/49093* (2013.01); *A61F 2013/51019* (2013.01); *A61F 2013/51026* (2013.01); *A61F 2013/51028* (2013.01); *A61F 2013/5103* (2013.01); *A61F 2013/530233* (2013.01); *A61F 2013/53024* (2013.01); *A61F 2013/530343* (2013.01); *A61F 2013/530481* (2013.01); *B32B 2555/02* (2013.01); *D10B 2401/021* (2013.01); *D10B 2509/026* (2013.01)

(58) Field of Classification Search
CPC .......... A61F 13/15731; A61F 13/15804; A61F 13/472; A61F 13/4901; A61F 13/51108; A61F 13/5116; A61F 13/5121; A61F 13/53; A61F 13/536; A61F 13/537; A61F 13/53747; A61F 2013/15406; A61F 2013/15715; A61F 2013/49093; A61F 2013/51019; A61F 2013/51026; A61F 2013/5128; A61F 2013/5103; A61F 2013/530233; A61F 2013/53024; A61F 2013/530343; A61F 2013/530481; A61F 13/531; B32B 5/022; B32B 37/20; B32B 38/004; B32B 38/06; B32B 2555/02; D04H 1/00; D04H 1/04; D04H 1/425; D04H 1/732; D04H 3/015; D04H 11/00
See application file for complete search history.

(56) References Cited

U.S. PATENT DOCUMENTS

| | | |
|---|---|---|
| 3,908,645 A | 9/1975 | Sandvig |
| 3,929,135 A | 12/1975 | Thompson |
| 3,982,374 A | 9/1976 | Schaefer |
| 3,994,298 A | 11/1976 | Des |
| 4,026,292 A | 5/1977 | Hutchins |
| 4,055,184 A | 10/1977 | Karami |
| 4,061,145 A | 12/1977 | Desmarais |
| 4,151,240 A | 4/1979 | Lucas et al. |
| 4,319,868 A | 3/1982 | Riemersma et al. |
| 4,321,924 A | 3/1982 | Ahr |
| 4,324,426 A | 4/1982 | Michelson |
| 4,343,314 A | 8/1982 | Sramek |
| 4,425,130 A | 1/1984 | DesMarais |
| 4,589,876 A | 5/1986 | Van Tilburg |
| 4,591,523 A | 5/1986 | Thompson |
| 4,606,958 A | 8/1986 | Haq |
| 4,609,518 A | 9/1986 | Curro et al. |
| 4,629,643 A | 12/1986 | Curro et al. |
| 4,664,662 A | 5/1987 | Webster |
| 4,695,422 A | 9/1987 | Curro et al. |
| 4,758,466 A | 7/1988 | Dabi |
| 4,865,596 A | 9/1989 | Weisman |
| 4,950,264 A | 8/1990 | Osborn, III |
| 5,149,720 A | 9/1992 | DesMarais et al. |
| 5,221,726 A | 6/1993 | Dabi |
| 5,260,345 A | 11/1993 | Desmarais |
| 5,287,707 A | 2/1994 | Kitayama |
| 5,328,935 A | 7/1994 | Van Phan |
| 5,331,015 A | 7/1994 | Desmarais |
| 5,338,766 A | 8/1994 | Phan |
| 5,387,207 A | 2/1995 | Dyer |
| 5,397,316 A | 3/1995 | Young |
| 5,439,458 A | 8/1995 | Noel |
| 5,458,835 A | 10/1995 | Wilkes et al. |
| 5,500,451 A | 3/1996 | Goldman et al. |
| 5,518,801 A | 5/1996 | Chappell et al. |
| 5,536,264 A | 7/1996 | Hsueh |
| 5,560,878 A | 10/1996 | Dragoo |
| 5,607,414 A | 3/1997 | Richards |
| 5,628,097 A | 5/1997 | Benson et al. |
| 5,634,914 A | 6/1997 | Wilkes et al. |
| 5,713,881 A | 2/1998 | Rezai |
| 5,722,482 A | 3/1998 | Buckley |
| 5,817,704 A | 10/1998 | Shiveley |
| 5,827,909 A | 10/1998 | DesMarais |
| 5,868,724 A | 2/1999 | Dierckes, Jr. |
| 5,869,171 A | 2/1999 | Shiveley |
| 5,948,829 A | 9/1999 | Wallajapet |
| 5,989,478 A | 11/1999 | Ouellette et al. |
| 6,083,211 A | 7/2000 | Desmarais |
| 6,107,538 A | 8/2000 | Young |
| 6,160,028 A | 12/2000 | Dyer |
| 6,174,929 B1 | 1/2001 | Haehnle |
| 6,183,587 B1 | 2/2001 | Mcfall |
| 6,186,992 B1 | 2/2001 | Roe et al. |
| 6,203,654 B1 | 3/2001 | Mcfall |
| 6,261,679 B1 | 7/2001 | Chen |
| 6,277,104 B1 | 8/2001 | Lasko |
| 6,316,688 B1 | 11/2001 | Hammons |
| 6,333,108 B1 | 12/2001 | Wilkes et al. |
| 6,369,121 B1 | 4/2002 | Catalfamo et al. |
| 6,372,953 B1 | 4/2002 | Young |
| 6,399,854 B1 | 6/2002 | Vartiainen |
| 6,410,820 B1 | 6/2002 | Mcfall |
| 6,426,445 B1 | 7/2002 | Young |
| 6,455,600 B1 | 9/2002 | Haehnle |
| 6,475,199 B1 | 11/2002 | Gann |
| 6,486,379 B1 | 11/2002 | Chen |
| 6,525,106 B1 | 2/2003 | Desmarais |
| 6,551,295 B1 | 4/2003 | Schmidt |
| 6,582,411 B1 | 6/2003 | Carstens |
| 6,590,136 B1 | 7/2003 | Young |
| 6,603,054 B2 | 8/2003 | Chen |
| 6,642,430 B1 | 11/2003 | Busam |
| 6,657,101 B1 | 12/2003 | Malmgren et al. |

(56) References Cited

U.S. PATENT DOCUMENTS

| | | |
|---|---|---|
| 6,664,439 B1 | 12/2003 | Arndt |
| 6,673,057 B1 | 1/2004 | Ehrnsperger |
| 6,673,981 B1 | 1/2004 | Stroembom |
| 6,706,775 B2 | 3/2004 | Hermann |
| 6,713,661 B1 | 3/2004 | Arndt |
| 6,720,471 B1 | 4/2004 | Arndt |
| 6,746,436 B1* | 6/2004 | Sierri ............ A61F 13/47272 604/385.04 |
| 6,800,666 B2 | 10/2004 | Haehnle |
| 6,811,842 B1 | 11/2004 | Ehrnsperger |
| 6,943,200 B1 | 9/2005 | Corrand |
| 7,056,404 B2 | 6/2006 | Mcfall |
| 7,172,801 B2 | 2/2007 | Hoying et al. |
| 7,198,742 B2 | 4/2007 | Gerndt |
| 7,235,708 B2 | 6/2007 | Guidotti |
| 7,285,576 B2 | 10/2007 | Hyde |
| 7,410,683 B2 | 8/2008 | Curro et al. |
| 7,462,756 B2 | 12/2008 | Malowaniec |
| 7,507,459 B2 | 3/2009 | Turner et al. |
| 7,553,532 B2 | 6/2009 | Turner et al. |
| 7,625,363 B2 | 12/2009 | Yoshimasa et al. |
| 7,648,752 B2 | 1/2010 | Hoying et al. |
| 7,682,686 B2 | 3/2010 | Curro et al. |
| 7,718,243 B2 | 5/2010 | Curro et al. |
| 7,732,657 B2 | 6/2010 | Hammons et al. |
| 7,754,050 B2 | 7/2010 | Redd et al. |
| 7,789,049 B2 | 9/2010 | Duley |
| 7,789,994 B2 | 9/2010 | Hupp et al. |
| 7,838,099 B2 | 11/2010 | Curro et al. |
| 7,850,672 B2 | 12/2010 | Guidotti |
| 7,935,207 B2 | 5/2011 | Zhao et al. |
| 7,967,801 B2 | 6/2011 | Hammons et al. |
| 8,124,827 B2 | 2/2012 | Tamburro et al. |
| 8,153,226 B2 | 4/2012 | Curro et al. |
| 8,207,393 B2 | 6/2012 | Bach |
| 8,262,633 B2 | 9/2012 | Larson et al. |
| 8,426,670 B2 | 4/2013 | Nagasuna |
| 8,569,572 B2 | 10/2013 | Hammons |
| 8,674,169 B2 | 3/2014 | Brennan et al. |
| 8,707,717 B2 | 4/2014 | Fox |
| 8,708,723 B2 | 4/2014 | Stoltz |
| 8,728,049 B2 | 5/2014 | Hammons et al. |
| 8,769,058 B1 | 7/2014 | Barker, Jr. et al. |
| 8,906,404 B2 | 12/2014 | Wellings |
| 9,156,229 B2 | 10/2015 | Noda et al. |
| 9,408,761 B2 | 8/2016 | Xu et al. |
| 9,566,196 B2 | 2/2017 | Carlucci |
| 9,974,434 B2 | 5/2018 | Onda |
| 9,993,836 B2 | 6/2018 | McNeil et al. |
| 10,016,779 B2 | 7/2018 | McNeil et al. |
| 10,045,888 B2 | 8/2018 | Strube et al. |
| 11,857,397 B2* | 1/2024 | Bewick-Sonntag ........................ A61F 13/472 |
| 11,890,171 B2 | 2/2024 | Bewick-sonntag |
| 2001/0024716 A1 | 9/2001 | Chen |
| 2001/0041876 A1 | 11/2001 | Creagan |
| 2001/0047456 A1 | 11/2001 | Schrobenhausen |
| 2002/0026169 A1 | 2/2002 | Takai |
| 2003/0181884 A1 | 9/2003 | Carstens |
| 2003/0187417 A1 | 10/2003 | Kudo et al. |
| 2003/0191204 A1 | 10/2003 | Hermann |
| 2003/0220039 A1 | 11/2003 | Chen |
| 2004/0015145 A1 | 1/2004 | Miura |
| 2004/0193129 A1 | 9/2004 | Guidotti |
| 2004/0229008 A1 | 11/2004 | Hoying |
| 2004/0254551 A1 | 12/2004 | Carnes |
| 2004/0254554 A1 | 12/2004 | Mavinkurve et al. |
| 2005/0087292 A1 | 4/2005 | Mcfall |
| 2005/0136224 A1 | 6/2005 | Nickel |
| 2005/0250866 A1 | 11/2005 | Champ |
| 2008/0021426 A1 | 1/2008 | Nakagawa et al. |
| 2008/0217809 A1 | 9/2008 | Zhao |
| 2009/0030390 A1 | 1/2009 | Hammons |
| 2009/0270827 A1 | 10/2009 | Gundersen |
| 2010/0035014 A1 | 2/2010 | Hammons et al. |
| 2010/0036338 A1 | 2/2010 | Hammons |
| 2010/0036339 A1 | 2/2010 | Hammons |
| 2010/0162888 A1 | 7/2010 | Bluecher |
| 2010/0222759 A1 | 9/2010 | Hammons et al. |
| 2010/0228209 A1 | 9/2010 | Carlucci et al. |
| 2010/0262104 A1 | 10/2010 | Carlucci et al. |
| 2011/0174430 A1 | 7/2011 | Zhao et al. |
| 2011/0196330 A1* | 8/2011 | Hammons ............ A61F 13/512 604/383 |
| 2012/0001122 A1 | 1/2012 | Wattebled |
| 2012/0101460 A1 | 4/2012 | Ehmke et al. |
| 2012/0103504 A1 | 5/2012 | Deng |
| 2012/0108692 A1 | 5/2012 | Dyer |
| 2012/0157952 A1 | 6/2012 | Poruthoor et al. |
| 2012/0237606 A1 | 9/2012 | Wellings |
| 2013/0079741 A1 | 3/2013 | Nakashita |
| 2013/0178815 A1 | 7/2013 | Ohashi et al. |
| 2014/0050886 A1 | 2/2014 | Burgin |
| 2014/0127460 A1 | 5/2014 | Xu |
| 2014/0163503 A1 | 6/2014 | Arizti |
| 2014/0276518 A1 | 9/2014 | Varona |
| 2014/0295134 A1 | 10/2014 | Wood |
| 2014/0295135 A1 | 10/2014 | Thompson, Jr. |
| 2014/0366293 A1 | 12/2014 | Roe et al. |
| 2015/0017970 A1 | 1/2015 | Takiguchi |
| 2015/0057630 A1 | 2/2015 | Tange et al. |
| 2015/0119837 A1 | 4/2015 | Thompson, Jr. |
| 2015/0173970 A1 | 6/2015 | Gross et al. |
| 2015/0179750 A1 | 6/2015 | Calafut |
| 2015/0238370 A1 | 8/2015 | Uda et al. |
| 2015/0297781 A1 | 10/2015 | Uda et al. |
| 2015/0313770 A1 | 11/2015 | Hubbard, Jr. et al. |
| 2015/0335498 A1 | 11/2015 | Hubbard, Jr. et al. |
| 2015/0342798 A1 | 12/2015 | Jackels |
| 2015/0366726 A1 | 12/2015 | Noda |
| 2015/0374560 A1 | 12/2015 | Hubbard, Jr. |
| 2015/0374561 A1 | 12/2015 | Hubbard, Jr. et al. |
| 2016/0074252 A1 | 3/2016 | Strube et al. |
| 2016/0075123 A1 | 3/2016 | Strube et al. |
| 2016/0089279 A1 | 3/2016 | Barbosa et al. |
| 2016/0160900 A1 | 6/2016 | Milanowski |
| 2016/0287452 A1 | 10/2016 | Hubbard, Jr. et al. |
| 2016/0346805 A1 | 12/2016 | McNeil et al. |
| 2017/0000654 A1 | 1/2017 | Wirtz et al. |
| 2017/0071795 A1 | 3/2017 | Bewick-Sonntag et al. |
| 2017/0119587 A1 | 5/2017 | Bewick-sonntag |
| 2017/0119588 A1 | 5/2017 | Bewick-sonntag |
| 2017/0119589 A1 | 5/2017 | Bewick-sonntag |
| 2017/0119593 A1 | 5/2017 | Hubbard, Jr. |
| 2017/0119594 A1 | 5/2017 | Bewick-sonntag |
| 2017/0119595 A1 | 5/2017 | Carla |
| 2017/0119596 A1 | 5/2017 | Bewick-sonntag |
| 2017/0119597 A1 | 5/2017 | Bewick-sonntag |
| 2017/0119598 A1 | 5/2017 | Bewick-sonntag |
| 2017/0128283 A1 | 5/2017 | Uda |
| 2017/0191198 A1 | 7/2017 | Ashraf |
| 2017/0267827 A1 | 9/2017 | Rowan et al. |
| 2017/0319401 A1 | 11/2017 | Ludher |
| 2017/0319402 A1 | 11/2017 | Morrow |
| 2017/0319403 A1 | 11/2017 | Bewick-sonntag |
| 2017/0319404 A1 | 11/2017 | Bewick-sonntag |
| 2017/0360618 A1 | 12/2017 | Mullane |
| 2018/0110600 A1 | 4/2018 | Wotherspoon et al. |
| 2018/0110660 A1 | 4/2018 | Bewick-sonntag |
| 2018/0168884 A1 | 6/2018 | Hubbard, Jr. et al. |
| 2018/0169832 A1 | 6/2018 | Viens et al. |
| 2018/0228656 A1 | 8/2018 | Schneider et al. |
| 2018/0228666 A1 | 8/2018 | Trinkaus et al. |
| 2018/0228667 A1 | 8/2018 | Schneider et al. |
| 2018/0228668 A1 | 8/2018 | Schneider et al. |
| 2018/0228669 A1 | 8/2018 | Schneider et al. |
| 2018/0271720 A1 | 9/2018 | Tange |
| 2018/0318151 A1 | 11/2018 | Bewick-sonntag |

(56) References Cited

U.S. PATENT DOCUMENTS

| | | | |
|---|---|---|---|
| 2019/0133843 A1 | 5/2019 | Bewick-sonntag et al. | |
| 2024/0091070 A1 | 3/2024 | Bewick-sonntag | |

FOREIGN PATENT DOCUMENTS

| | | | |
|---|---|---|---|
| CN | 1720362 | A | 1/2006 |
| CN | 101208466 | A | 6/2008 |
| CN | 101473081 | A | 7/2009 |
| CN | 104068971 | A | 10/2014 |
| CN | 105517518 | A | 4/2016 |
| CN | 106137546 | A | 11/2016 |
| CN | 106999308 | A | 8/2017 |
| EP | 0278476 | A2 | 8/1988 |
| EP | 0397110 | A2 | 11/1990 |
| EP | 0794751 | B1 | 11/1995 |
| EP | 1358894 | A1 | 11/2003 |
| EP | 1061966 | B1 | 10/2004 |
| EP | 1139951 | B1 | 10/2004 |
| EP | 2532328 | A1 | 12/2012 |
| EP | 1605881 | B1 | 4/2013 |
| EP | 2740451 | A1 | 6/2014 |
| GB | 1570485 | A | 7/1980 |
| GB | 2326828 | A | 1/1999 |
| JP | 2003291234 | A | 10/2003 |
| JP | 2004000465 | A | 1/2004 |
| JP | 2010104545 | A | 5/2010 |
| JP | 2010104546 | A | 5/2010 |
| JP | 4989960 | B2 | 8/2012 |
| JP | 2015047432 | A | 3/2015 |
| JP | 2015198798 | A | 11/2015 |
| JP | 2016112156 | A | 6/2016 |
| JP | 6029715 | B1 | 11/2016 |
| JP | 2017012439 | A | 1/2017 |
| WO | 9500090 | A1 | 1/1995 |
| WO | 9611714 | A1 | 4/1996 |
| WO | 9945878 | A1 | 9/1999 |
| WO | 9947184 | A1 | 9/1999 |
| WO | 9955269 | A1 | 11/1999 |
| WO | 0000136 | A1 | 1/2000 |
| WO | 0000138 | A1 | 1/2000 |
| WO | 0039201 | A2 | 7/2000 |
| WO | 0059438 | A1 | 10/2000 |
| WO | 0078369 | A1 | 12/2000 |
| WO | 0124754 | A1 | 4/2001 |
| WO | 0168022 | A1 | 9/2001 |
| WO | 03026707 | A2 | 4/2003 |
| WO | 2004084784 | A1 | 10/2004 |
| WO | 2004084785 | A1 | 10/2004 |
| WO | 2006009995 | A1 | 1/2006 |
| WO | 2012009590 | A1 | 1/2012 |
| WO | 2014083934 | A1 | 6/2014 |
| WO | 2015053057 | A1 | 4/2015 |
| WO | 2016002289 | A1 | 1/2016 |
| WO | 2016031568 | A1 | 3/2016 |
| WO | 2016031569 | A1 | 3/2016 |
| WO | 2016103959 | A1 | 6/2016 |
| WO | 2016103961 | A1 | 6/2016 |
| WO | 2016103967 | A1 | 6/2016 |
| WO | 2017002486 | A1 | 1/2017 |
| WO | 2017187669 | A1 | 11/2017 |

OTHER PUBLICATIONS

All Office Actions; U.S. Appl. No. 18/500,597, filed Nov. 2, 2023.
Search Report and Written Opinion for PCT/US2018/059348, dated Feb. 13, 2019; 12 pages.
All Office Actions; U.S. Appl. No. 16/181,640, filed Nov. 6, 2018.

* cited by examiner

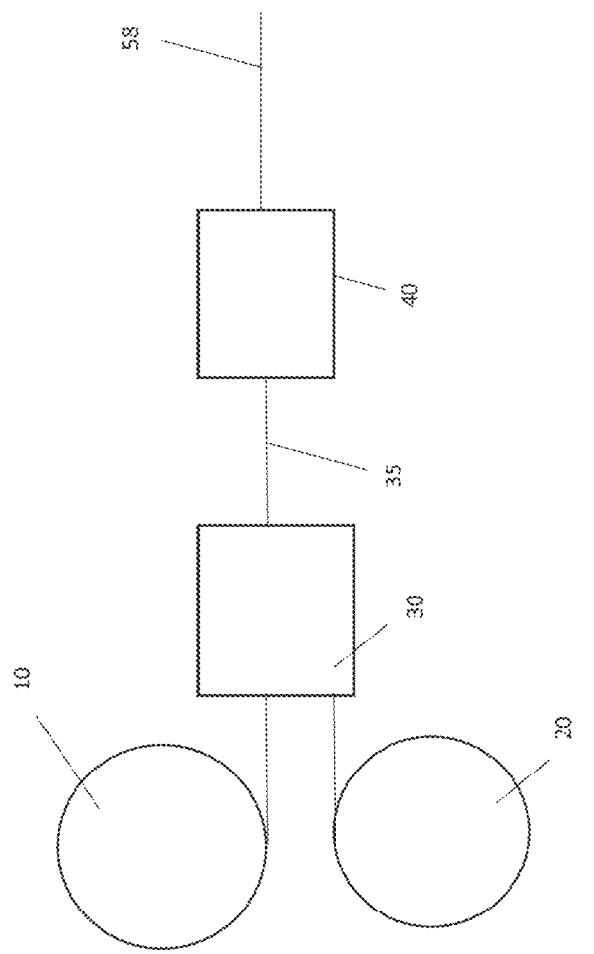

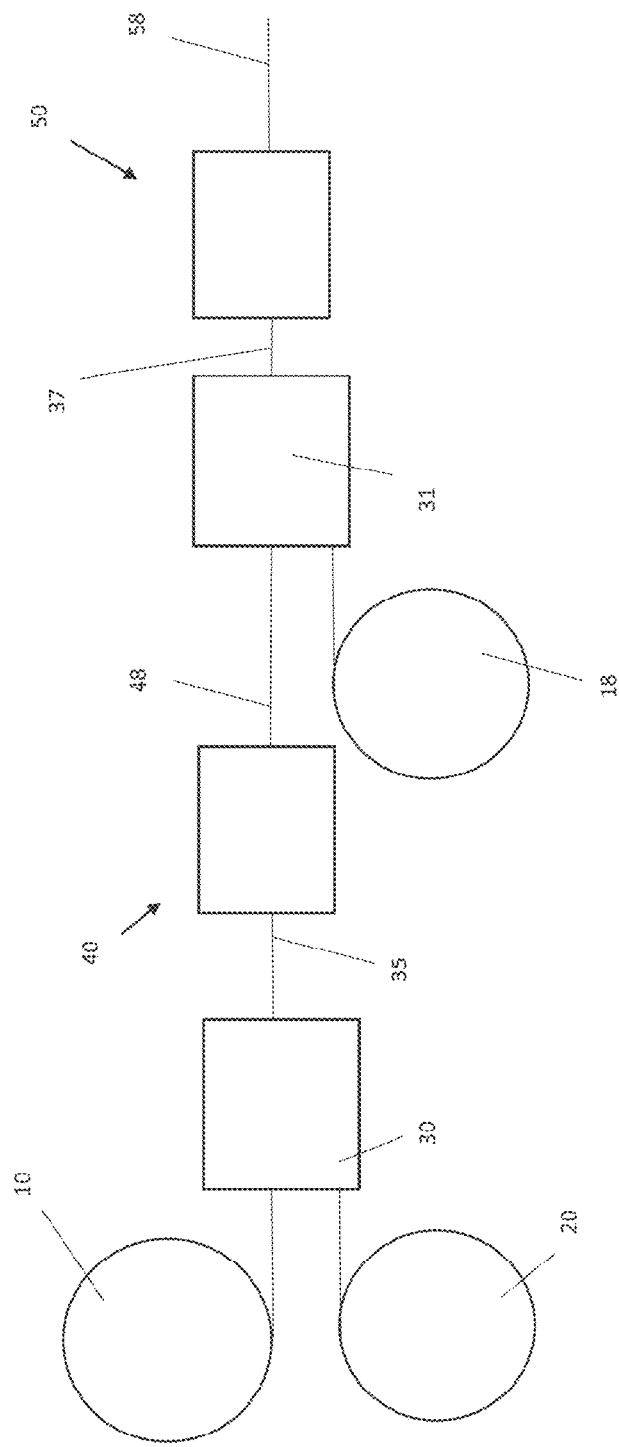

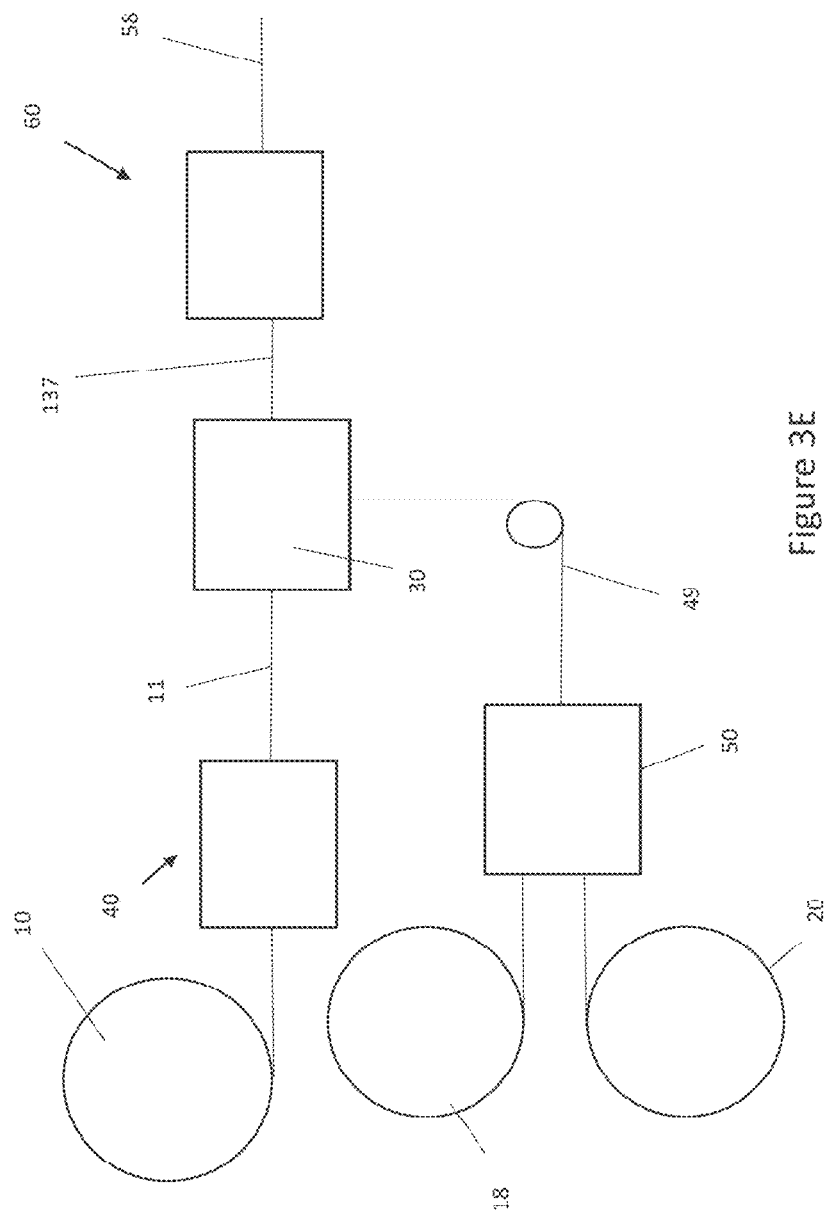

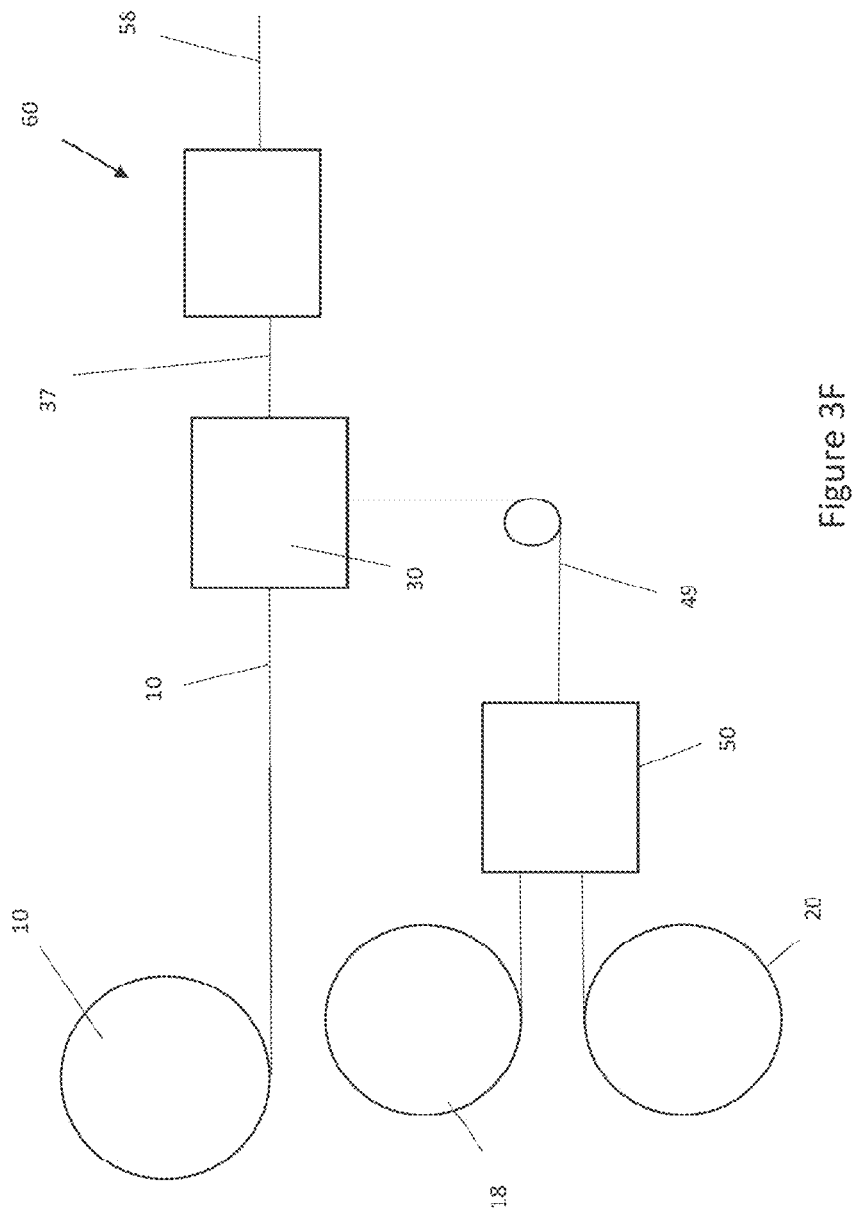

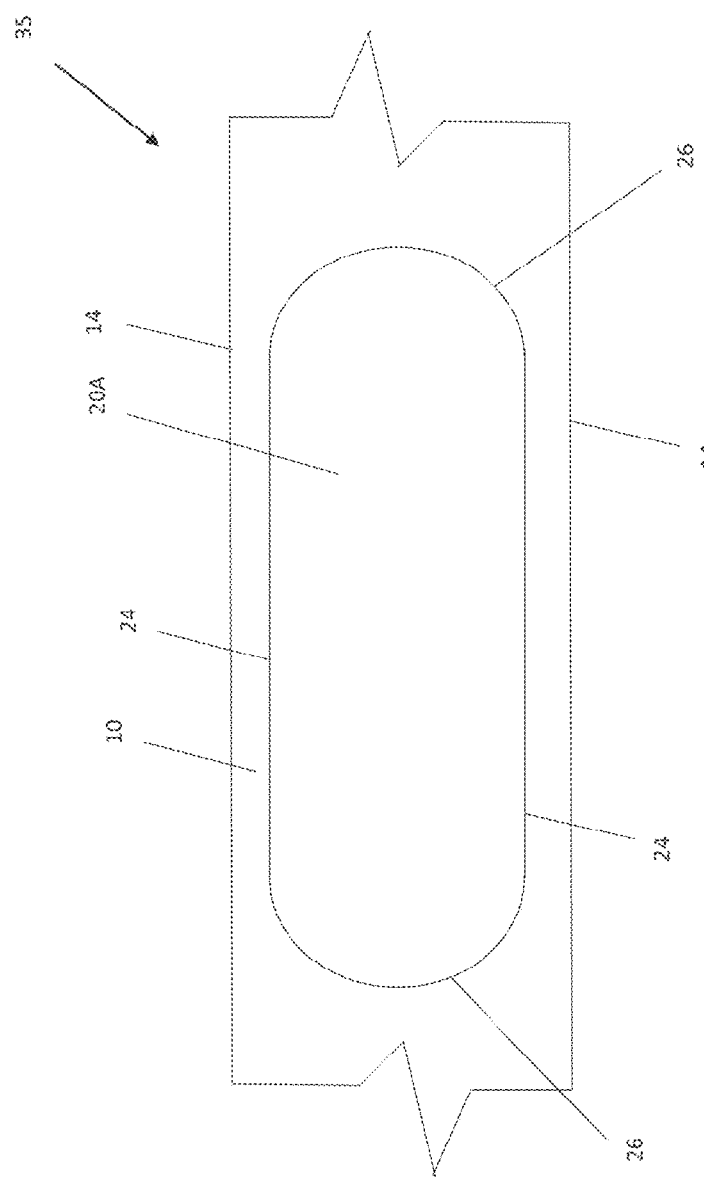

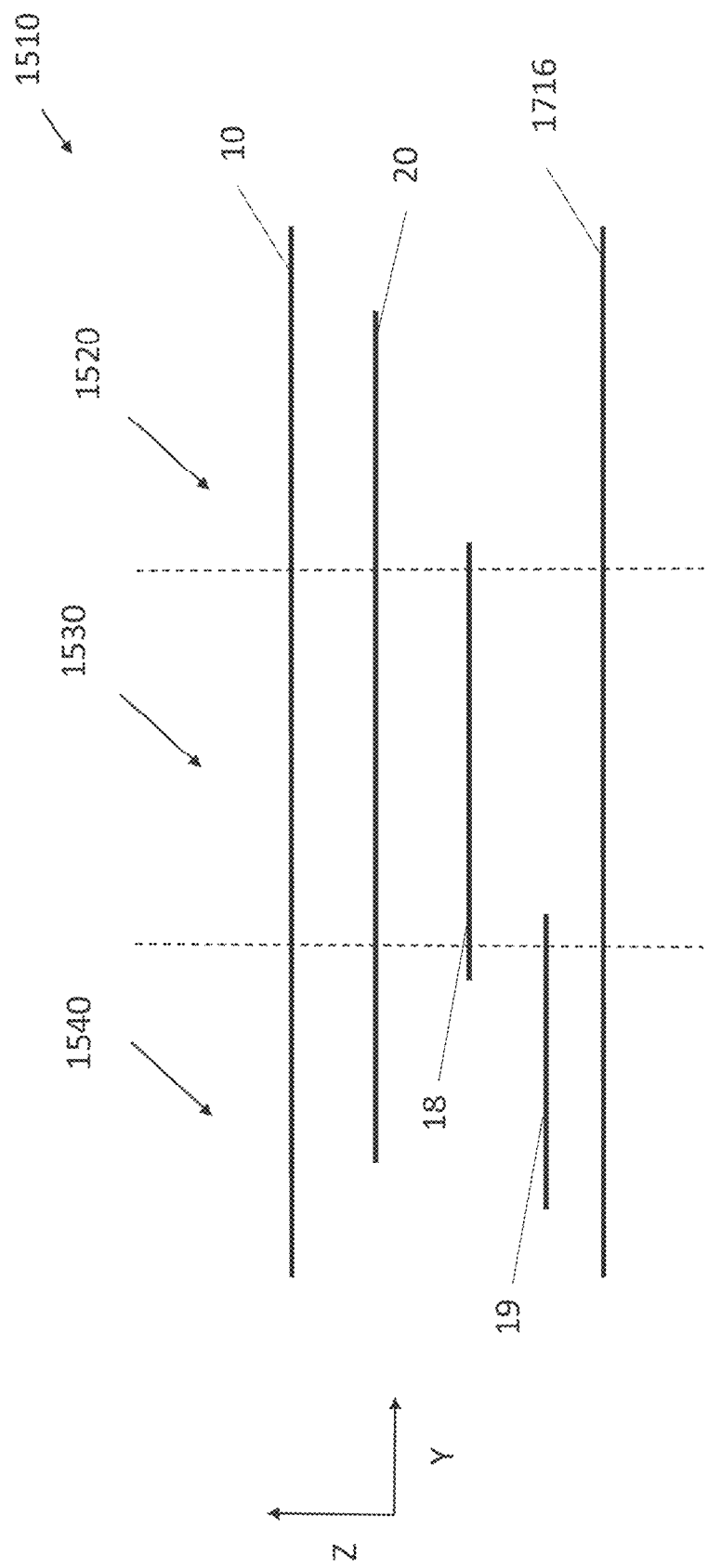

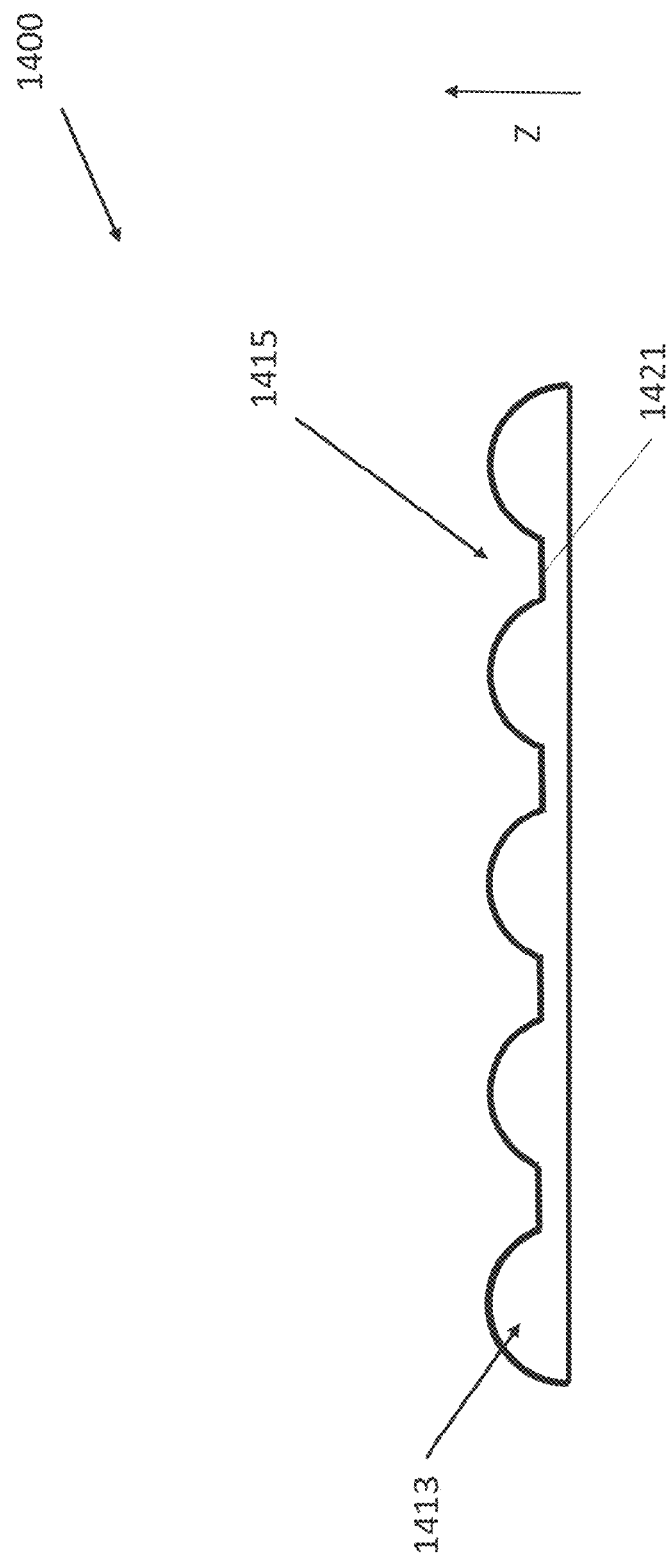

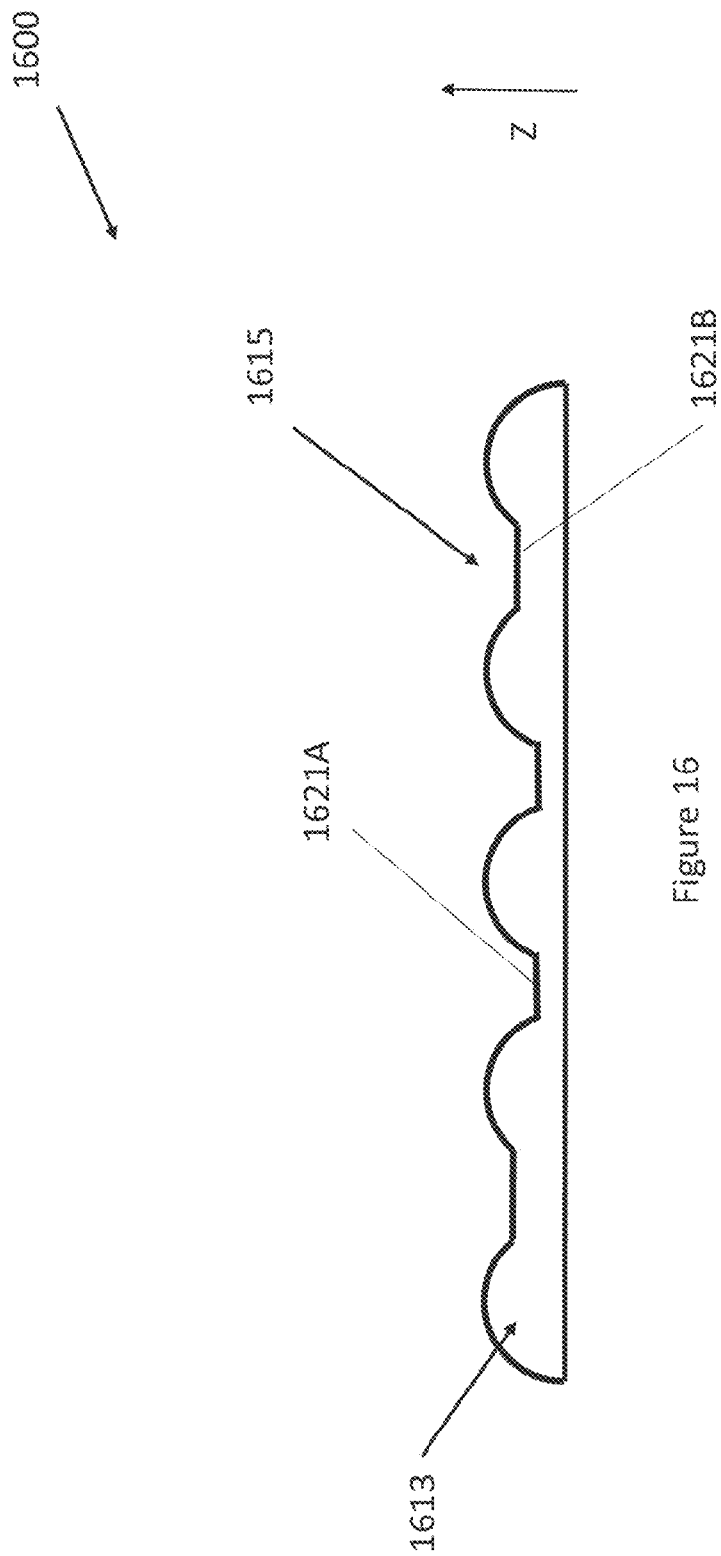

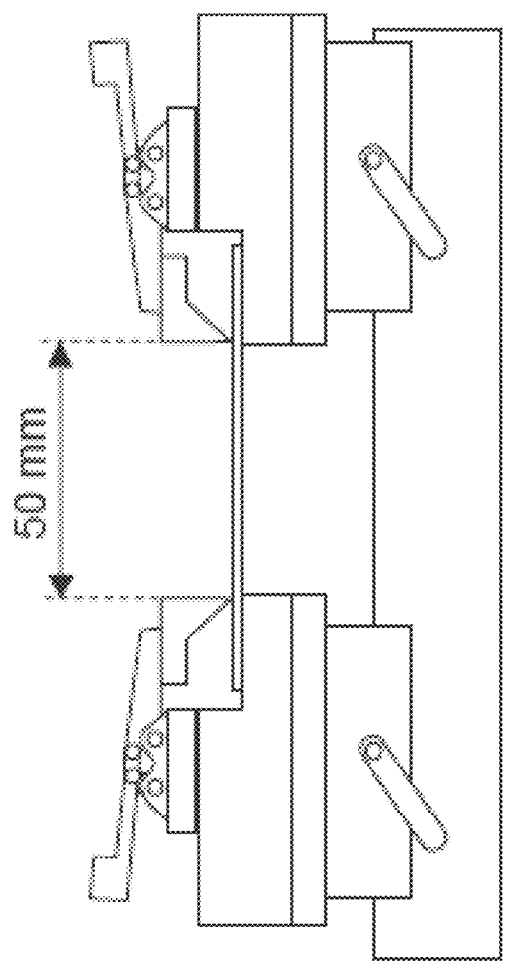

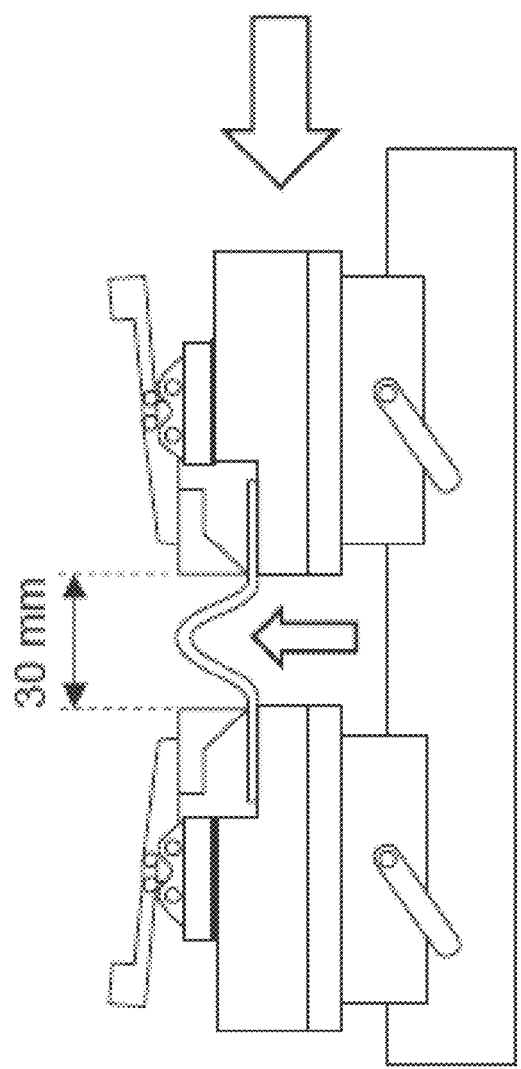

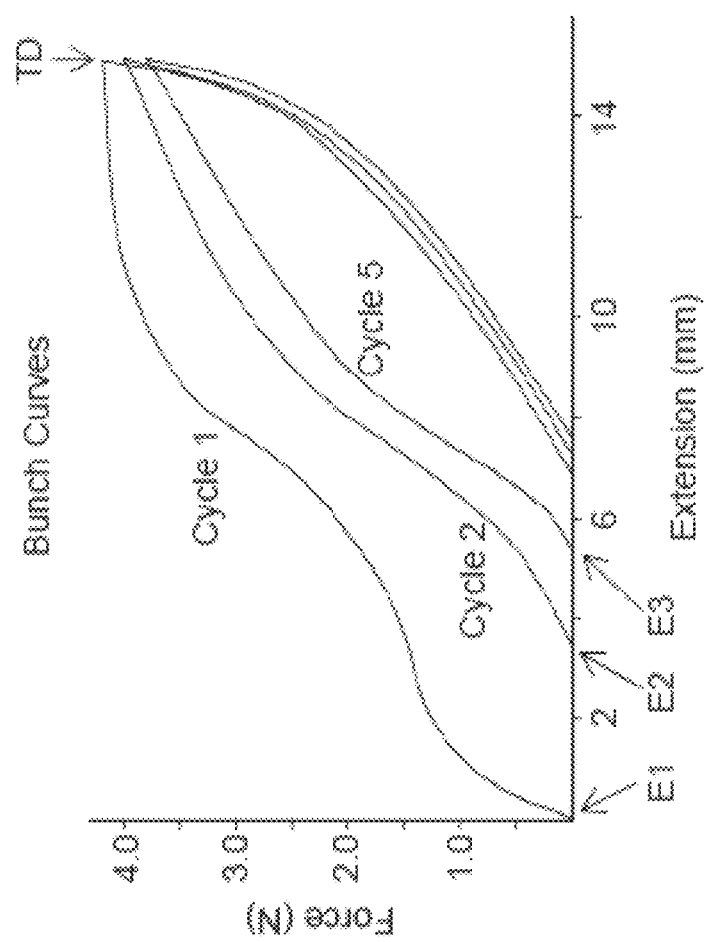

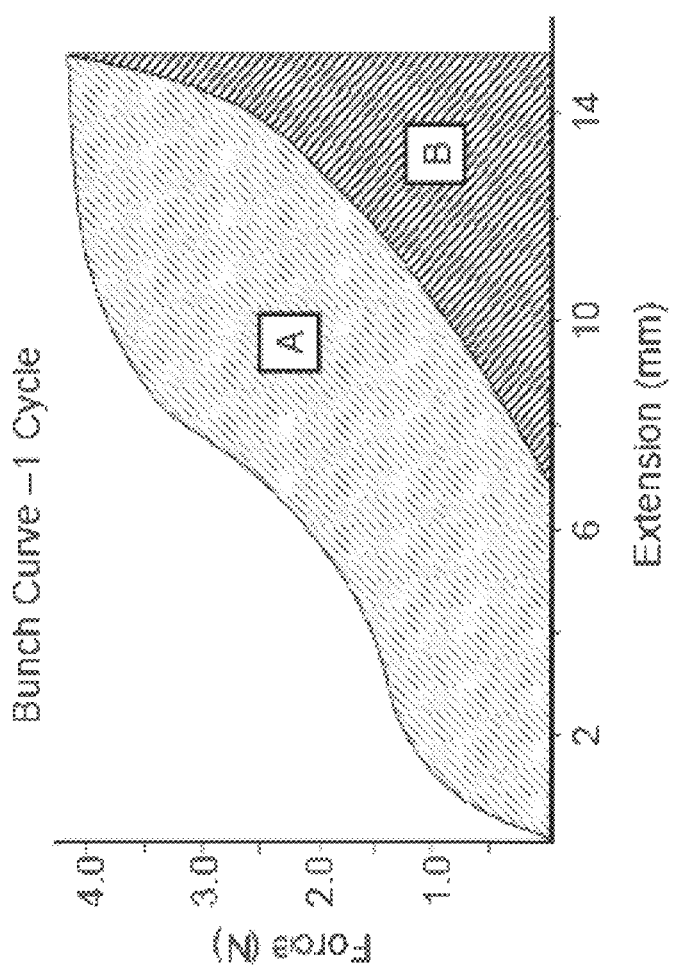

ABSORBENT ARTICLE WITH CONFORMING FEATURES

FIELD OF THE INVENTION

The present invention pertains to an absorbent article with conforming features and methods of creating the conforming feature in an absorbent article.

BACKGROUND OF THE INVENTION

Absorbent articles are widely used among consumers, e.g. diapers, training pants, feminine pads, adult incontinence pads, etc. Generally, absorbent articles such as these comprise a topsheet and a backsheet, with an absorbent core disposed therebetween. Some may include additional layers between the topsheet and the absorbent core or between the backsheet and the absorbent core to provide additional fluid management properties.

In general, the absorbent articles are expected to absorb liquid insults transferring the liquid from the point of insult on the topsheet to the absorbent core. And, once the liquid insults are absorbed, the absorbent article is expected to limit the amount of liquid which escapes the absorbent core and rewets the topsheet. For the acquisition of liquid insults, within a reasonable amount of time, the absorbent core or an additional layer between the topsheet and the core should be in liquid contact with the topsheet to adequately drain the topsheet of the liquid insult.

However, variables affecting acquisition speed can be diametrically opposed to rewet performance. For example, some conventional topsheets require a trade-off between capillarity, permeability, and rewet properties. So, while good liquid acquisition can be achieved by making the topsheet hydrophilic so that fluid passes through quickly, the topsheet then typically suffers from poor rewet performance. And the converse is also true. A hydrophobic topsheet may provide better rewet performance; however, fluid acquisition times will likely increase due to the hydrophobic nature of the topsheet.

Additionally, the absorbent article, in addition to fluid acquisition and rewet performance, is expected to provide the user with a comfortable feel. Particularly in the context of feminine hygiene articles or feminine adult incontinence articles, this can be a real challenge. While some articles may be created which provide great conformity to the intricate female anatomy, such conformity can reduce the structural integrity of the absorbent article. The reduced structural integrity of the article can cause bunching during use and also inhibit recovery of the article to its original form. And unfortunately, the bunching of the article can lead to discomfort for the wearer and leakage during use.

As such, it would be beneficial to have an improved absorbent article which addresses the tradeoff of comfortable conformance and resiliency as well as one that provided good fluid kinetics. And, it would be beneficial to provide a method for creating such articles without sacrificing leakage performance of the absorbent article.

SUMMARY OF THE INVENTION

This present disclosure relates to absorbent articles with improved fluid transfer kinetics between layers and unexpectedly improved mechanical fit and comfortable conformation to the body and methods of making the same.

The disposable absorbent articles of the present disclosure comprise a plurality of layers assembled together to form a completed article. For example, the disposable absorbent articles of the present disclosure comprise a topsheet, a backsheet, and an absorbent core disposed between the topsheet and the backsheet. A fluid management layer, e.g. secondary topsheet or acquisition layer, may be disposed between the topsheet and the absorbent core. Additional layers may be positioned between the absorbent core and the backsheet and/or the absorbent core and the topsheet.

The disposable absorbent articles of the present disclosure may comprise a longitudinal centerline and a lateral centerline, a topsheet; a backsheet; an absorbent core comprising a plurality of absorbent fibers disposed between the topsheet and the backsheet; and a first plurality of conforming features in at least the absorbent core or a combination of the absorbent core and the topsheet, wherein the disposable absorbent article has blot residual value of less than 30 mg and a bending stiffness of less than 12.

BRIEF DESCRIPTION OF THE DRAWINGS

FIGS. 3A-3F are schematics diagrams showing processes for creating intimate contact between/among webs of the present disclosure.

FIG. 4 is a schematic representation of the topsheet and acquisition/distribution laminate web with a discrete acquisition/distribution web portion being depicted on top of a topsheet web.

FIGS. 11C-11E are schematic cross-sections along a longitudinal direction showing additional forms of absorbent article in accordance with the present disclosure.

FIG. 14 is a schematic cross section of the webs of the present disclosure showing exaggerated features for ease of visualization.

FIG. 16 is a schematic cross section of the webs of the present disclosure showing exaggerated features for ease of visualization.

FIGS. 26A-B relate to the test method of FIG. 25.

FIGS. 27A-B relate to the test method of FIG. 25.

DETAILED DESCRIPTION OF THE INVENTION

Figure 1A:
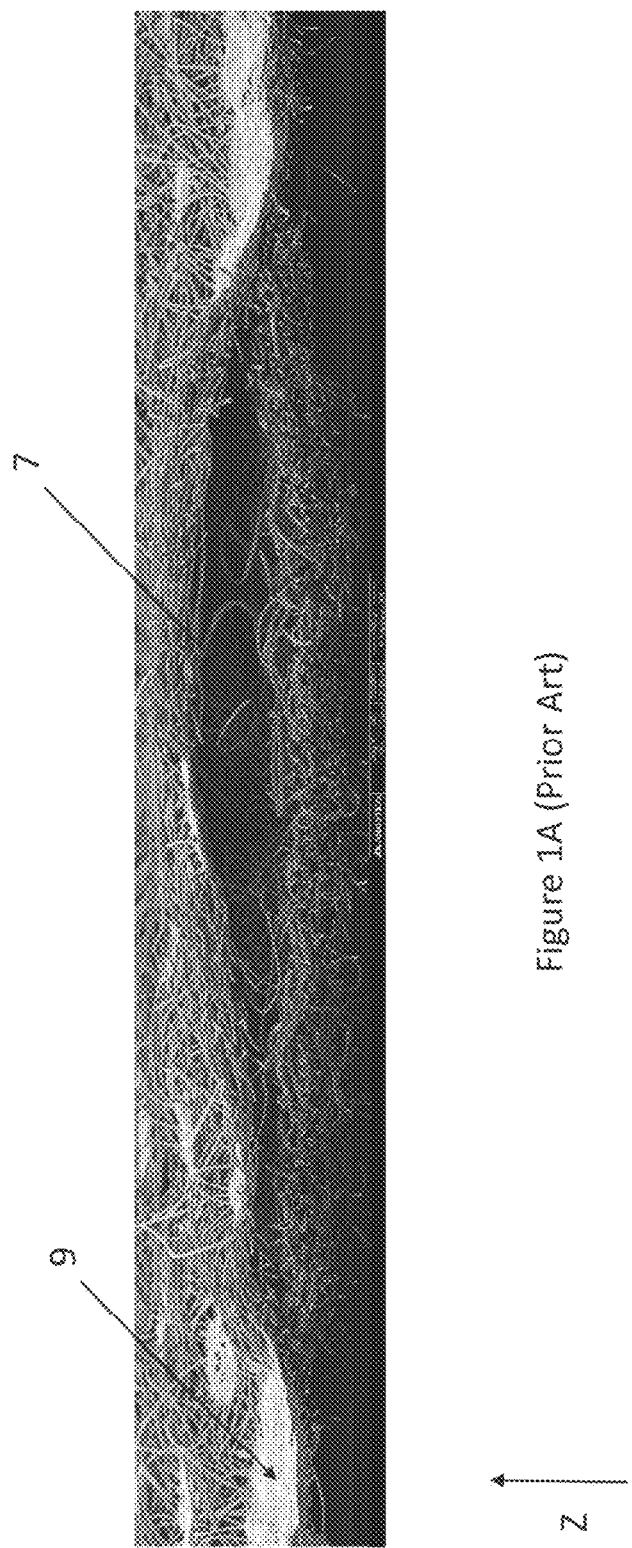
FIGS. 1A and 1B are cross sectional views showing a laminate of two materials joined via conventional laminating techniques.

As used herein "disposable absorbent article" or "absorbent article" shall be used in reference to articles such as diapers, training pants, diaper pants, refastenable pants, adult incontinence pads, adult incontinence pants, feminine hygiene pads, tampons, pessary devices, cleaning pads, and the like, each of which are intended to be discarded after use.

As used herein "hydrophilic" and "hydrophobic" have meanings as well established in the art with respect to the contact angle of water on the surface of a material. Thus, a material having a water contact angle of greater than about 90 degrees is considered hydrophobic, and a material having a water contact angle of less than about 90 degrees is considered hydrophilic. Compositions which are hydrophobic, will increase the contact angle of water on the surface of a material while compositions which are hydrophilic will decrease the contact angle of water on the surface of a material. Notwithstanding the foregoing, reference to relative hydrophobicity or hydrophilicity between a material and a composition, between two materials, and/or between two compositions, does not imply that the materials or compositions are hydrophobic or hydrophilic. For example, a composition may be more hydrophobic than a material. In such a case neither the composition nor the material may be hydrophobic; however, the contact angle exhibited by the composition is greater than that of the material. As another example, a composition may be more hydrophilic than a material. In such a case, neither the composition nor the material may be hydrophilic; however, the contact angle exhibited by the composition may be less than that exhibited by the material.

The term "filament" refers to any type of artificial continuous strand produced through a spinning process, a melt-blowing process, a melt fibrillation or film fibrillation process, or an electrospinning production process, or any other suitable process to make filaments. The term "continuous" within the context of filaments are distinguishable from staple length fibers in that staple length fibers are cut to a specific target length. In contrast, "continuous filaments" are not cut to a predetermined length, instead, they can break at random lengths but are usually much longer than staple length fibers.

As used herein, "machine direction" refers to the direction in which a web flows through an absorbent article converting process. For the sake of brevity, may be referred to as "MD".

As used herein "cross machine direction" refers to the direction which is perpendicular to the MD. For the sake of brevity, may be referred to as "CD".

Absorbent articles of the present disclosure may provide improved fluid handling, conformity and recovery. By utilizing repeating patterns of bending modes on a meso-scale versus historical micro and/or macro scale that are bendable and shapeable based on each user's unique anatomical shape and how the user deforms the absorbent system while wearing, it has been found that an absorbent structure can be created that is able to have improved contact between the absorbent product and the user.

The inventors have surprisingly found that with the creation of intimate contact between layers of the absorbent article, improved fluid kinetics may be achieved along with improved mechanical fit. The inventors have also found that if not implemented correctly, such intimate contact between layers can create leakage issues with their respective absorbent articles. Additionally, depending on the scale of the integration, the inventors have surprisingly found that some integration processes can provide the additional benefit of conformity to the complex contours of a user's body in addition to fluid kinetics benefits.

Figure 1B:
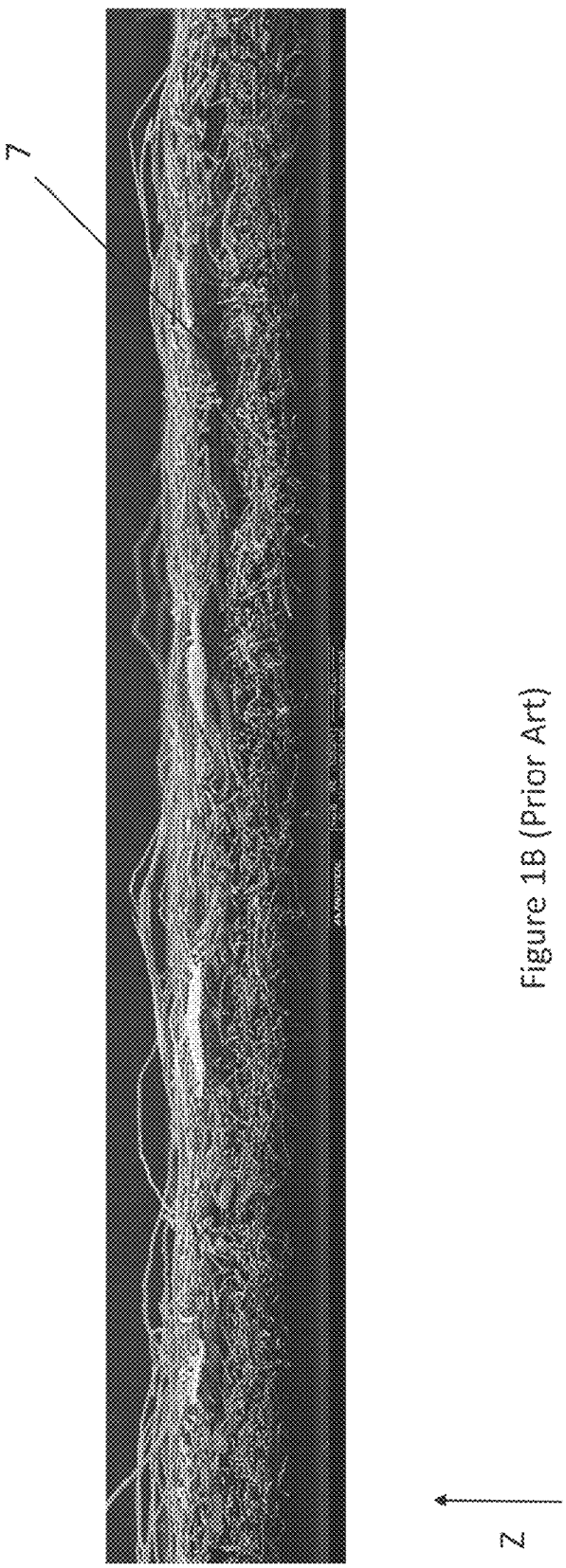

Cross sections of conventionally processed topsheet and secondary topsheet combinations which lack intimate contact are shown in FIGS. 1A and 1B. In FIG. 1A, a topsheet is shown fusion bonded to a secondary topsheet in cross-section. While the layers are joined together, they lack the intimate contact. For example, an opening 7 is shown between the topsheet and secondary topsheet. Additionally, fusion bond areas 9, while arguably integrating the constituent material of the topsheet and the secondary topsheet, destroy the form of the constituent material and instead form film-like areas through which liquid does not pass. So, the fusion bonded topsheet and secondary topsheet lack the intimate contact described herein.

In FIG. 1B, the cross-sectional view of a topsheet and a secondary topsheet joined via gluing is shown. Similar to the topsheet and secondary topsheet configuration of FIG. 1A, the configuration shown in FIG. 1B also comprises an opening 7 between the topsheet and the secondary topsheet. So, like the fusion bonded configuration, the glued configuration does not provide the intimate contact between the topsheet and secondary topsheet that is desired and described herein.

Another conventional method to encourage contact between layers involves the utilization of vacuum. During formation, a substrate, e.g. nonwoven, may be exposed to a vacuum conveyor. Additional material, e.g. fibers, can be deposited on the substrate. At the interface between the substrate and the fibers, the vacuum can induce some material integration; however, this is considered more of a surface phenomenon rather than the intimate contact created via integration disclosed herein.

Further, while embossing arguably creates intimate contact between adjacent layers, embossing tends to create areas of densification through compression. And, as noted previously, the densification of areas can create localized stiffness which can create conformity issues and can negatively impact consumer comfort during use. So, the desired intimate contact between adjacent layers of the present description does not include embossing.

Figure 2A:
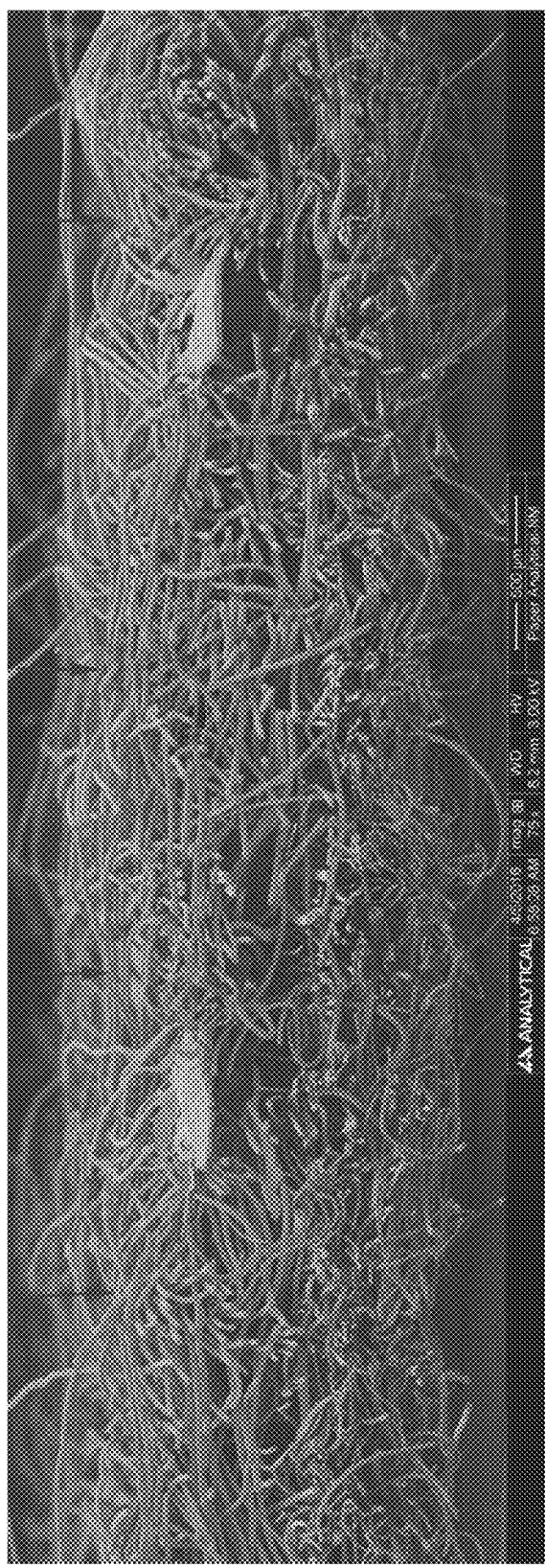
FIG. 2A is a cross sectional view of a topsheet and secondary topsheet in accordance with the present disclosure.

In contrast to the conventional configurations shown in FIGS. 1A and 1B, a cross section of a topsheet and secondary topsheet of the present disclosure is shown in FIG. 2A. FIG. 2A shows a cross section of a topsheet hydroentangled with a secondary topsheet. As shown, constituent material of the topsheet and constituent material of the secondary topsheet are integrated in a Z-direction. This Z-direction integration can create intimate contact between the topsheet and the secondary topsheet throughout the cross section of the topsheet and the secondary topsheet such that there are no openings or a reduced number of openings between the topsheet and the secondary topsheet.

As used herein, "intimate contact" refers to the integration of layers of an absorbent article. The integration causes constituent material of the layers to be in contact such that constituent material of a lower layer is more readily accessible through an upper layer. For example, via the merging of constituent material between layers, the constituent material of the lower layer is more readily accessible through the upper layer. And, as noted previously, intimate contact between/among layers allows for a more efficient fluid transfer from an upper layer to a lower layer rather than inhibiting such fluid transfer as noted with embossing and bonding. For example, it is believed that filaments and/or fibers from one layer penetrate into the adjacent layer. It is believed that this filament and/or fiber penetration provides a bridge crossing the interface between one layer to another. It is further believed that this bridge facilitates fluid transfer from one layer to another. And unlike the conventional processes described previously, the intimate contact created by the processes described herein can create integration of material layers not only at the surface but millimeters deep into an adjacent layer. Additionally, by creating intimate contact between adjacent layers as described herein, the resultant absorbent article may then be less reliant on glues to hold layers together. Glues tend to increase stiffness which can negatively impact conformability and may, in some instances, inhibit fluid transfer. Lastly, the intimate contact described herein is unlike the surface interaction (two-dimensional) created by vacuum formation in that intimate contact via the processes described in the present disclosure can create provide three-dimensional access to the material of an underlying layer, e.g. an absorbent core.

Figure 2B:
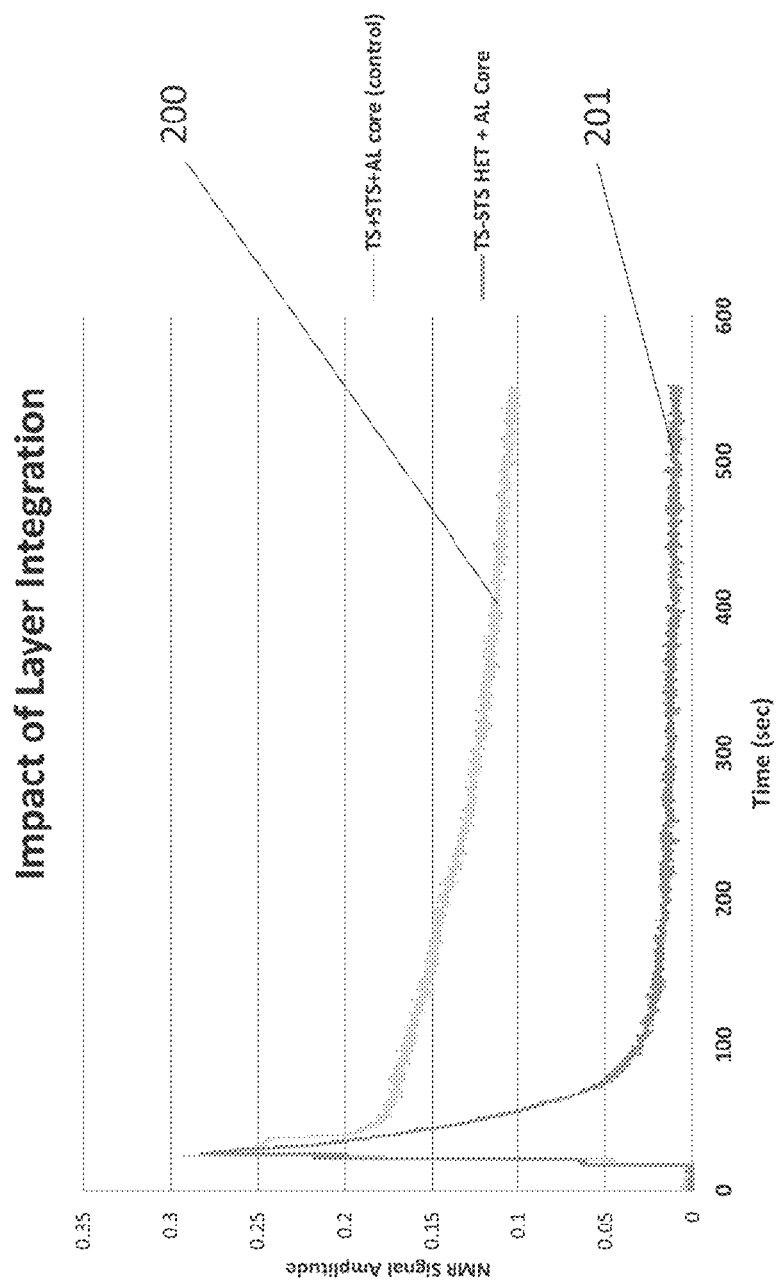
FIG. 2B is a graph depicting the fluid management data between conventionally processed laminates and the materials of the present disclosure.

Data showing the fluid acquisition speed of the hydroentangled topsheet/secondary topsheet combination is shown in FIG. 2B. As shown in FIG. 2B, a hydroentangled topsheet and secondary topsheet coupled with an absorbent core are represented by curve 201 and a conventionally processed topsheet, secondary topsheet, and absorbent core are shown by curve 200. As shown, the sample having the hydroentangled topsheet and secondary topsheet exhibits quicker fluid acquisition as depicted by the slope of the curve 201 versus curve 200. Additionally, over time, the sample with the hydroengangled topsheet and secondary topsheet moves fluid more quickly from the surface of the topsheet than does the conventionally processed topsheet, secondary topsheet, and absorbent core combination. The data shown in FIG. 2B was acquired via NMR-Mouse, e.g. Profile NMR-MOUSE model PM25 with High-Precision Lift available from Magritek Inc., San Diego, CA. The NMR-Mouse measured the level of liquid in the top 200 microns of the topsheet, secondary topsheet, and absorbent core samples shown in FIG. 2B.

Figure 2C:
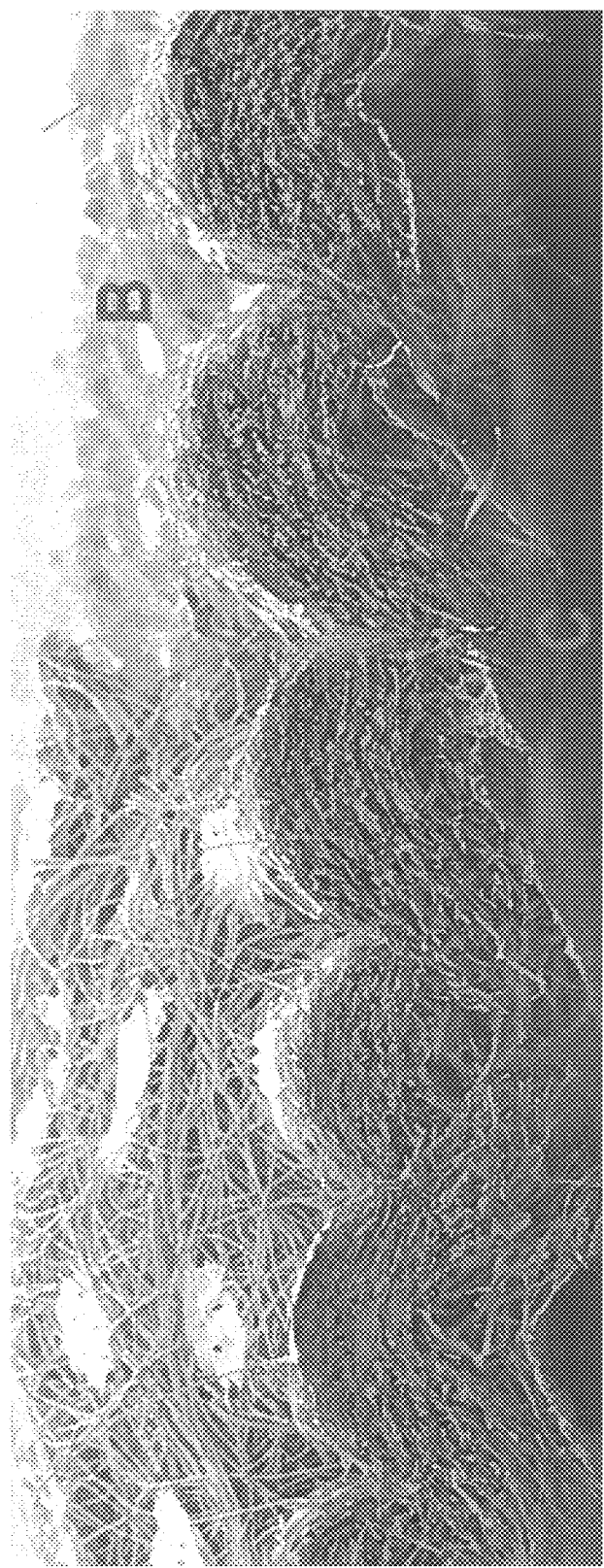
FIG. 2C is a cross sectional view of a topsheet and absorbent core in accordance with the present disclosure.

FIG. 2C is a cross sectional view of a topsheet in intimate contact with an absorbent core in a Z-direction. Much like the topsheet and the secondary topsheet, there are no apparent openings between the topsheet and the absorbent core. The topsheet and the absorbent core were subjected to meso-scale processing as described herein. As shown, there are a plurality of peaks and depressions. Due to the intimate contact between the topsheet and the absorbent core, it is believed that such construction of the topsheet/absorbent core laminate, would improve fluid acquisition and rewet.

The disposable absorbent articles of the present disclosure comprise at least one intimate contact region where a topsheet, a secondary topsheet, an absorbent core, additional layers between the topsheet and a backsheet, or any combinations thereof, comprises intimate contact. Forming intimate contact between layers requires operations which mechanically manipulate the constituent material of adjacent layers. For example, the constituent material of adjacent layers may be manipulated via hyrdroentangling as discussed above regarding FIGS. 2A and 2B or meso-scale processing as mentioned regarding FIG. 2C. These processes can create intimate contact between or among adjacent layers of an absorbent article. Additional processes for creating intimate contact between layers in an absorbent article are disclosed herein. And, combinations of processes may be utilized. For example, some layers may be hydroentangled/needlepunched while other layers may be integrated via another process that is not hydroentangling/needlepunched. Or, the hydroentangled/needlepunched layers subsequently may be combined with another layer via a different process than hydroentangling/needlepunching. Or, some layers may be integrated via meso-scale processes without being hydroentangled/needlepunched.

It is worth noting that in addition to hydroentangling, it is believed that some processes which are taught to be utilized for lofting materials, e.g. nonwovens, may also provide some amount of intimate contact between layers. These processes generally utilize hot air jets to move fibers of material. The process is described in detail in U.S. Pat. No. 8,720,021 which is incorporated herein by reference. So where the provision of hydroentangling or needlepunching is mentioned, the provision of hot air jetting may also be utilized.

Additionally, while nonwoven (fibrous) materials are depicted in FIGS. 2A and 2C, intimate contact may be established with a large variety of materials as described herein. For example, films may be utilized in conjunction with a nonwoven (fibrous material) as described herein. It has also been surprisingly found that using formation means to integrate the topsheet, secondary topsheet, and the absorbent core, providing a fibrous network results in improved flexibility of the pad (as measured by bunched compression). This is unlike traditional systems that become stiffer due to welding, glues, embossing, or when they improve capillarity through densification.

For the sake of brief introduction and clarity for the following disclosure, topsheets are generally soft feeling to the wearer of the absorbent article. Additionally, the topsheet should be configured to readily receive liquid insults to keep the wearer feeling dry. Topsheets are described in additional detail hereafter.

Fluid management layers, for the sake of brevity "FM" layers, are generally positioned directly below the topsheet and should be configured to quickly acquire liquid insults to the topsheet and distribute the liquid insult to an absorbent core. While FM layers may have some ability to absorb and retain liquid insults, they may be designed primarily to de-water the topsheet quickly and transfer liquid to the absorbent core. FM layers are discussed further herein as well.

Absorbent cores are the primary storage elements of the disposable absorbent articles. Absorbent cores receive and store liquid insults to the topsheet. Absorbent cores are generally positioned subjacent to the FM layer or may be positioned subjacent the topsheet. Additionally, absorbent cores tend to have more mass associated with them than other components of the absorbent article and therefore tend to also dominate the mechanical properties of the absorbent article. For example, mechanical properties such as flexibility, conformability and shapability, i.e. the shape the product assumes while worn, may be primarily influenced by the properties of the absorbent core. Absorbent cores are discussed in additional detail hereafter.

Process

The processes of the present disclosure can provide an absorbent article having regions of intimate contact between/among components of the absorbent article which can improve acquisition speed along with a reduction in the likelihood of leakage. And, as discussed herein, the processes of the present disclosure can provide an absorbent article with improved acquisition speed along with the ability to conform to much more complex surfaces than their conventional counterparts.

Intimate contact between the topsheet and the FM layer; FM layer and absorbent core; topsheet and absorbent core; or topsheet, FM layer, and absorbent core, can be achieved via mechanical manipulation of at least two of the topsheet, the FM layer, and the absorbent core. However, as noted previously, FM layers and absorbent cores are generally configured to receive liquid insults from the topsheet rapidly and/or store liquid insults. As such, both the FM layer and absorbent core are typically absorbent to a further extent than the topsheet. Without pre-processing of the FM layer and/or absorbent core, there is a risk that the FM layer and/or absorbent core is coextensive with the topsheet which could result in liquid insults leaking out of the FM layer and/or absorbent core of a finished product. And, trimming of the FM layer and/or absorbent core post joining with the topsheet while plausible, would prove to be difficult at best for high speed manufacturing.

The inventors have discovered processes which greatly reduce the likelihood of leakage via the mechanism of the FM layer and/or absorbent core being coextensive with the topsheet. By pre-processing the FM layer and/or absorbent core, the FM layer and/or absorbent core can be reduced in size, e.g. width, such that a periphery of the FM layer and/or absorbent core is disposed inboard of the periphery of the topsheet. The processes are discussed in additional detail hereafter.

As shown in FIGS. 3A and 4, a topsheet web 10 (shown as a roll) can be provided as a carrier to a cut and place operation 30. An FM web 20 (shown as a roll) can be provided to the cut and place operation 30 as well. The cut and place operation 30 can cut the FM web 20 into a plurality of discrete portions 20A.

The topsheet web 10 may be created as part of an absorbent article converting process or may be obtained from a manufacturer of suitable topsheet materials. Similarly, the FM layer may be made as part of an absorbent article converting process or may be obtained from a manufacturer of fluid management materials. The absorbent core web may similarly be created as part of the absorbent article converting line or may be obtained from a manufacturer of suitable absorbent core materials.

Still referring to FIGS. 3A and 4, the discrete portions 20A have opposing longitudinal sides 24 and lateral ends 26 connecting the opposing longitudinal sides 24. The topsheet web 10 comprises longitudinal sides 14 which are outboard of the longitudinal sides 24 of the discrete portions 20A. Lateral sides for the topsheet web 10 can be determined during subsequent processing. Where it is desired that the discrete portions 20A are not longitudinally coextensive with the topsheet web 10, the lateral sides for the topsheet web 10—after cutting—should be outboard of the lateral ends 26 of the discrete portions 20A. Additionally, it is important to ensure that the longitudinal sides 24 are inboard of the longitudinal sides 14 of the topsheet web 10. In some forms, the longitudinal sides 24 can be disposed more than 2 mm inboard, greater than 3 mm inboard, greater than 4 mm, inboard, greater than 5 mm inboard, or about 6 mm inboard, specifically reciting all values within these ranges and any ranges created thereby. The distance between the longitudinal sides 14 and the longitudinal sides 24 can be beneficial when the final product seal is created. The larger distance can ensure a robust seal between the topsheet and backsheet and/or another layer in the final absorbent product.

It should be noted that philic layers in general may be beneficially trimmed to ensure that the philic layers are not part of the edge seal of the article as this could lead to leakage. For example, the topsheet may comprise multiple layers of nonwoven material. A wearer-facing layer may be hydrophobic and a subjacent layer may be hydrophilic. With such a construction, the subjacent layer may be cut such that longitudinal edges of the subjacent layer are inboard of the edge of the hydrophobic layer. Additionally, the longitudinal edges of the subjacent layer may be spaced inboard of wings which extend laterally outward. In such construction, the hydrophobic layer may extend into the wings while the hydrophilic layer terminates inboard of the wings and/or inboard of the edge seal of the absorbent article.

The discrete portions of FM web 20A are placed on the topsheet web 10 thereby forming a topsheet and FM layer laminate web 35, hereafter, "TFM laminate web". As shown, the TFM laminate web 35 may be subjected to a first unit operation 40. The first unit operation 40 may mechanically manipulate the TFM laminate web 35 to create intimate contact between the topsheet web 10 and the discrete portions of FM web 20A thereby forming a final web 58. Various mechanical manipulations are described hereafter which can create intimate contact between the topsheet and the FM layer. Suitable mechanical manipulations are discussed in additional detail hereafter.

Still referring to FIGS. 3A and 4, the cut and place operation 30 may cut the FM web 20 in any suitable shape. For example, the discrete portions of FM web 20A may be dog-bone shaped (two bulbous ends with a narrow midsection connecting the bulbous ends). As another example, the discrete portions 20A may be tapered at a first end and/or a second end to facilitate folding of the article. In yet another example, the discrete portions 20A may comprise a shape which communicates a specific orientation of the article in which the discrete portion is placed. For example, a front end of the discrete portion 20A may be narrower than an opposing back end of the discrete portion 20A. As another example, the front end may comprise a plurality of scallops with small radii where the back end has a large radius. Each of these forms may signal to a wearer the appropriate orientation of the article in which the discrete portions 20A are disposed. If an FM layer is not provided, the FM web 20 of FIGS. 3A and 4 may be replaced by an absorbent core web. Or, an FM layer and absorbent core web may be provided to the cut and place operation 30 and subsequently processed as described herein.

Figure 3B:
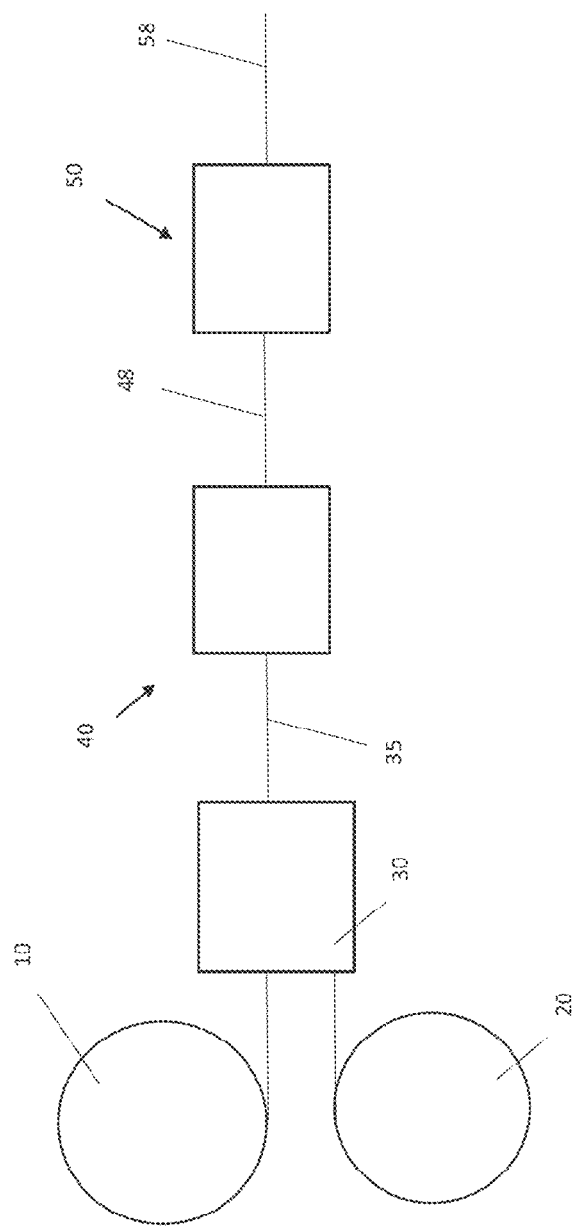

The form of the final web 58 can vary greatly depending on the unit operations involved and the way that the corresponding webs are processed. FIGS. 3B-3F disclose additional processing options which yield differing final webs 58. Referring now to FIGS. 3B and 4, the TFM laminate web 35 may be subjected to more than one unit operation. For example, after passing through the first unit operation 40, the TFM laminate web 35 may become an intermediate web 48. The intermediate web 48 may then be subjected to a second unit operation 50. Similar to the first unit operation 40, the second unit operation 50 may provide additional intimate contact between the topsheet web 10 and the discrete portions of FM web 20A. After passing through the second unit operation 50, the intermediate web 48 becomes the final web 58.

The TFM laminate web 35 may be subjected to one or more unit operations plus a needlepunching or spunlacing (hydroentangling) operation. Additional details are provided below regarding some exemplary unit operations. The order of operation of these processes may be interchanged unless specifically stated otherwise. For example, the TFM laminate web 35 may be subjected to needlepunching and/or hydroentangling prior to being subjected to a separate unit operation as described herein or vice versa. Where an FM layer is not provided, the FM web 20 of FIGS. 3B and 4 may be replaced by an absorbent core web. Or, an FM layer and absorbent core web may be provided to the cut and place operation 30 and subsequently processed as described herein.

Figure 3C:
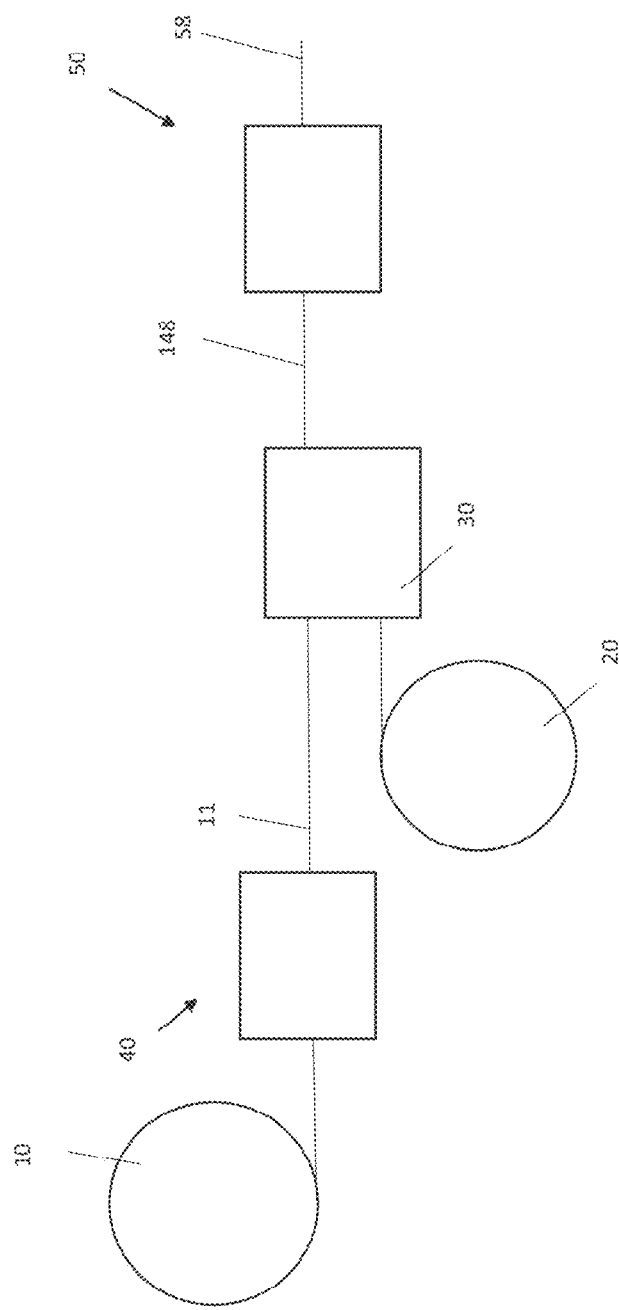

Referring now to FIGS. 3C and 4, the topsheet web 10 (shown as a roll) may pass through the first unit operation 40 prior to being supplied to the cut and place operation 30. The first unit operation 40 may mechanically manipulate the topsheet web 10 as described herein. Post mechanical manipulation by the first unit operation 40, the topsheet web 10 becomes the intermediate topsheet web 11.

Downstream of the first unit operation 40, the intermediate topsheet web 11 and the FM web 20 may be provided to the cut and place operation 30. As noted previously, the cut and place operation 30 may cut the FM web 20 into discrete portions 20A. These discrete portions may then be placed on the intermediate topsheet 11 thereby forming the intermediate topsheet and FM layer laminate or "iTFM laminate" 148. The iTFM laminate 148 may then be provided to the second unit operation 50 which provides intimate contact between the intermediate topsheet 11 and the discrete portions 20A of FM web 20. Post processing by the second unit operation 50, the iTFM laminate 148 becomes the final web 58. The second unit operation 50 may comprise a hydroentangling or needlepunching operation for integrating the layers of the iTFM laminate 148 thereby forming the final web 58. Additional unit operations may be provided in the process above to provide additional mechanical manipulation of the iTFM laminate 148.

It is worth noting that the topsheet web 10 and the FM web 20 may switch places in the process. For example, the FM web 20 may be provided to the first unit operation 40 and subsequently provided to the cut and place operation 30. The topsheet—unmanipulated— may be provided to the cut and place operation 30 along with the modified FM web 20. The remainder of the process may be as described herein. Additionally, the topsheet web 10 may pass through the first unit operation 40, and the FM web 20 may pass through a separate unit operation. The intermediate topsheet 11 and the modified FM web 20 may then be provided to the cut and place operation 30. The remainder of the process may be as described herein. Where an FM layer is not provided, the FM web 20 of FIGS. 3C and 4 may be replaced by an absorbent core web. Or, an FM layer and absorbent core web may be substituted for the FM layer 20 and subsequently processed as described herein.

Regarding FIGS. 3D and 4, the topsheet web 10 and the FM web 20 may be provided to the cut and place operation 30 as described previously regarding FIG. 3A. The resultant TFM laminate 35 may then be exposed to the first unit operation 40. The first unit operation 40 may integrate the topsheet and the FM discrete portions 20A thereby creating the intermediate web 48. Downstream of the first unit operation 40, the intermediate web 48 can be provided to a second cut and place operation 31. Along with the intermediate web 48, an absorbent core web 18 may be provided to the second cut and place operation 31. The second cut and place operation 31 may create a plurality of discrete absorbent cores from the absorbent core web 18. Much like the discrete FM portions, the discrete absorbent cores may not be coextensive with the topsheet. For example, longitudinally extending side edges of the discrete absorbent cores should be disposed laterally inboard of the longitudinally extending edges 14 of the topsheet web 10. The discrete absorbent cores may be larger than the discrete FM portions 20A, may be smaller than the discrete FM portions 20A, or may be the same size as the discrete FM portions 20A.

The plurality of discrete absorbent cores and the intermediate web 48 may be combined in the second cut and place operation 31 thereby creating an intermediate laminate and absorbent core web laminate 37, hereafter, "TFMAC laminate." The TFMAC laminate 37 can then be further processed by the second unit operation 50 thereby producing the final web 58. After the addition of the discrete absorbent cores, no further manipulation of the TFMAC laminate 37 may occur. If that is the case, then the TFMAC laminate 37 may be the final web 58.

The first unit operation may comprise a hydroentangling/ needlepunching process which integrates the layers of the topsheet and FM layer for the TFM laminate 35. The second unit operation 50 may comprise a mechanical manipulation process as described herein which integrates the layers of the TFMAC laminate 37.

Additionally, the topsheet web 10 and/or the FM web 20 may be subjected to separate unit operations prior to being provided to the cut and place operation 30. In conjunction or independent thereof, the absorbent core web 18 may be provided to a unit operation prior to being provided to the second cut and place operation 31.

Referring to FIGS. 3E and 4, the topsheet web 10 may be provided to the first unit operation 40 which mechanically manipulates the topsheet web 10 thereby forming the intermediate topsheet web 11. The absorbent core web 18 and the FM web 20 may be provided to a second unit operation 50 which mechanically manipulates and creates intimate contact between the absorbent core web 18 and FM web 20 thereby forming an absorbent core and FM web laminate, hereafter, "FMAC" laminate web 49. The intermediate topsheet web 11 and the FMAC laminate web 49 may then be provided to the cut and place operation 30. The cut and place operation 30 can cut discrete portions from the FMAC laminate web 49. The cut and place operation 30 can combine the intermediate topsheet 11 web and the discrete portions of the FMAC laminate web 49 to create an iTFMAC laminate 137. The iTFMAC laminate web 137 may then be provided to a third unit operation which integrates the layers of the iTFMAC laminate web 137.

Referring to FIGS. 3F and 4, as shown, the topsheet web 10 may be provided to the cut and place operation 30 in an unmanipulated state, i.e. sans a first unit operation 40. After the cut and slip operation 30, discrete portions of the FMAC laminate web 49 are combined with the topsheet to create the TFMAC laminate 37. In some forms, the TFMAC laminate web 37 may not be manipulated further other than processing required to create an absorbent article from the TFMAC laminate web 37. If that is the case, then the TFMAC laminate web 37 may also be the final web 58. Additionally, the FM web 20 and the absorbent core web 18 may be subjected to separate unit operations prior to being provided to the cut and place operation 30.

Referring now to FIGS. 3E and 3F, the absorbent core web 18 may be subjected to a cut and place operation and joined to the FM layer web 20 in a plurality of discrete absorbent cores. The benefit of providing the absorbent core web 18 to a cut and place operation prior to joining with the FM layer web 20 is that the cut and place operation can shape the discrete absorbent cores as desired. In contrast, where the FM layer web 20 and the absorbent core web 18 are provided to the cut and place operation in conjunction, the shape of the discrete FM portions and the discrete absorbent cores is likely going to be the same. So, for maximum flexibility in the design of the absorbent article, it may be beneficial to provide the absorbent core web 18 to a cut and place operation and then joining the discrete absorbent cores to the FM layer web 20.

The unit operations of the present disclosure may impart a variety of different features/structures to the webs which are subjected to the unit operations. Hereafter, there is a discussion of some suitable structures/features for creating intimate contact between adjacent absorbent article layers which can be created via unit operations. And as discussed hereafter, intimate contact features include conforming features, but conforming features is a smaller subset of intimate contact features as not all intimate contact features comprise conforming features.

For the discussion regarding suitable features/structures, the generic term "modified web" shall be utilized in place of the intermediate topsheet 11, intermediate web 48, iTFM laminate web 148, TFMAC laminate web 37, iTFMAC laminate web 137, FMAC laminate web 49, and final web 58, or any web that has been mechanically manipulated by a unit operation, unless otherwise noted. So, the features/structures discussed hereafter may be applied to the webs described herein. The term "precursor web" shall be utilized to refer to those webs which are unmodified (not mechanically manipulated) by a unit operation, e.g. topsheet web 10, FM web 20, absorbent core web 18, combinations thereof, and TFM laminate 35, or those webs which are upstream of one or more unit operations which will create intimate contact between two adjacent webs or portions thereof, unless otherwise noted.

Unit Operations

There are several unit operations which can be utilized to create intimate contact between adjacent layers of an absorbent article. Some examples are discussed in additional detail below.

Spunlacing

One example of a process for creating intimate contact between/among layers is hydroengangling or spunlacing. For the spunlacing unit operation, a precursor web or modified web is subjected to high-speed jets of water which causes interlocking of filaments and/or fibers of nonwoven webs. In addition to providing structural integrity to the resultant laminate, the spunlacing process can create intimate contact between nonwoven webs by creating Z-direction integration of the filaments and/or fibers of the nonwoven webs. The spunlacing process is generally known in the art. Any unit operation or a plurality thereof described herein may comprise a spunlacing process.

Needlepunching

Another example is needlepunching. Similar to spunlacing, the needlepunching process can create intimate contact between layers by creating Z-direction integration of filaments and/or fibers of nonwoven webs. Needlepunching involves the mechanical interlocking of filaments and/or fibers of a spunbonded, carded, or textile fabric web. In the needlepunching process, a plurality of barbed needles repeatedly pass in and out of a precursor web or a modified web, and push filaments and/or fibers of the webs in a positive and/or negative Z-direction. The needlepunching process is generally well known in the art. Any unit operation or a plurality thereof described herein may comprise a needlepunching process.

Protrusions/Depressions

Figure 5:
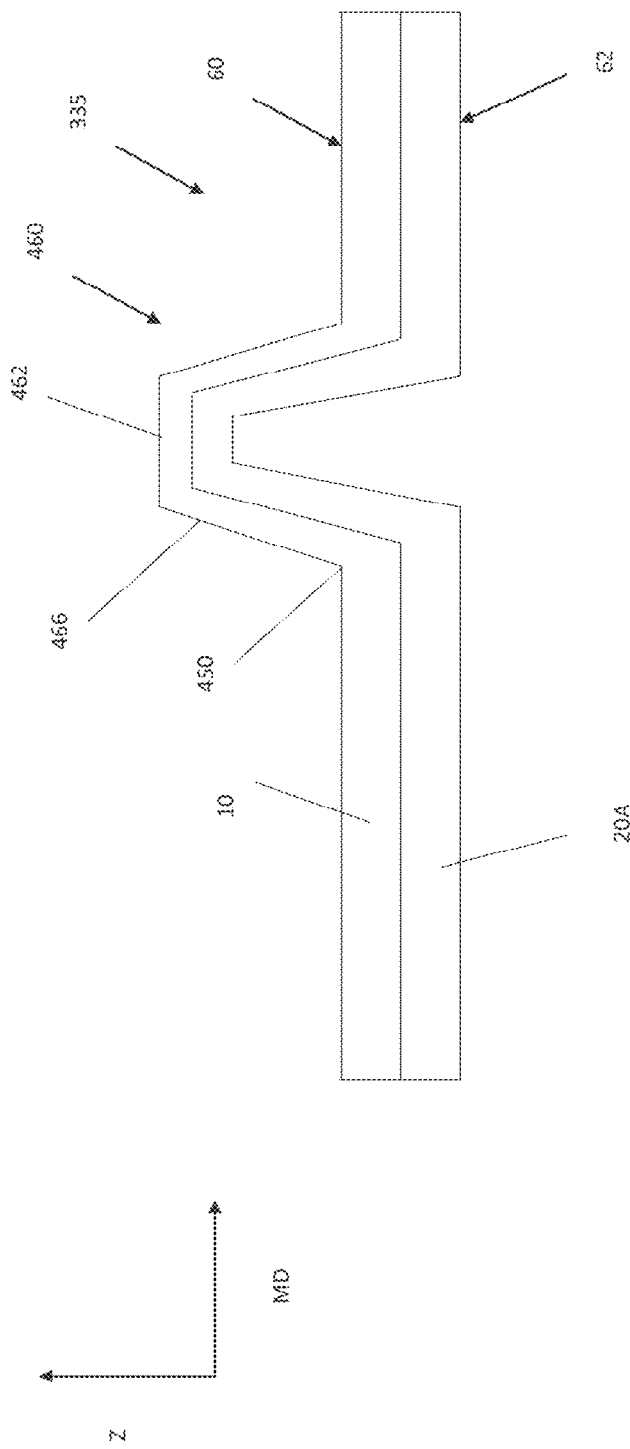
FIG. 5 is a schematic representation of the topsheet and acquisition laminate web comprising a protrusion.

Some examples of suitable unit operations for creation of intimate contact between layers of an absorbent article includes those unit operations which can create protrusions in precursor webs. Regarding FIG. 5, some unit operations described herein can produce modified webs 335 comprising protrusions 460 in a positive and/or negative Z-direction. Protrusions in the negative Z-direction may also be referred to as depressions. In general, the protrusions 460 comprise a distal end 462 and sidewalls 466 connecting the distal end to a base portion 450. And the base portion 450 connects the sidewalls 466 to a first surface 60 or an opposing second surface 62 of the modified web 335. The protrusions of the present disclosure may comprise outer tufts, tunnel tufts, filled tufts, nested tufts, ridges and grooves, and corrugations.

It is worth noting that passing the precursor web between two rolls (of opposing protrusions and groves) with a relatively small space there between will likely apply some shear and compressive forces to the material. The present processes however differ from embossing processes in which the teeth or male members compress the precursor web against an opposing roll or the bottom of the female elements, thereby increasing the density of the region in which the material is compressed. Instead, the processes described herein provide displacement of material and to the extent that there are density changes, such changes are negligible when compared to the density changes created via embossing.

Figure 6A:
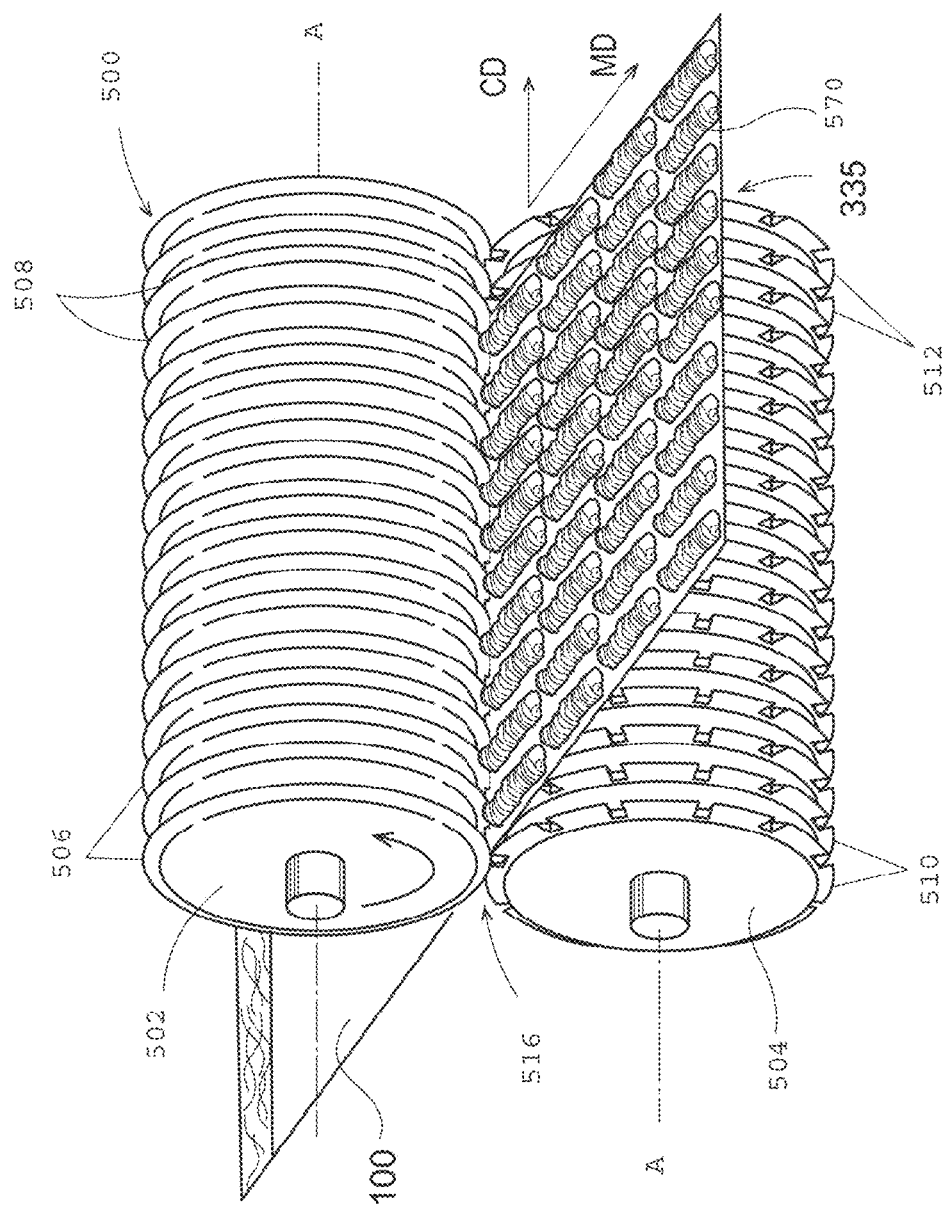
FIG. 6A is a depiction of a pair of rolls which can create protrusions in the laminate webs of the present disclosure.

Referring to FIG. 6A, the unit operations 40, 50, and 60, (shown in FIGS. 3A-3F) may comprise an apparatus 500 for forming tufts in the modified web 335. The apparatus 500 comprises a pair of intermeshing rolls 502 and 504, each rotating about an axis A—the axes A being parallel and in the same plane. Roll 502 comprises a plurality of ridges 506 and corresponding grooves 508 which extend unbroken about the entire circumference of roll 502.

The depth of engagement (DOE) is a measure of the level of intermeshing of the rolls 502 and 504. The DOE should be selected to provide the desired structure. For the purposes of fluid management, the DOE should be selected to ensure that constituent materials of the layers being manipulated, are provided with sufficient intimate contact. Additionally, clearance between ridges and grooves is going to depend greatly on the caliper of the material being manipulated. For example, where a topsheet, FM layer, and absorbent core layer are being manipulated, the clearance between the ridges and grooves may need to be higher than what it would be for a topsheet and FM layer only. Too small of a clearance could shred the webs.

Roll 504, similar to roll 502, but rather than having ridges that extend unbroken about the entire circumference, roll 504 comprises a plurality of rows of circumferentially-extending ridges that have been modified to be rows of circumferentially-spaced teeth 510 that extend in spaced relationship about at least a portion of roll 504. The individual rows of teeth 510 of roll 504 are separated by corresponding grooves 512. In operation, rolls 502 and 504 intermesh such that the ridges 506 of roll 502 extend into the grooves 512 of roll 504, and the teeth 510 of roll 504 extend into the grooves 508 of roll 502. A nip 516 is formed between the counter-rotating intermeshing rolls 502 and 504. Both or either of rolls 502 and 504 can be heated by means known in the art such as by using hot oil filled rollers or electrically-heated rollers.

The apparatus 500 is shown in a configuration having one patterned roll, e.g. roll 504, and one non-patterned grooved roll 502. However, it may be preferable to use two patterned rolls similar to roll 504 having either the same or differing patterns, in the same or different corresponding regions of the respective rolls. Such an apparatus can produce modified webs 335 with tufts protruding from both sides of modified webs 335, i.e. tufts extending in a positive Z-direction and tufts extending in a negative Z-direction. Also different rolls with different patterned regions may be utilized to create zones of different manipulation having different fluid handling and/or different mechanical properties and performance. Such configurations are discussed hereafter.

The modified webs 335 of the present disclosure can be made by mechanically deforming a precursor web 100 that can be described as generally planar and two dimensional prior to processing by the apparatus shown in FIG. 6A. By "planar" and "two dimensional" is meant simply that the precursor web 100 may start the process in a generally flat condition relative to the modified web 335 that has distinct, out-of-plane, Z-direction three-dimensionality due to the formation of tufts 570. "Planar" and "two-dimensional" are not meant to imply any particular flatness, smoothness or dimensionality. The intermeshing rolls 502 and 504 can urge the material of the precursor web 100 in the positive Z-direction or negative Z-direction depending on whether roll 504 engages the second surface 62 or the first surface 60 (shown in FIG. 5).

Referring now to FIGS. 3A-6A, the process described regarding FIG. 6A can provide for a variety of tufts, e.g. tunnel tufts, filled tufts, outer tufts. For example, tunnel tufts may be created when localized areas of constituent material of the precursor web 100 are urged in the positive Z-direction such that material of the precursor web 100 in the localized area may be urged toward the first surface 60 of the modified web 335. The localized area may be disposed superjacent to the first surface 60. It is worth noting that the webs depicted in FIGS. 3A through 5 comprises multiple layers, e.g. topsheet web 10 and discrete portions 20A of FM web 20. So where constituent material of the precursor web 100 is urged in a positive Z-direction, the tunnel tuft may comprise, as an example, constituent material of the discrete portion 20A of the FM web 20, and the topsheet web 10, as an example, may form the outer tuft.

In contrast, where localized areas of the constituent material of the precursor web 100 are urged in the negative Z-direction, material of the precursor web 100 in the localized areas may be urged toward the second surface 62. The constituent material may be disposed subjacent to the second surface 62 of the modified web 335. Where constituent material of the precursor web 100 is urged in the negative Z-direction, the tunnel tuft, as an example, would be formed by the topsheet web 10, and the outer tuft, as an example, may be formed by discrete portions 20A of the FM web 20.

Figure 6B:
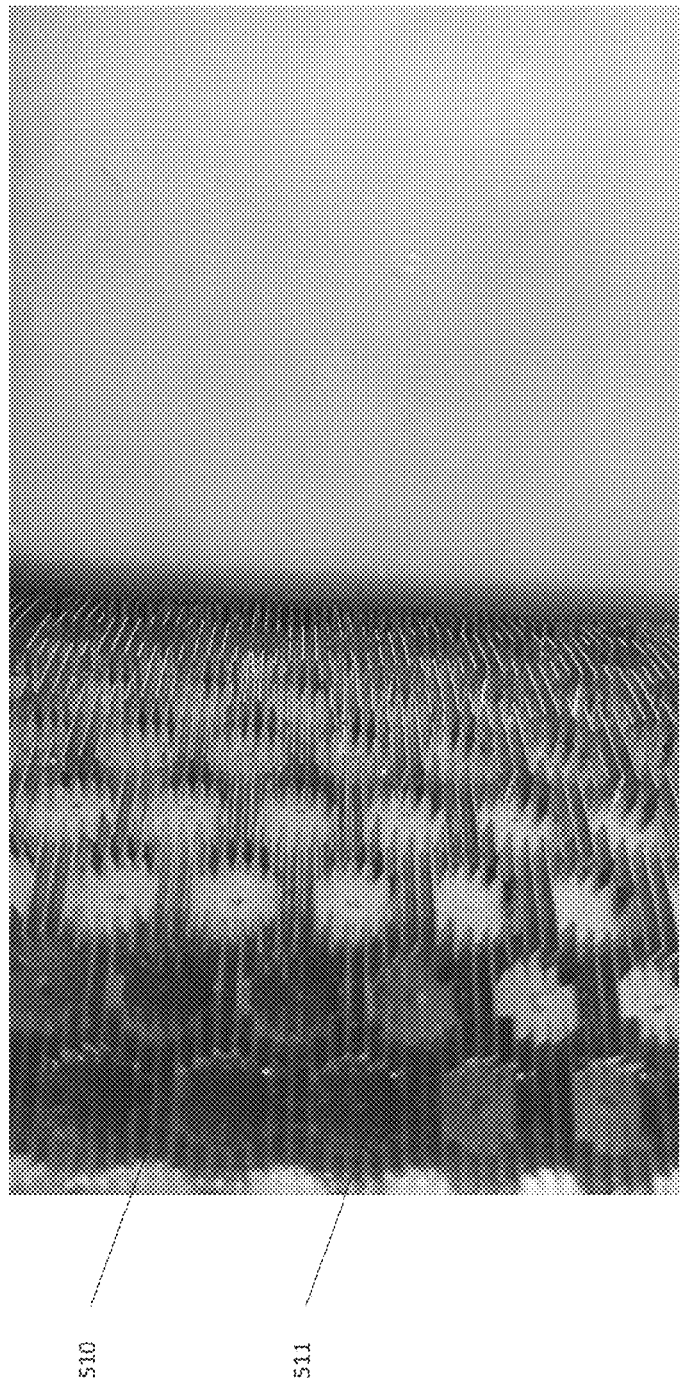
FIG. 6B is a photo showing an exemplary roll pattern which may be utilized in the apparatus shown in FIG. 6A.

A photograph of a suitable roll for use with the apparatus 500 is shown in FIG. 6B. As shown, the roll comprises teeth 510 and a plurality of open areas 511. Each of the open areas 511 is separated by teeth 510 disposed therebetween. The patterns of teeth 510 and open areas 511 correspond to the depressions and nodes, respectively in FIGS. 12A-12C, 13A-13C, and 15A-15C.

In addition to or independent of the tufts discussed heretofore, the modified web 335 may comprise filled tufts. Filled tufts may occur when the precursor web 100 comprises crimped filaments. Where the precursor web 100 of the present invention comprises crimped filaments, the precursor web 100 has a higher caliper for a given basis weight. This higher caliper can in turn deliver consumer benefits of comfort due to cushiony softness, faster absorbency due to higher permeability, and improved masking. Additional benefits may include less redmarking, higher breathability and resiliency. Crimped filaments may be utilized in a variety of layers of an absorbent article. For example, the topsheet web 10 may comprise crimped filaments, the FM web 20 may comprise crimped filaments, and/or the absorbent core may comprise crimped filaments.

The difference between filled tufts and tunnel tufts is that filled tufts generally appear filled with filaments. Because of the nature of the crimped filaments, mechanical manipulation tends to simply uncoil the filaments to some extent. In contrast, non-crimped filaments may be stretched and thinned during mechanical manipulation. This stretching and thinning generally means that these resultant tufts have far fewer fibers within its interior space thereby looking much more like a tunnel. Methods of making tunnel tufts, outer tufts, and filled tufts are discussed in additional detain in U.S. Pat. Nos. 7,172,801; 7,838,099; 7,754,050; 7,682,686; 7,410,683; 7,507,459; 7,553,532; 7,718,243; 7,648,752; 7,732,657; 7,789,994; 8,728,049; and 8,153,226. Filled tufts and corresponding outer tufts are discussed in additional detail in U.S. Patent Application Serial No. 2016/0166443.

Referring back to FIGS. 3A through 6A, the apparatus 500 for forming tufts in the precursor web 100 may be the first unit operation 40, the second unit operation 50, and/or the third unit operation 60. In some forms, the apparatus 500, aside from the cut and place operations 30 and 31, may be the only operation which provides the intimate contact between layers of the precursor web 100. Additionally, forms are contemplated where tufts, e.g. tunnel, outer, and/or filled tufts are provided in a positive Z and negative Z direction on the modified web 335.

Still another form of protrusion which is suitable for the modified webs 335 of the present disclosure comprise nested tufts. FIGS. 7A-7D depict an apparatus 600 which is suitable for use as a unit operation in accordance with the present disclosure. As shown, the precursor web 100 may be subjected to the apparatus 600. The apparatus 600 may comprise forming members 602 and 604 which may be in the form of non-deformable, meshing, counter-rotating rolls that form a nip 606 therebetween. The precursor web 100 may be fed into the nip 606 between the rolls 602 and 604. Although the space between the rolls 602 and 604 is described herein as a nip, as discussed in greater detail below, in some cases, it may be desirable to avoid compressing the precursor web 100 to the extent possible.

The first forming member (such as "male roll") 602 has a surface comprising a plurality of first forming elements which comprise discrete, spaced apart male forming elements 612. The male forming elements are spaced apart in the machine direction and in the cross-machine direction. The term "discrete" does not include continuous or non-discrete forming elements such as the ridges and grooves on corrugated rolls (or "ring rolls") which have ridges that may be spaced apart in one, but not both, of the machine direction and in the cross-machine direction.

Figures 7A, 7B:
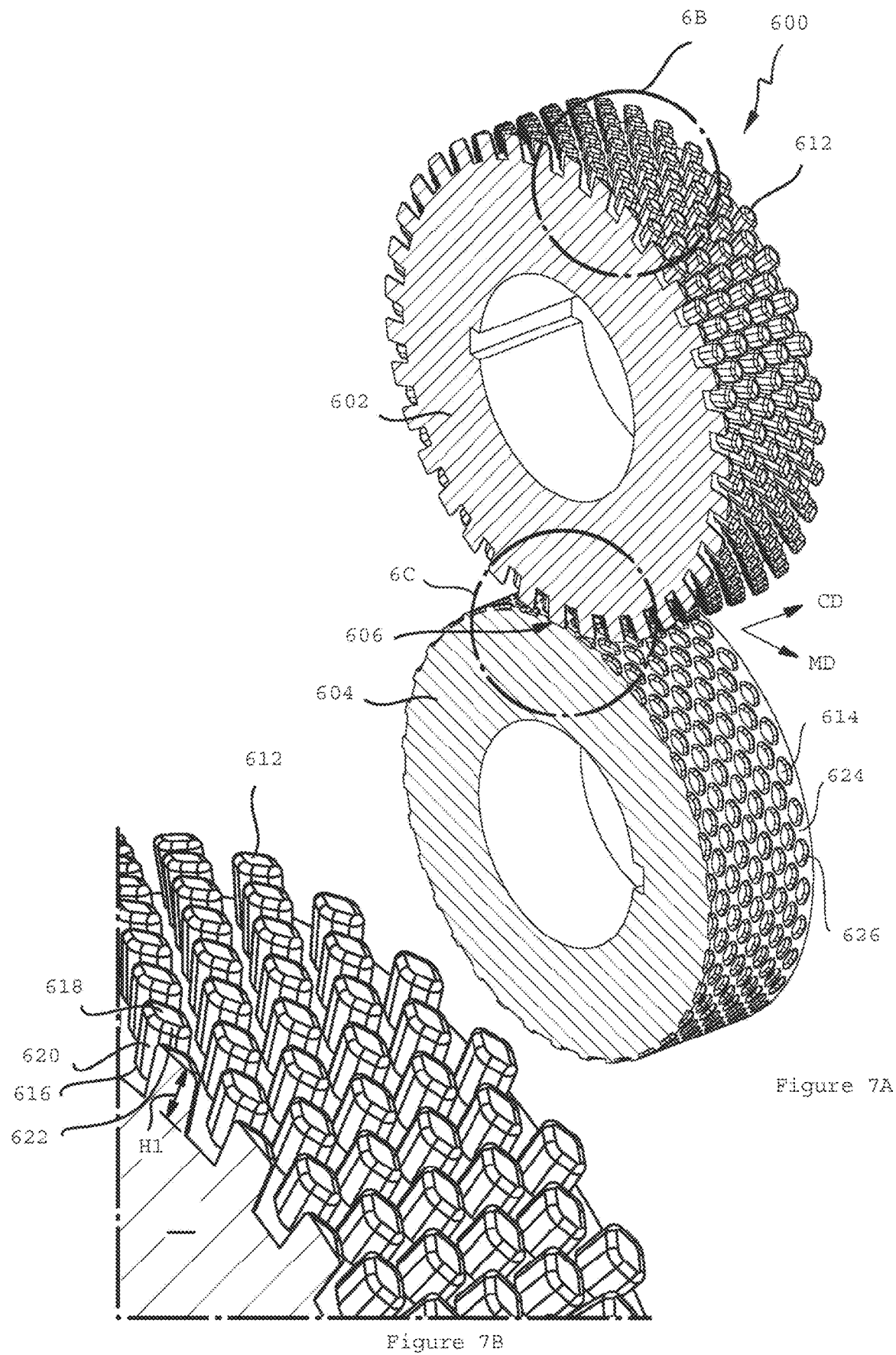
FIGS. 7A-7D are depictions of another pair of rolls which can create protrusions in the webs of the present disclosure.

As shown in FIG. 7B, the male forming elements 612 have a base 616 that is joined to (in this case is integral with) the first forming member 602, a top 618 that is spaced away from the base, and sidewalls (or "sides") 620 that extend between the base 616 and the top 618 of the male forming elements. The forming elements 612 also have a plan view periphery, and a height $H_1$ (the latter being measured from the base 616 to the top 618).

Figure 7C:
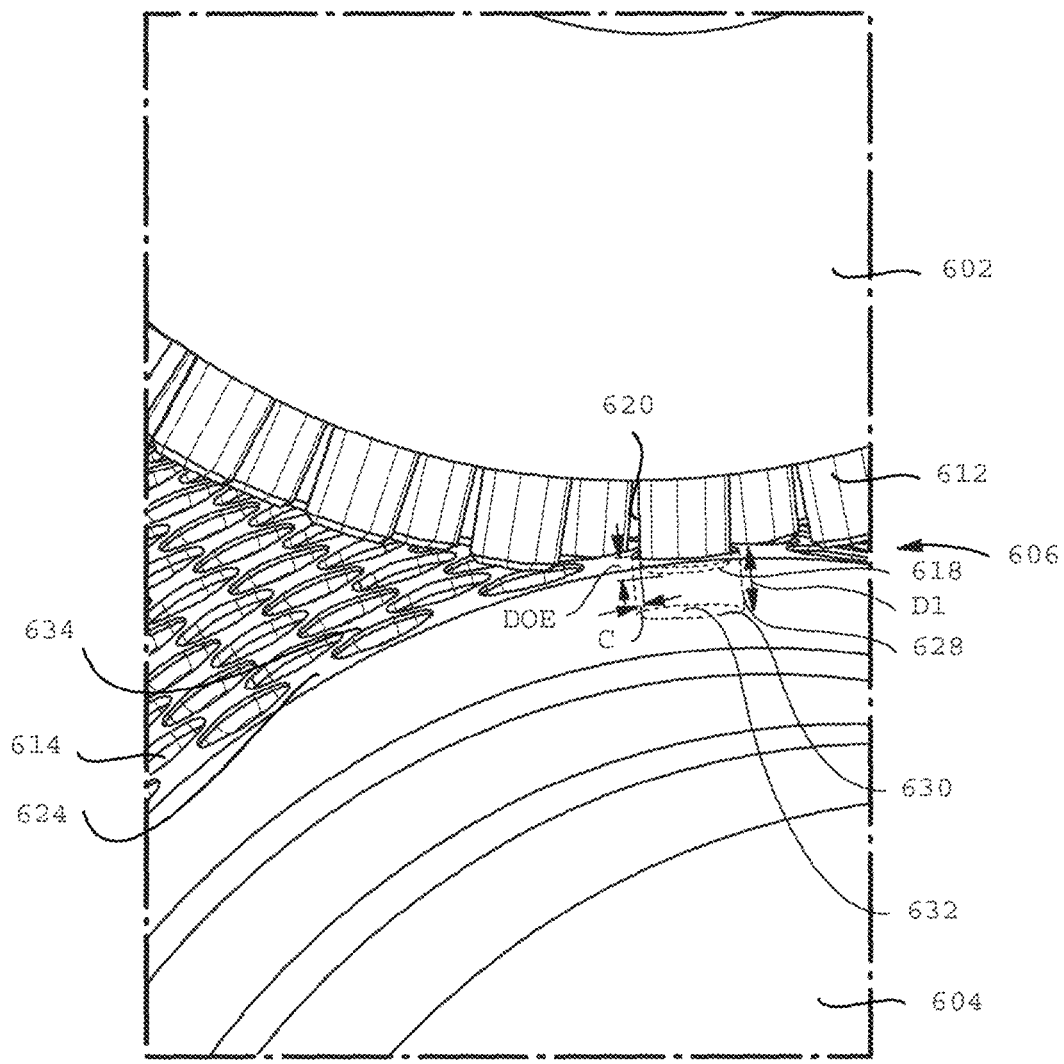

Referring again to FIGS. 7A through 7D, the second forming member (such as "female roll") 604 has a surface 624 having a plurality of cavities or recesses 614 therein. The recesses 614 are aligned and configured to receive the male forming elements 612 therein. Thus, the male forming elements 612 mate with the recesses 614 so that a single male forming element 612 fits within a periphery of a single recess 614, and at least partially within the recess 614 in the Z-direction. The recesses 614 have a plan view periphery 626 that is larger than the plan view periphery of the male elements 612. As a result, the recesses 614 on the female roll 604 may completely encompass the male forming elements 612 when the rolls 602 and 604 are intermeshed. As shown in FIG. 7C, the recesses 614 have a depth D1 which in some forms may be greater than the height H1 of the male forming elements 612. The recesses 614 have a plan view configuration, sidewalls 628, a top edge or rim 634 around the upper portion of the recess where the sidewalls 628 meet the surface 624 of the second forming member 604, and a bottom edge 630 around a bottom 632 of the recesses where the sidewalls 628 meet the bottom 632 of the recesses.

As discussed above, the recesses 614 may be deeper than the height $H_1$ of the forming elements 612 so the precursor web 100 is not nipped (or compressed) between the male forming elements and the recesses to the extent possible.

The depth of engagement (DOE) is a measure of the level of intermeshing of the forming members. As shown in FIG. 7C, the DOE is measured from the top 618 of the male elements 612 to the (outermost) surface 624 of the female forming member 614 (e.g., the roll with recesses). The DOE should be sufficiently high, when combined with extensible nonwoven materials, to create nested tufts.

Still referring to FIG. 7C, there is a clearance, C, between the sides 620 of the forming elements 612 and the sides (or sidewalls) 628 of the recesses 614. The clearances and the DOE's are related such that larger clearances can permit higher DOE's to be used. The clearance, C, between the male and female roll may be the same, or it may vary around the perimeter of the forming element 612. For example, the forming members can be designed so that there is less clearance between the sides of the forming elements 612 and the adjacent sidewalls 628 of the recesses 614 than there is between the sidewalls at the end of the male elements 612 and the adjacent sidewalls of the recesses 614. In other cases, the forming members can be designed so that there is more clearance between the sides 620 of the male elements 612 and the adjacent sidewalls 628 of the recesses 614 than there is between the sidewalls at the end of the male elements 612 and the adjacent sidewalls of the recesses. In still other cases, there could be more clearance between the side wall on one side of a male element 612 and the adjacent side wall of the recess 614 than there is between the side wall on the opposing side of the same male element 612 and the adjacent side wall of the recess. For example, there can be a different clearance at each end of a forming element 612; and/or a different clearance on each side of a male element 612.

Some of the aforementioned forming element 612 configurations alone, or in conjunction with the second forming member 604 and/or recess 614 configurations may provide additional advantages. This may be due to by greater lock of the modified web 335 on the male elements 612, which may result in more uniform and controlled strain on the modified web 335. The apparatus 600 is further described in U.S. Patent Application Serial No. 2016/0074252.

Figure 7D:
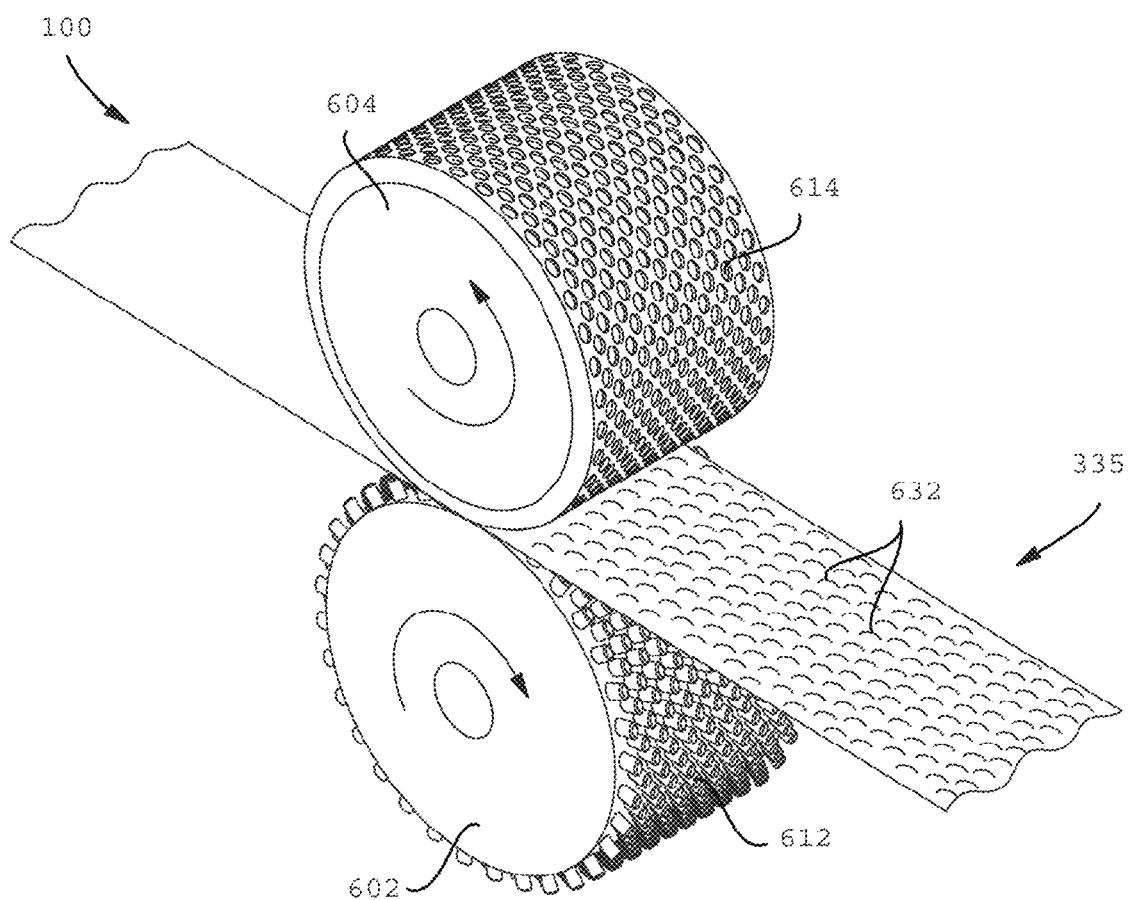

As shown in FIG. 7D, the precursor web 100 may be provided to the nip 606 between the first roll 602 and the second roll 604. As the precursor web 100 passes through the nip 606, the forming members 612 engage the second surface 62 (shown in FIG. 5) of the precursor web 100 and urge constituent material of the precursor web 100 into the recesses 614. The process forms the modified web 335 having a planar first surface and a plurality of integrally formed nested tufts extending outward from the first surface 60 (shown in FIG. 5) of the modified web 335. (Of course, if the second surface 62 of the modified web 335 is placed in contact with the second forming member 604, the nested tufts will extend outward from the second surface 62 of the modified web 335, and the openings will be formed in the first surface 60 of the modified web 335.)

Referring now to FIGS. 3A-4 and 7A, the apparatus 600 for forming nested tufts in the modified web 335 may be the first unit operation 40, the second unit operation 50, or the third unit operation 60. The apparatus 600, aside from the cut and place operations 30 and 31, may be the only operation which provides the intimate contact between the topsheet web 10, the discrete portions 20A of the FM layer web 20, and/or discrete portions of absorbent core web 18. The process and equipment for making nested tufts as described herein is further described in U.S. Patent Application Publication Nos. 2016/0074256 and 2016/0074252A1.

Figure 8A:
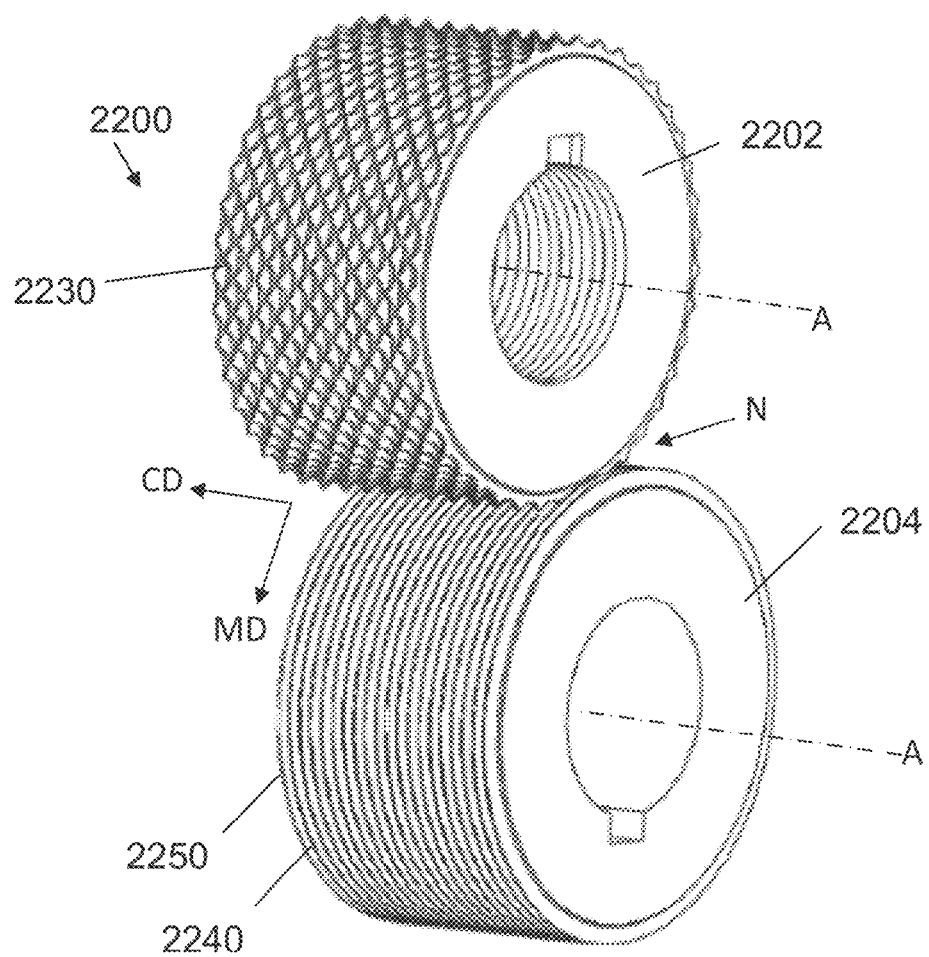
FIGS. 8A-8D are depictions of another pair of rolls or other elements which can create both apertures and protrusions in the topsheet and acquisition/distribution laminate web.
Figure 8B:
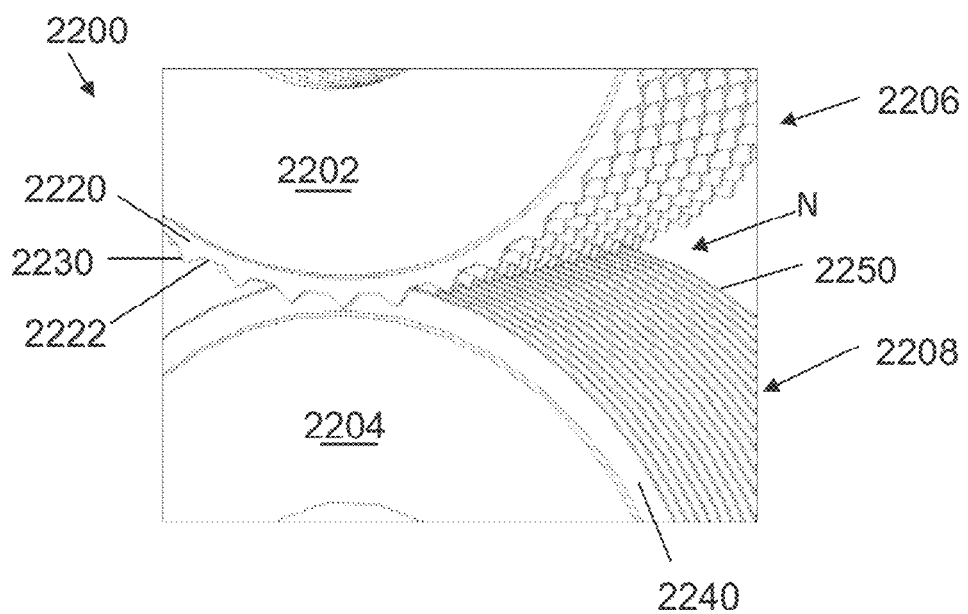
Figure 8C:
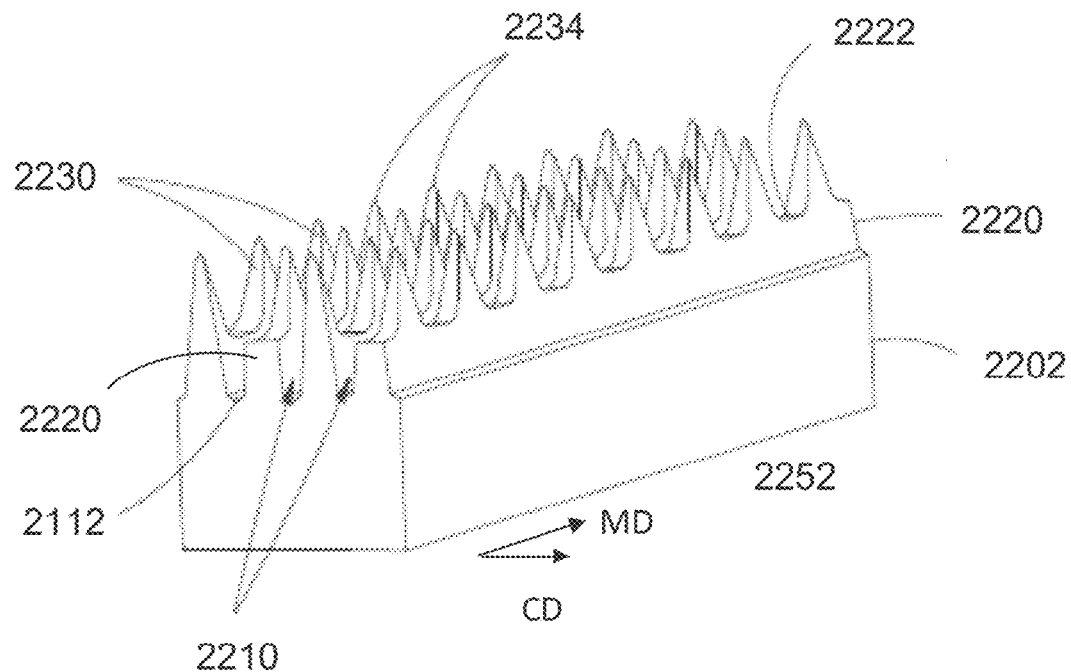
Figure 8D:
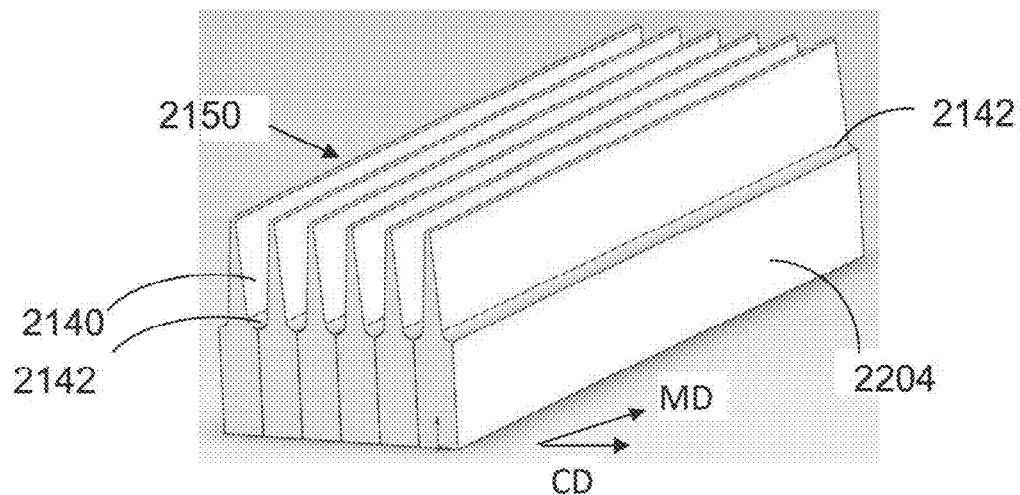

Other suitable protrusions which can be comprised by the modified webs 335 of the present disclosure comprises ridges and grooves or corrugations. Referring to FIGS. 8A-8D, an apparatus 2200 may be utilized to create corrugations in the precursor web. The apparatus 2200 comprises a single pair of counter-rotating, intermeshing rolls 2202, 2204 that form a single nip N therebetween. As shown in FIGS. 8A and 8B, the first roll 2202 comprises a plurality of grooves 2210 and ridges 2220 and a plurality of staggered, spaced-apart teeth 2230 extending outwardly from the top surface 2222 of the ridges 2220. The configuration of the roll 2202 is such that the top surface 2222 of the ridges 2220 is disposed between the tips 2234 of the teeth 2230 and the bottom surface 2212 of the grooves 2210, directionally relative to the axis A of the roll.

As shown, the second roll 2204 comprises a plurality of grooves 2240 and ridges 2250. The grooves 2240 have a bottom surface 2242 and the ridges 2250 have a top surface 2252. Here, the distance between the top surfaces 2252 of the ridges 2250 and the bottom surfaces 2242 of the grooves 2240 is substantially the same around the circumference of the roll. The teeth 2230 and ridges 2220 of the first roll 2202 extend toward the axis A of the second roll 2204, intermeshing to a depth beyond the top 2252 of at least some of the ridges 2250 on the second roll 2204.

Teeth suitable for this process may be conducive to aperturing webs. The teeth on the rolls may have any suitable configuration. A given tooth can have the same plan view length and width dimensions (such as a tooth with a circular or square shaped plan view). Alternatively, the tooth may have a length that is greater than its width (such as a tooth with a rectangular plan view), in which case, the tooth may have any suitable aspect ratio of its length to its width. Suitable configurations for the teeth include but are not limited to: teeth having a triangular-shaped side view; square or rectangular-shaped side view; columnar shaped; pyramid-shaped; teeth having plan view configurations including circular, oval, hour-glass shaped, star shaped, polygonal, and the like; and combinations thereof. Polygonal shapes include, but are not limited to rectangular, triangular, pentagonal, hexagonal, or trapezoidal. The side-walls of the teeth may taper at a constant angle from the base to the tip, or they may change angles. The teeth may taper towards a single point at the tooth tip, like that shown in FIG. 8A. The teeth can have tips that are rounded, flat or form a sharp point. In some forms, the tip of the tooth may form a sharp vertex with at least one of the vertical walls of the tooth (for example, the vertical walls on the leading and trailing ends of the teeth so the teeth aperture or puncture the web. In some forms, each tooth may form 2 apertures, one at the leading edge and one at the trailing edge of each tooth.

The apparatus 2200 can deform the precursor web creating alternating regions of higher and lower caliper, and alternating regions of higher and lower basis weight, with the higher caliper and higher basis weight regions being located in the tops of the ridges and bottoms of the grooves, and the regions with lower caliper and lower basis weight located in the sidewalls in-between. In the case of a nonwoven, the basis weight is also decreased in the stretched areas, again resulting in a modified web with alternating regions of higher and lower basis weight, with the higher basis weight regions located in the tops of the ridges and bottoms of the grooves, and the lower basis weight regions located in the sidewalls in-between.

Referring now to FIGS. 3A-4, and 8A, the apparatus 2200 for forming ridges and grooves in the precursor web may be the first unit operation 40, the second unit operation 50, or the third unit operation 60. The apparatus 2200, aside from the cut and place operations 30 and 31 may be the only operation which provides the intimate contact between the topsheet web 10, the discrete portions 20A of the FM layer web 20, and/or discrete portions of the absorbent core web 18.

Any suitable process for forming ridges and grooves may be utilized. Some additional processes for producing ridges and grooves in webs are described in additional detail in U.S. Pat. Nos. 6,458,447; 7,270,861; 8,502,013; 7,954,213; 7,625,363; 8,450,557; 7,741,235; U.S. Patent Application Publication Nos. US2003/018741; US2009/0240222; US2012/0045620; US20120141742; US20120196091; US20120321839; US20120321839; US2013/0022784; US2013/0017370; US2013/013732; US2013/0165883; US2013/0158497; US2013/0280481; US2013/0184665; US2013/0178815; US2013/0236700; PCT Patent Application Publication Nos. WO2008/156075; WO2010/055699; WO2011/125893; WO2012/137553; WO2013/018846; WO2013/047890; and WO2013/157365.

As noted previously, protrusions may be oriented in the positive Z-direction or the negative Z-direction. In the positive Z-direction, the protrusions may have some shape associated with them assuming that there is no constituent material surrounding the protrusion. However, when oriented in the negative Z-direction, these protrusions/depressions may simply take comprise sidewalls and a bottom without much for to them. Compressive forces of the surround constituent material can force cause these depressions to have very similar shapes when oriented in the negative Z-direction.

It is worth noting that the spunlace and needlepunch operations are typically primarily utilized to create integrity within a web. However, as discussed above, both the spunlace and needlepunch processes can also provide some level of intimate contact between adjacent layers. These processes operate in a micro-scale. In other words, they displace small amounts of constituent material in a plurality of locations on a web.

Comparatively speaking, without wishing to be bound by theory, it is believed that the operations which create conforming features can provide additional benefits above needlepunch and spunlace. Rather than operating on a micro-scale, processes for conforming features operate on a meso-scale. These meso-scale processes involve the displacement of a larger amount of constituent material. For example, needle punching may involve the displacement of 1 to 10 fibers whereas a meso-scale mechanical process may involve greater than 10 and up to 100 fibers or more. In contrast, the tooling for meso-scale processes described herein can have a length ranging from, as an example, about 3 mm to 11 mm. There are patterns which can utilize longer teeth and patterns which may utilize shorter. However, a length of about 1 mm is probably about as low as one would expect to see regrading meso-processing.

Accordingly, while spunlace and/or needle punching processes may be utilized, meso-scale mechanical processes may also be provided to the precursor web such that additional benefits are realized, e.g. conformance and/or resiliency. And, recall that meso-scale processes are different than embossing. While embossing provides a highly densified bottom surface where constituent material has been compressed, any densification in a bottom surface created by meso-scale processing is minor in comparison. Additionally, the conforming features made by meso-scale processes are generally visible to the naked eye from a reasonable distance, e.g. 30 cm, without the use of a microscope—assuming that the viewer has 20/20 or better corrected or uncorrected vision. Depending on the layers which are subjected to meso-scale processing, the topsheet and/or secondary topsheet may need to be removed from the article to see the conforming features. In contrast, micro-scale processes may require the assistance of a microscope to determine their existence. Some suitable examples of conforming features include protrusions, ridges, grooves, depressions, tufts, and the like.

Additional Process
Apertures

A suitable unit operation which provides some level of benefit in fluid management includes apertures. However, for the sake of the present disclosure, apertures are not considered to be conforming features. Referring to FIGS. 3A-3F and 9A-9B, the first unit operation 40 or the second unit operation may comprise an aperturing process. For example, the unit operations described herein may comprise a weakening roller arrangement 108 and an incremental stretching system 132. The precursor web 100 can pass through a nip 106 of the weakening roller (or overbonding) arrangement 108 formed by rollers 110 and 112, thereby weakening the precursor web 100 at a plurality of discrete, densified, weakened, areas thereby forming a weakened precursor web 100'. The weakened precursor web 100' has a pattern of overbonds, or densified and weakened areas, after passing through the nip 106. At least some of or all these overbonds are used to form apertures in the webs of the present disclosure. Therefore, the overbond pattern can correlate generally to the pattern of apertures created in the webs of the present disclosure.

Figure 9A:
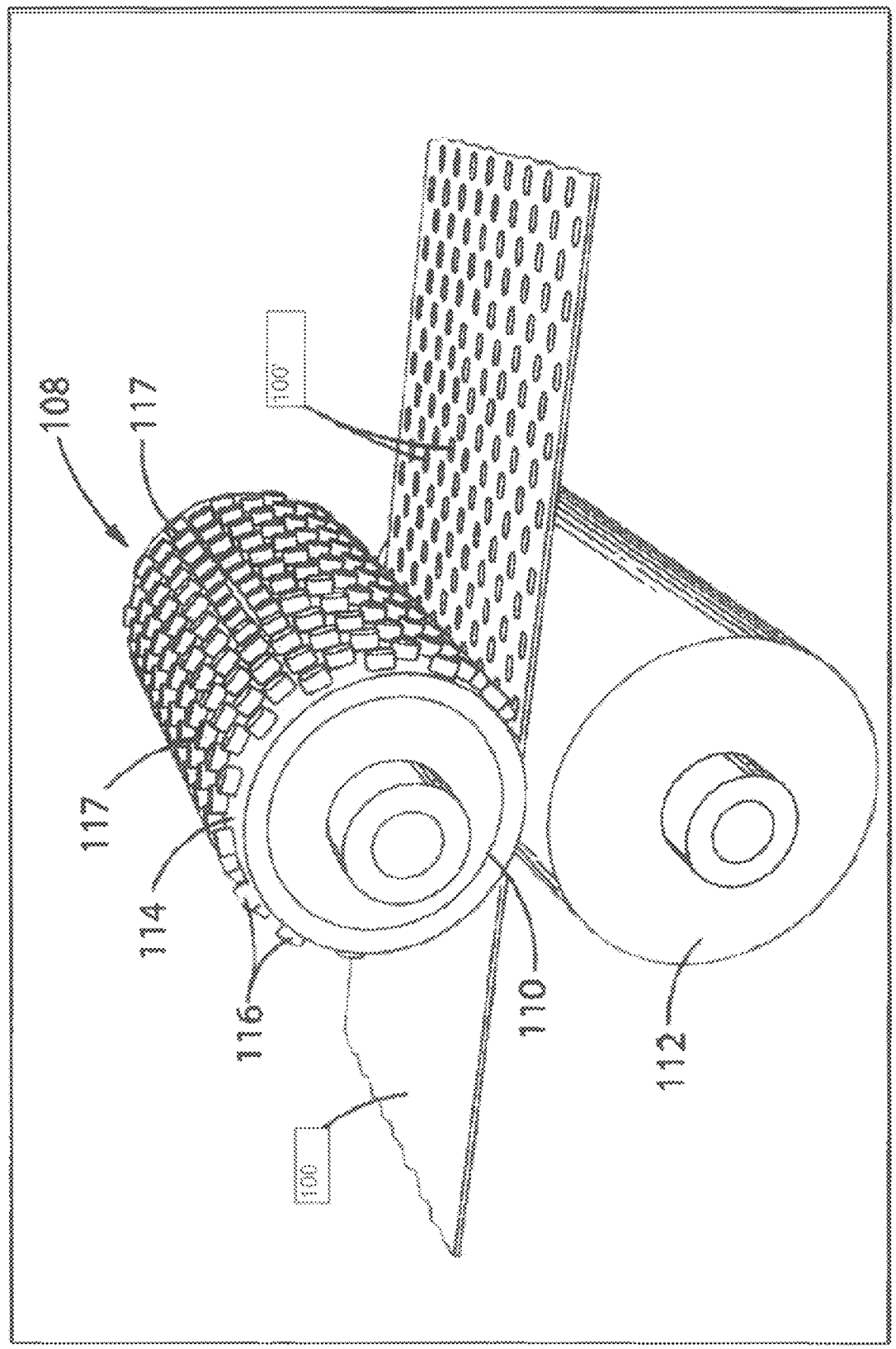
FIGS. 9A-9B are depictions of another pair of rolls which can create apertures the webs of the present disclosure.

Referring specifically to FIG. 9A, the weakening roller arrangement 108 may comprise a patterned calendar roller 110 and a smooth anvil roller 112. One or both the patterned calendar roller 110 and the smooth anvil roller 112 may be heated and the pressure between the two rollers may be adjusted to provide the desired temperature, if any, and pressure to concurrently weaken and melt-stabilize (i.e., overbond) the precursor web 100 at a plurality of locations 202. As will be discussed in further detail below, after the precursor web 100 passes through the weakening roller arrangement 108, the weakened precursor web 100' may be stretched in the CD, or generally in the CD, by a cross directional tensioning force to at least partially, or fully, rupture the plurality of weakened, melt stabilized locations 202.

The patterned calendar roller 110 is configured to have a cylindrical surface 114, and a plurality of protuberances or pattern elements 116 which extend outwardly from the cylindrical surface 114. The pattern elements 116 are illustrated as a simplified example of a patterned calendar roller 110, but more detailed patterned calendar rollers are contemplated and will be discussed hereafter. The protuberances 116 may be disposed in a predetermined pattern with each of the protuberances 116 being configured and disposed to precipitate a weakened, melt-stabilized location in the weakened precursor material 102 to affect a predetermined pattern of weakened, melt-stabilized locations 202. The protuberances 116 may have a one-to-one correspondence to the pattern of melt stabilized locations in the weakened precursor material 102. As shown in FIG. 9A, the patterned calendar roller 110 may have a repeating pattern of the protuberances 116 which extend about the entire circumference of surface 114. Alternatively, the protuberances 116 may extend around a portion, or portions of the circumference of the surface 114. Also, a single patterned calendar roller may have a plurality of patterns in various zones (i.e., first zone, first pattern, second zone, second pattern, etc.). The protuberances 116 may extend radially outwardly from surface 114 and have distal end surfaces 117. The anvil roller 112 may be a smooth surfaced, circular cylinder of steel, rubber or other material. The anvil roller 112 and the patterned calendar roller 110 may be switched in position (i.e., anvil on top) and achieve the same result.

Figure 9B:
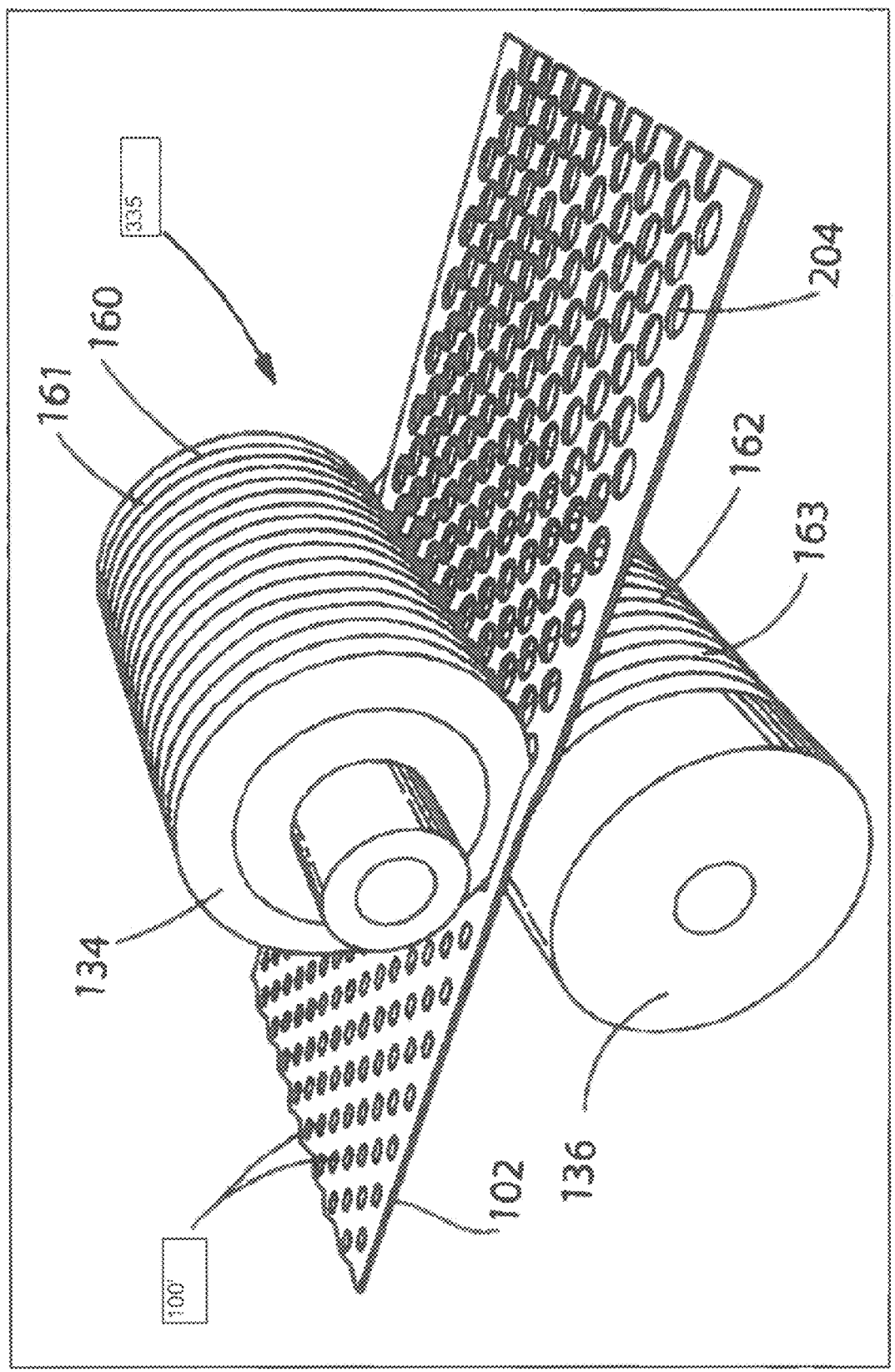

Referring to FIGS. 9A and 9B, from the weakening roller arrangement 108, the weakened precursor web 100' passes through a nip 130 formed by the incremental stretching system 132 employing opposed pressure applicators having three-dimensional surfaces which at least to a degree may be complementary to one another. After the weakened precursor web 100' passes through the nip 130, the weakened precursor web 100' becomes the modified web 335.

The incremental stretching system 132 comprises two incremental stretching rollers 134 and 136. The incremental stretching roller 134 may comprise a plurality of teeth 160 and corresponding grooves 161 which may about the entire circumference of roller 134. The incremental stretching roller 136 may comprise a plurality of teeth 162 and a plurality of corresponding grooves 163. The teeth 160 on the roller 134 may intermesh with or engage the grooves 163 on the roller 136 while the teeth 162 on the roller 136 may intermesh with or engage the grooves 161 on the roller 134. As the weakened precursor web 100' having weakened, melt-stabilized locations 202 passes through the incremental stretching system 132 the weakened precursor web 100' is subjected to tensioning in the CD causing the weakened precursor web 100' to be extended (or activated) in the CD, or generally in the CD. Additionally, the weakened precursor web 100' may be tensioned in the MD, or generally in the MD. The CD tensioning force placed on the weakened precursor web 100' is adjusted such that it causes the weakened, melt-stabilized locations 202 to at least partially, or fully, rupture thereby creating a plurality of partially formed, or formed apertures 204 coincident with the weakened melt-stabilized locations 202 in the modified web 335. The melt-stabilized locations 202 form melt lips defining the periphery of the apertures 204. However, the bonds of the weakened precursor web 100' (in the non-overbonded areas) may be strong enough such that many do not rupture during tensioning, thereby maintaining the weakened precursor web 100' in a coherent condition even as the weakened, melt-stabilized locations rupture. However, it may be desirable to have some of the bonds rupture during tensioning.

The apertures 204 may be any suitable size. For example, apertures 204 may have an Effective Aperture AREA in the range of about 0.1 mm$^2$ to about 15 mm$^2$, about 0.3 mm$^2$ to about 14 mm$^2$, about 0.4 mm$^2$ to about 12 mm$^2$, and about 1.0 mm$^2$ to about 5 mm$^2$, specifically including all 0.05 mm$^2$ increments within the specified ranges and all ranges formed therein or thereby. All Effective Aperture Areas are determined using the Aperture Test described herein. Effective Aperture Area is discussed in further detail in U.S. Patent Application Serial Nos. 2016/0167334; 2016/0278986; and 2016/0129661. Smaller apertures may be more aesthetically pleasing to users of absorbent articles; however, the smaller apertures can have a negative impact on fluid acquisition speed.

The process described regarding FIGS. 9A and 9B exemplify one suitable process for forming apertures. Some additional processes for aperturing webs are described in U.S. Pat. Nos. 8,679,391 and 8,158,043, and U.S. Patent Application Publication Nos. 2001/0024940 and 2012/0282436. Other methods for aperturing webs are provided in U.S. Pat. Nos. 3,566,726; 4,634,440; and 4,780,352. Additionally, the apertures may be provided to the modified webs of the present disclosure in patterns. Processes for forming aperture patterns and some suitable aperture patterns are disclosed in U.S. Patent Application Serial Nos. 2016/0167334; 2016/0278986; and 2016/0129661.

Zones

The unit operations described herein and features provided thereby, may be provided to an absorbent article in a zoned configuration. Zones are areas exhibiting one of either a visual pattern, a topography, an absorption rate or property, a bending parameter, a compression modulus, a resiliency, a stretch parameter or a combination thereof that is different than another portion of the absorbent article. The visual pattern may comprise any known geometric shape or pattern that is visual and can be conceived by the human mind. The topography may be any known pattern that is measurable and can be conceived by the human mind. Zones may be repeated or discrete. Zones may be orthogonal shapes and continuities that provide a visual appearance.

The use of zones allows for tailoring of the fluid handling and mechanical properties of and within the pad. The integrated absorbent structure may have one or more visual patterns including zones along one of either the longitudinal or lateral axis of the integrated layers. The integrated layers may have two or more zones comprising one or more visual patterns. The two or more zones may be separated by a boundary. The boundary may be a topographical boundary, a mechanical boundary, a visual boundary, a fluid handling property boundary, or a combination thereof, provided that the boundary is not a densification of the absorbent core structure. The boundary property may be distinct from the two zones adjacent to the boundary. The absorbent structure may have a perimeter boundary that exhibits a different property than the one or more adjacent zones to the boundary.

Figure 10:
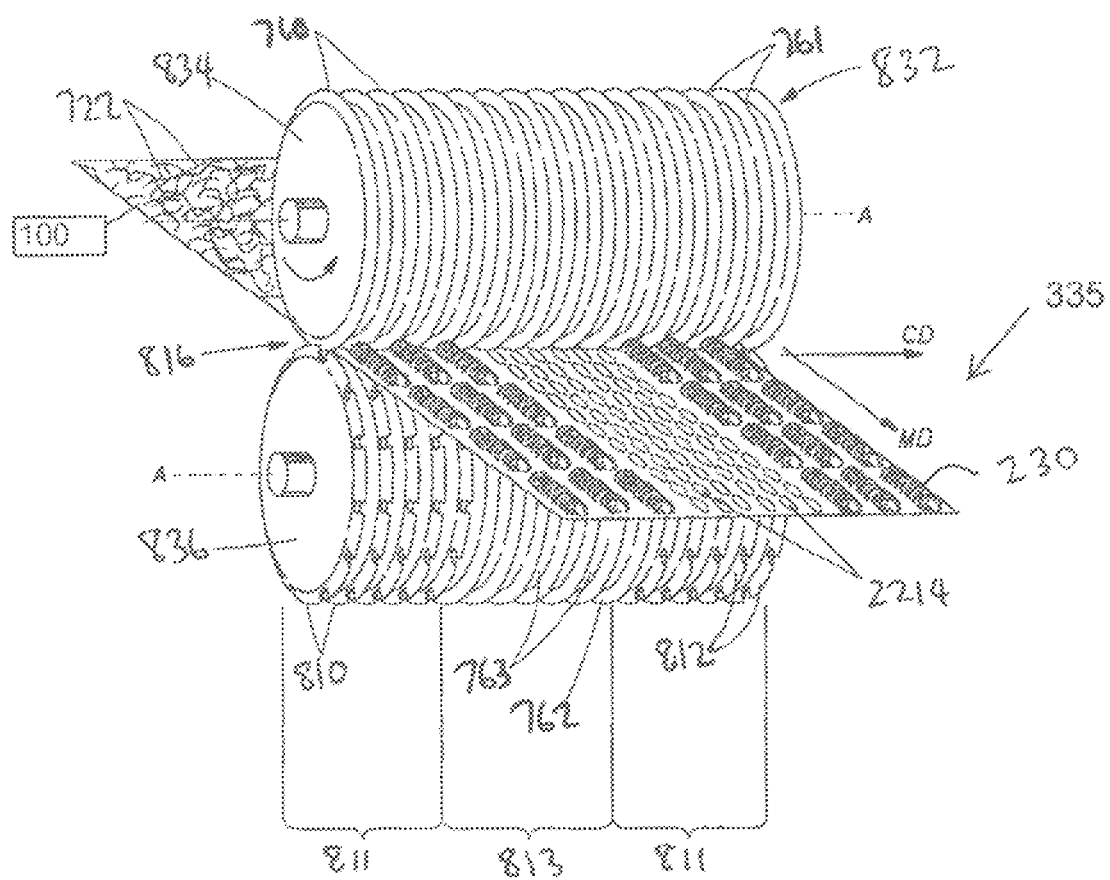
FIG. 10 is a depiction of an apparatus which can create apertures and protrusions in zones in the webs of the present disclosure.

One specific example of a process that can provide zoning is shown in FIG. 10. As shown, an incremental stretching system 832 may comprise rolls 834 and 836. As shown, the precursor web 100 may be provided with a plurality of melt stabilized locations 722 prior to entering nip 816. Recall that the melt stabilized locations 722 may be provided in zones on the weakened precursor web 100' (shown in FIGS. 9A and 9B). In the case of the incremental stretching system 832, the melt stabilized locations 722 may be provided in a central zone 813.

Upon stretching in the CD in the portion of the apparatus 832 corresponding to the region 813, the melt stabilized locations 722 rupture to form apertures. Again, the melt stabilized locations 722 may be limited to a central region of modified web 335. However, where melt stabilized locations 722 are provided throughout the precursor web 100, apertures 2214 may be created in region 813, while a combination of protrusions and apertures may be created in the regions 811.

As shown, the apparatus 832 comprises a pair of rolls 834 and 836, each rotating about parallel axes A. Roll 834 may be configured as described regarding roll 502 (shown in FIG. 6A). Namely, roll 834 may comprise a plurality of circumferentially-extending ridges 760 separated by grooves 761. A second, intermeshing roll 836 comprises the central region 813 having essentially matching roll 834 and having ridges 762 separated by grooves 763. The intermeshing ridges 760, 762 and grooves 761, 763 of rolls 834 and 836 incrementally stretch intermediate web 48 to form apertures 2214. In addition to region 813, roll 836 has two regions 811 comprising ridges having formed therein teeth 810, the toothed ridges separated by grooves 812. Ridges 760 of roll 834 intermesh with the grooves 812 of roll 836 to form the tufts as described herein. By combining both into one apparatus to form both apertures 2212 and tufts 230 in the precursor web 100.

The depth of engagement of the toothed ridges and the grooves can vary over the circumference of the rolls. Where that is the case, protrusions may be created which have varying heights and widths. For example, in a front region of an absorbent article, the depth of engagement may be less than the depth of engagement in the center of the article. The higher depth of engagement in the center may create protrusions which facilitate liquid acquisition of the absorbent article.

Modified webs 335 of the present disclosure may comprise a variety of zones. For example, modified webs 335 may comprise zones which provide increased conformity and fluid kinetics while other zones may provide a soft feel to the user along with increased structural integrity. And as noted previously, zones of an absorbent article may comprise a variety of layers of the absorbent article as well. So, one zone may comprise intimate contact features while another zone comprises conforming features, a combination of conforming features and intimate contact-features, different arrangements of conforming features, etc.

In one specific example, one or more zones may comprise apertures along with protrusions/depressions, e.g. tunnel tufts, filled tufts, nested tufts, or ridges and grooves. In one specific form, a first portion of protrusions (tunnel, filled, or nested) may be oriented in a positive Z-direction while a second portion are oriented in a negative Z-direction. In another specific form, one zone may comprise a combination of tunnel, filled, or nested tufts. In such forms, a first portion may be oriented in the positive Z-direction and a second portion may be oriented in the negative Z-direction. Or, forms are contemplated where at least one zone of a modified web 335 comprises both apertures and protrusions either in the positive and/or negative Z-direction.

Figure 11A:
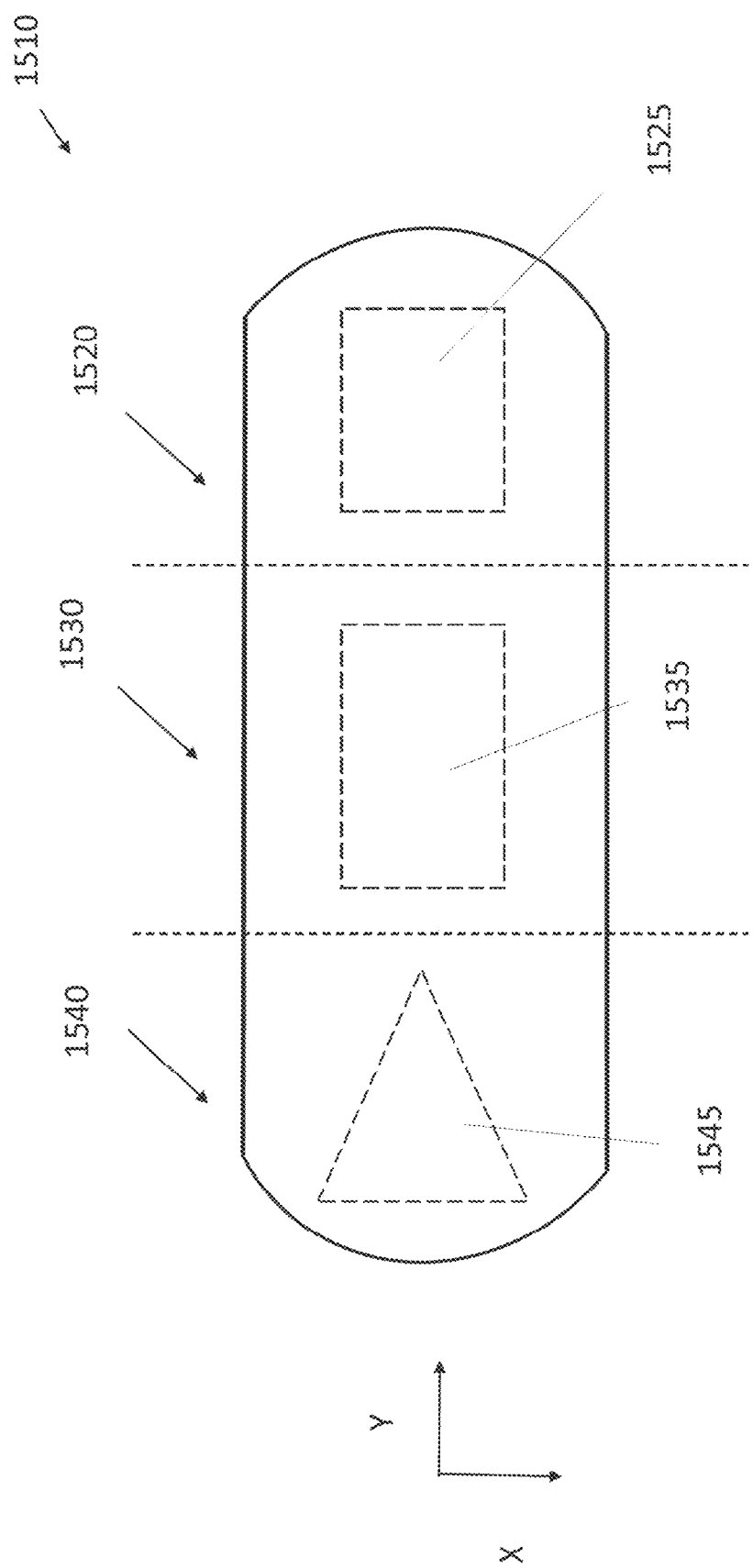
FIGS. 11A and 11B are schematic representations of absorbent articles comprising treated regions of the article.

Additional zone configurations are contemplated. For example, zones may be discretely positioned along a length of an absorbent article. An exemplary absorbent article 1510 is shown in FIG. 11A. The absorbent article 1510 is shown in the form of a feminine hygiene pad; however, the zones discussed herein may be applied to absorbent articles as desired. The absorbent article 1510 may comprise zones which extend laterally across the pad. For example, absorbent articles may comprise a first outer region 1520 disposed at one end of the absorbent article 1510 and an opposing second outer region 1540 disposed at an opposite end of the absorbent article 1510. Between the first outer region 1520 and the second outer region 1540 is a target region 1530. The dashed lines shown in FIG. 11A are imaginary and show exemplary delineations between adjacent regions.

The target region 1530, along with the first outer region 1520 and the second outer region 1540, may each comprise about one third the length of the absorbent article. Each of the above-mentioned regions may be processed differently to provide a different benefit for the user. For example, the first outer region 1520 may be associated with the front of the pad and may comprise a first zone 1525. The first zone 1525 may comprise protrusions which are smaller in scale compared to protrusions positioned outside of this area. The smaller scale protrusions may be provided to provide a soft, cushiony feeling to the wearer of the absorbent article 1510. As the front of the pad may be associated with the pubic symphysis area of the user, a softer, more-cushiony feel may be beneficial. Additionally, the first zone 1525 may be provided with a larger number of protrusions than the target zone 1535, vice versa, or they may have an equal number. And while the first zone 1525 is shown in the form of a rectangle, any suitable shape may be utilized. For example, the first zone 1525 may be in the form of a heart, a moon, a star, a horseshoe, a cloud, a flower, etc. In some forms, a plurality of discrete protrusions may form the aforementioned shapes. It is worth noting that the while the first zone 1525 is associated with the first outer region 1520, the first zone 1525 may not be necessarily limited to the first outer region 1520. Instead, the first zone 1525 may extend into the target region 1530 to some extent and/or into the second outer region 1540 to some extent. A target zone 1535 and a second zone 1545 may be similarly configured, e.g. they may extend into adjacent regions to some extent. Or the zones may extend the full length of the absorbent article.

As another example, the target region 1530 may comprise the target zone 1535. The target zone 1535 may correspond to the area of the absorbent article 1510 that is expected to receive liquid insults from the body. For example, in the context of a feminine hygiene pad, the target zone 1535 may disposed in the area of the article which corresponds to the vaginal opening in use. In the context of adult incontinence, the target zone 1535 may be disposed in the area of the article which corresponds to the urethral opening.

Because the target zone 1535 may receive the liquid insults from the body, the target zone 1535 may be processed such that liquid insults are quickly acquired and distributed to an absorbent core of the article. So, the target zone 1535 may be provided with apertures as described herein to allow for quick fluid acquisition. In some forms, the target zone 1535 may be provided with protrusions which are larger than those of the first zone 1525, which facilitate liquid acquisition. In some forms, the target zone 1535 may be provided with larger protrusions than what is provided in the first zone 1525 along with apertures. In some forms, the target zone 1535 may be provided with protrusions which are sized similar to the protrusions in the first zone 1525 along with apertures.

Much like the first zone 1525, the target zone 1535 is depicted in the shape of a rectangle; however, any suitable shape may be utilized. For example, the target zone 1535 may be in the form of a heart, a star, a horseshoe, a cloud, a flower, etc. Forms are contemplated where apertures present in the target zone 1535 are arranged in patterns. Suitable patterns and methods of making apertures in patterns were mentioned previously. Similarly, forms are contemplated where discrete protrusions in the target zone 1535 are arranged in patterns as noted via the target zone 1535 shape.

The target region 1530 and target zone 1535 of the absorbent article can play important roles in the functionality of the absorbent article. For example, the target region 1530 and target zone 1535 should provide a stable yet conformable center of the absorbent article which is close to the source of liquid insult. In some specific forms, the topsheet, the FM layer, and the absorbent core are mechanically manipulated to form intimate contact therebetween. In such forms, protrusions oriented in a negative Z-direction may be beneficial in improving acquisition speed and improving absorbency.

And, as another example, the second outer region 1540 may comprise a second zone 1545. The second zone 1545 may correspond to an area of the article that corresponds to the gluteal groove of the wearer. In such forms, it may be beneficial to specially process the second zone 1545 to allow the second zone 1545 to conform to the gluteal groove thereby allowing better fit of the article to the wearer. The second zone 1545 may be provided with protrusions which increase the flexibility of the second zone 1545 allowing the article 1510 to bend more easily than it would without protrusions. The second zone 1545 may be provided with conforming features as described herein which increases flexibility/conformability within the second zone 1545. In one specific example, the second zone 1545 may comprise protrusions oriented in the positive Z-direction which may provide assistance in wiping fluid from the body.

Typically, the most rigid portion of an absorbent article is an absorbent core which is disposed between a topsheet and a backsheet. Some conventional methods utilized to increase the flexibility of the core are to remove (cut-out) core material where additional flexibility is required. However, this can increase cost as absorbent core material is typically thrown away post removal. In contrast, in the case of the present disclosure, the absorbent core in the second zone 1545 may comprise conforming features which increase the flexibility of the absorbent core in the second zone 1545. In some forms, a topsheet and/or the FM layer, in addition to the absorbent core may comprise conforming features to increase flexibility in the second zone 1545. And while the second zone 1545 is shown as a triangle, much like the previous regions discussed, the second zone 1545 may comprise any suitable shape. Some examples include hearts, rainbows, stars, clouds, animals, etc. In some forms, the conforming features, etc. may be arranged in patterns in the aforementioned shapes.

Forms of the present disclosure are contemplated where the first zone 1525, the second zone 1545, and the target zone 1535 are processed similarly such that they each comprise conforming features. Such forms may eliminate the need for registration to some extent since all zones comprise the same size features. Forms are contemplated where the first zone 1525, the second zone 1545, and the target zone 1535 are processed similarly but include a variety of layers within their respective zones. For example, in some forms, the first zone 1525 and the second zone 1545 may comprise mechanical manipulation, e.g. conforming features, of the FM layer and the absorbent core, e.g. a first combination of layers. However, the target zone 1535 may comprise mechanical manipulation, e.g. conforming features, of the topsheet, the FM layer, and the absorbent core, e.g. a second combination of layers. Such a configuration may allow the absorbent article to be designed such that the first zone 1525 and the second zone 1545 may focus on comfort and fit of the absorbent article, while the target zone 1535 focuses on fluid acquisition and reduction of rewet. Or, zones may comprise intimate contact features and/or conforming features that are different. For example, the first zone and/or second zone may comprise a first plurality of intimate contact features and/or conforming features, and the target zone may comprise a second plurality of intimate contact features and/or conforming features, wherein the first plurality is different than the second plurality in at least one of shape, density (number per square cm), depth, length, shape, and/or spacing (nearest edge of feature to nearest edge of adjacent feature) between adjacent intimate contact and/or conforming features.

As noted previously, the shapes of the various zones within the regions may be configured as desired. For example, the zones may extend an entire width of the article in an X-direction. Regardless of the shape of the zones within the regions depicted in FIGS. 11A and 11B, a first distance 1570 of unmodified or differently modified material may be disposed between the first zone 1525 and the target zone 1535.

The determination of differently modified material and/or unmodified material may be determined via visual inspection of the materials similar to the identification of conforming features mentioned heretofore. Namely, unmodified material will not have been subjected to the meso-processing described herein. For the sake of clarity, unmodified material between adjacent zones, may have been subject to the micro-processing such as hydroentangling and needle punching. Additionally, differently modified material may have been subjected to meso-scale processes as described herein but may have conforming features that are different than the zones in which the differently modified material is adjacent.

Similarly, a second distance 1575 of unmodified material or differently modified material may be disposed between the target zone 1535 and the second zone 1545. In some forms, the first distance 1570 may be greater than the second distance 1575. The areas of unmodified material or differently modified material can help preserve the structure of the absorbent article 1510. This can ensure that the article 1510 maintains some structural integrity which encourages conformance by the article in the desired zones and provides crush resistance. In some forms, the first distance 1570 may be from about 5 mm to about 10 mm or more. In some forms, the second distance 1575 may similarly be from about 5 mm to about 10 mm or more. For example, the first and/or second distance may be between about 5 mm to about 30 mm, from about 7 mm to about 20 mm, or from about 9 mm to about 15 mm. The first distance and the second distance represent the shortest straight-line distance between the first zone and the target zone or the target zone and the second zone.

The zones discussed herein may be provided to the absorbent article 1510 in any suitable manner. For example, the article 1510 may comprise modified webs described herein and may be configured with zones as described above regarding FIGS. 11A and 11B. For example, the modified webs may comprise the first zone 1525, the second zone 1545, and the target zone 1535. Additional zone configurations are contemplated.

In addition to the zone configuration, based on the foregoing process description, there are many possible combinations which may be accomplished regarding zones on an absorbent article. A few of the possible combinations are discussed below along with the associated benefits. For example, forms are contemplated where the zones are provided uniformly through a plurality of layers, through only an individual layer, or through various combinations of layers. Specifically, at least one of the first zone 1525 or second zone 1545 may comprise intimate contact features and/or conforming features which are applied to at least two of the topsheet, the FM layer, or the absorbent core. The target zone 1535 may comprise intimate contact features and/or conforming features which are applied to at least two of the topsheet, the FM layer, or the absorbent core, wherein the layer combination of the target zone 1535 is different than that of the first zone 1525. Or the combination may be the same in these zones. Additional forms are contemplated which include additional material layers disposed between the topsheet and the backsheet. The additional material layers can be processed with one or more zones as described herein.

Referring now to FIGS. 3A, 3B, 3D, 11A, and 11B, in some examples, prior to any unit operation, the topsheet web 10 and the FM layer web 20 may be joined in the cut and place operation 30 thereby forming the TFM laminate 35. In such forms, any manipulation provided to the TFM laminate 35 is provided to both the topsheet and the FM layer. In such forms, the first unit operation 40 may impart to the TFM laminate features which correspond to the first zone 1525, the target zone 1535, and/or the second zone 1545. And, as noted previously, these features can help create intimate contact between the topsheet and the FM layer. For any of the zones where features are not provided, those zones may remain unmodified.

In contrast, in FIG. 3C the topsheet web 10 may be mechanically manipulated in the first unit operation 40 prior to being joined to the FM layer web 20 in the cut and place operation 30. The first unit operation 40 may provide to the topsheet web 10 features which correspond to the first zone 1525 and the target zone 1535. In conjunction or independent form the foregoing, the first unit operation may similarly provide conforming features which correspond to the second zone 1545. For any of the zones where features are not provided, those zones may remain unmodified.

The FM layer web 20 may be subjected to the first unit operation 40 prior to being joined to the topsheet web 10 in the cut and place operation 30. In such forms, the first unit operation 40 may provide to the FM layer web 20 features which correspond to the first zone 1525, the target zone 1535, and/or the second zone 1545. In such forms, the topsheet web 10 may be provided to the cut and place operation 30 unmodified. For any of the zones where features are not provided, those zones may remain unmodified.

In some forms, the topsheet web 10 and the FM layer web 20 may be subjected to separate unit operations prior to being joined in the cut and slip operation 30. The separate unit operations may impart features corresponding to the first zone 1525, the target zone 1535 and/or the second zone 1545, or any combination thereof to the topsheet web 10 and/or the FM layer web 20.

Figure 11B:
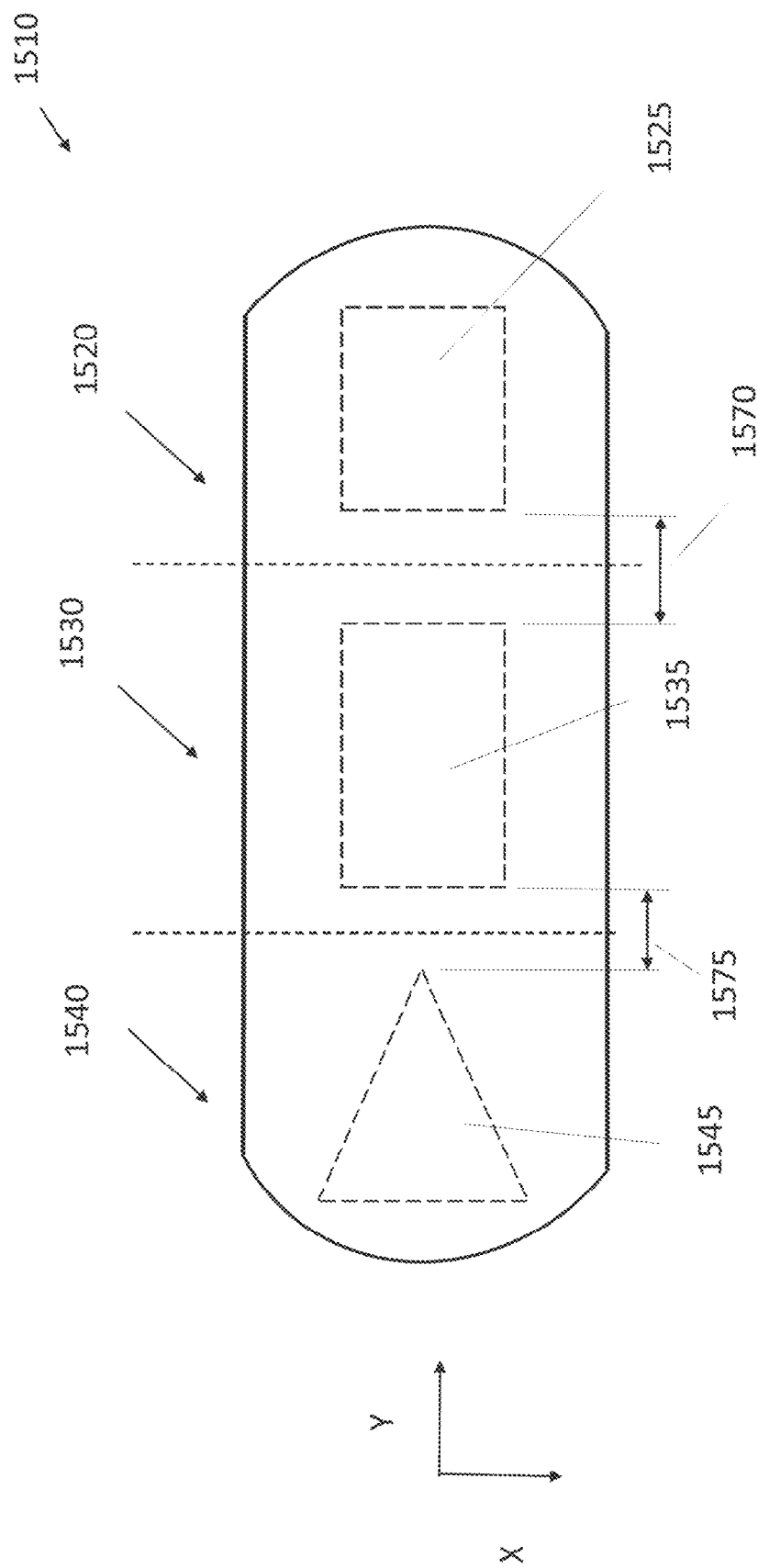

Regarding FIGS. 3D, 11A and 11B, in some forms, the absorbent core may be provided to the cut and place operation 31 along with the intermediate laminate 48. The resulting TFMAC laminate 37 may then be provided to the second unit operation 50. The second unit operation 50 may impart features to the TFMAC laminate 37 which correspond to the first zone 1525, the target zone 1535, and/or the second zone 1545. And, as noted previously, the features provided to the TFMAC laminate 37 can create intimate contact between the topsheet, FM layer and AC layer. For any of the zones where features are not provided, those zones may remain unmodified.

Regarding FIGS. 3E, 11A and 11B, in some forms, the FM layer web 20 and the absorbent core web 18 may be provided to a second unit operation 50 which imparts features to the FMAC laminate web 49. In such forms, the features provided to the FMAC laminate web 49 are provided to both the absorbent core web 18 and the FM layer web 20. In some forms, the second unit operation 50 may impart features as described herein which correspond to the first zone 1525, the target zone 1535 and/or the second zone 1545. As noted previously, as the absorbent core is typically the stiffest portion of an absorbent article, in some specific forms, the second unit operation 50 may impart conforming features, or the like to the FMAC laminate web 49 which correspond to the second zone 1545.

Forms are also contemplated where the absorbent core web 18 and the FM layer web 20 are subjected to separate unit operations. In such forms, features may be imparted to the FM layer which correspond to the first zone 1525, the target zone 1535, and/or the second zone 1545. Similarly, features may be provided to the absorbent core web 18 which correspond to the first zone 1525, the target zone 1535, and/or the second zone 1545. In some specific forms, the absorbent core web may be provided with conforming features in only the second zone 1545. Or, the absorbent core web may be provided with conforming features corresponding to zones which are different than that of the FM layer web 20.

Regarding FIGS. 3E, 3F, 9A, and 9B, the topsheet web 10 may be subjected to the first unit operation 40 in some forms or may be provided to the cut and place operation 30 un-modified. For those forms where the topsheet web 10 may be subjected to the first unit operation 40, features imparted to the topsheet web 10 may correspond to the first zone 1525, the target zone 1535, and/or the second zone 1545.

Figure 11C:
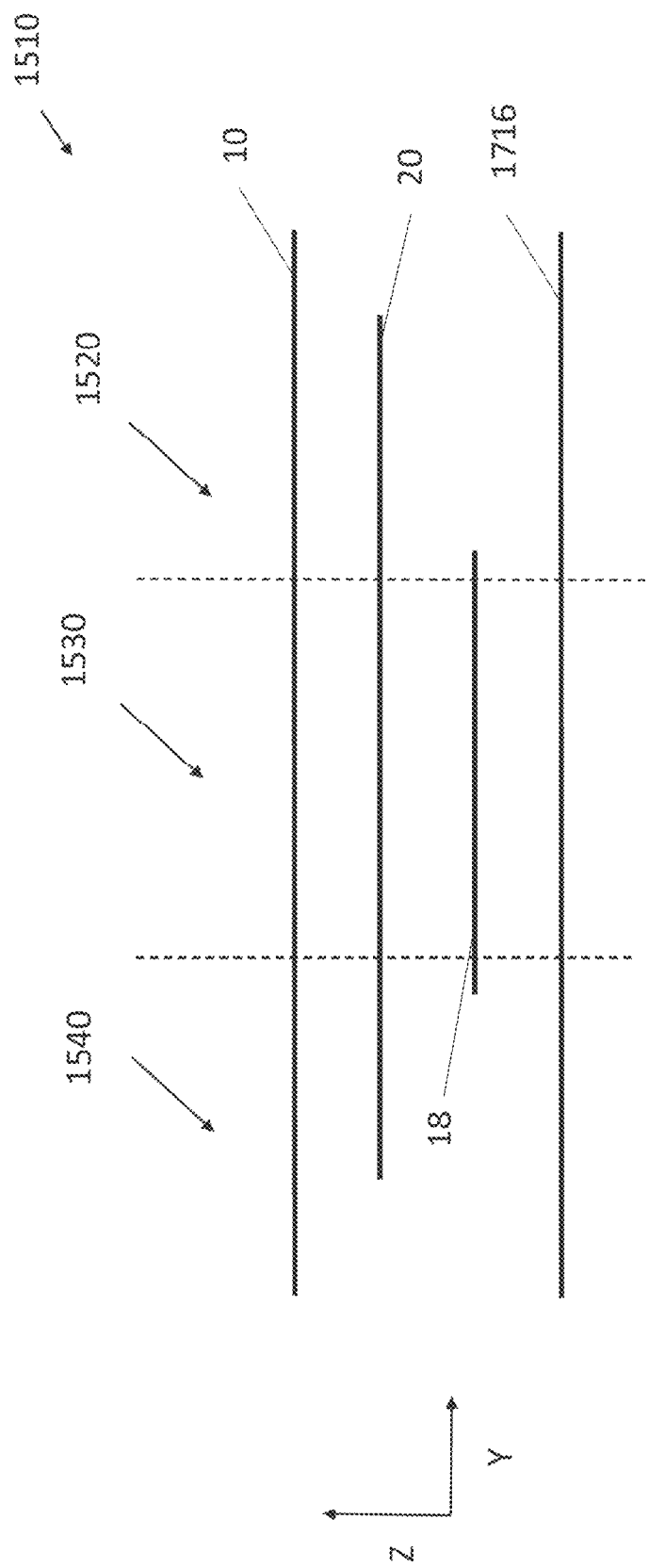

Zones may be further enhanced by creating non-coterminous materials. For example, forms are contemplated where the absorbent core web length is shorter than a length of the FM layer. Such constructions can reduce the amount of absorbent core web utilized per absorbent article. This can in turn save material cost. An example of a non-coterminous arrangement is shown in FIG. 11C. As shown, in some forms, the FM layer 20 and absorbent core layer 18 may be sandwiched between the topsheet web 10 and a backsheet web 1716. The FM layer 20 may have a length which is shorter than the topsheet 10 and the backsheet 1716 as mentioned previously. However, in some forms, the absorbent core 18 may have a shorter length than the FM layer 20. For example, as shown, the absorbent core 18 may be disposed in the target region 1530 and may extend only a slight amount into the first region 1520 and the second region 1540, e.g. less than 50% of the length of the first region and/or second region. In some forms, the absorbent core 18 may be disposed solely within the target region 1530. In such forms, the absence of the absorbent core 18 adjacent the ends of the absorbent article 1510 can allow much greater flexibility nearer the ends of the article 1510. Such forms may be accomplished via the cut and place operations described herein.

Additionally, in such forms, an additional material layer may be added to reduce the likelihood of leakage. For example, as shown in FIG. 11D, an auxiliary absorbent layer 19 can be added between the absorbent core 18 and the backsheet 1716. As shown, the auxiliary absorbent layer 19 can be primarily disposed in the second zone 1540 and overlap the absorbent core 18 in the target region 1530.

Figure 11E:
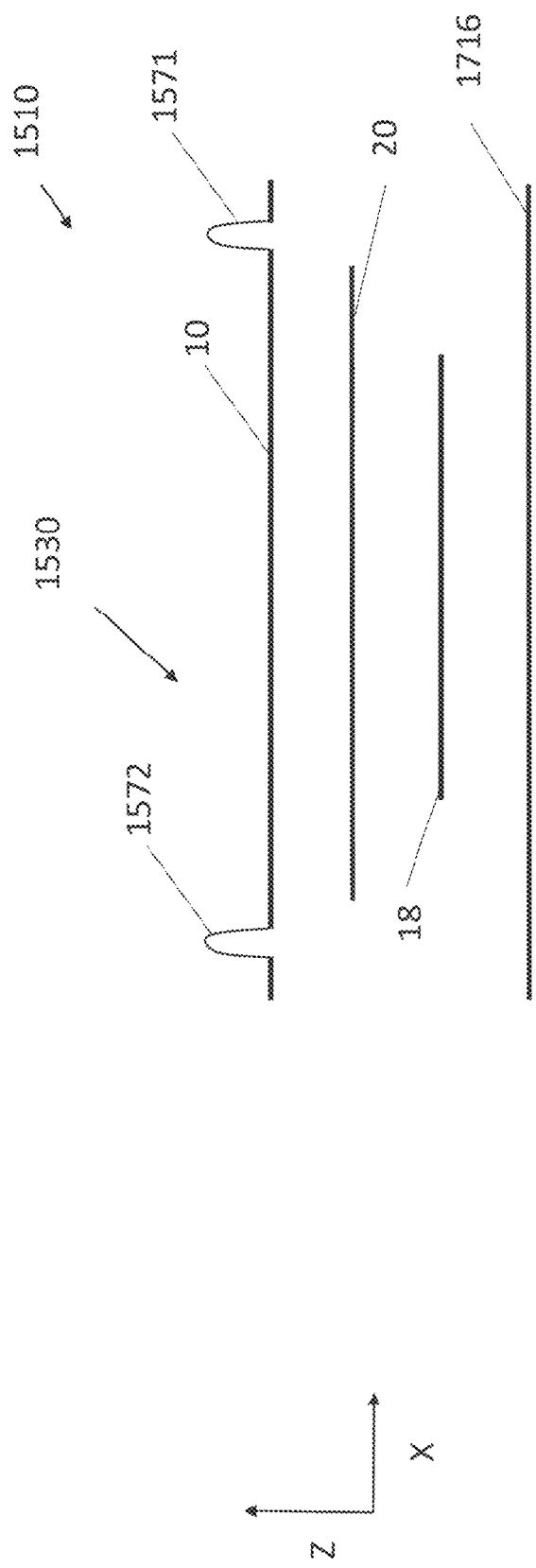

In one specific example, as shown in FIG. 11E, the absorbent article 1510 may comprise protrusions 1571 and 1572, each of which is disposed adjacent a longitudinal side edge of the absorbent article 1510. The protrusions 1571 and 1572 may be disposed only in the target region 1530. Or, in some forms, the protrusions 1571 and 1572 may be disposed along the entire length of its respective longitudinal side edge. In some forms, the protrusions 1571 and 1572 may comprise tufts as described herein, e.g. tunnel tufts, outer tufts, filled tufts, nested tufts, ridges and grooves, or may comprise corrugations as described herein. For those forms, where the protrusions 1571 and 1572 comprise tufts, a plurality of tufts may be arranged longitudinally adjacent the length of the longitudinal side edges of the absorbent article 1510. For those forms comprising corrugations, a plurality of ridges and grooves may similarly be arranged longitudinally along the longitudinal side edges of the absorbent article 1510. Or in some forms, a single ridge and groove and may be arranged longitudinally along the length of the longitudinal side edges.

The forms incorporating the protrusions 1571 and 1572 may provide additional leakage protection by acting as barriers. Additional configurations are contemplated. For example, absorbent articles of the present disclosure may comprise a plurality of rows of protrusions which are laterally spaced apart from one another. Such configurations can provide barriers to leakage and can also provide a softness benefit to the user. In some forms, the protrusions 1571 and 1572 may be formed in the topsheet of the absorbent article. In other forms, the protrusions 1571 and 1572 may be formed in the topsheet and the absorbent core or the topsheet and the FM layer. For these forms, the protrusions 1571 and 1572 can be absorbent to some extent.

Forms are contemplated where the first region, the target region, and/or the second region comprise more than one zone. For example, regarding the form shown in FIG. 11E, the target region may comprise an outer zone in which the protrusions 1571 and 1572 are disposed. The outer zone may be disposed outboard of the target zone. And for those forms where the first region and/or the second region comprises protrusions, the protrusions may be disposed in outer zones which are outboard of the first zone and/or the second zone, respectively.

In addition to the mechanical manipulation described heretofore and the creation of zones, forms of the present disclosure are contemplated where in addition to the intimate contact via mechanical manipulation described herein, zones may be created or enhanced via chemical heterogeneity. For example, where protrusions are provided in an absorbent article, the distal ends of the protrusions may be provided with a composition. Or land areas between adjacent protrusions may be provided with compositions. In one specific example, where protrusions are oriented in a positive Z-direction, distal ends of the protrusions may be provided with a hydrophobic composition. In another specific example, where the protrusions are oriented in a negative Z-direction, distal ends of the protrusions may be provided with a hydrophilic composition. Suitable compositions and methods for applying compositions to webs are described in additional detail in U.S. Patent Application Publication Nos. 2017/0225449A1; 2017/01202601; and 2017/0258650A1.

Conforming Modified Webs

The inventors have surprisingly found that intimate contact, while beneficial for fluid management, may not be sufficient—on its own—for product conformity. For example, needlepunched and spunlaced modified webs, while providing intimate contact between adjacent layers and therefore good fluid handling properties, cannot provide the level of conformity required on their own. Rather, the meso-scale processes as described herein may be utilized with appropriate spacing, as discussed herein, to form conforming features in the modified webs.

The absorbent articles of the present disclosure may provide good conformity to the body of the wearer in addition to the good fluid management. However, while good fluid management may be derived from intimate contact, which can be created via the micro-scale processes and the meso-scale processes, good conformance can only be achieved via meso-scale processes or a combination of micro-scale and meso-scale processes as described herein.

Traditional fibrous absorbent core materials such as thick (or densified cellulose fluff) or absorbent airlaid materials are mostly composed of short (~2.5 mm) cellulose fibers that form inherently weak mechanical structures. These conventional structures struggle to maintain their integrity and shape during dynamic bodily motions in the dry state. And, in the wet state, integrity and product sustaining shape only deteriorates further as cellulose fibers wet plasticize and become soft, pliable and collapse. Historically two approaches have been employed to improve the mechanical performance of cellulosic systems; densification (typical fluff cores range from un-densified 0.04 g/cm$^3$ to about 0.2 g/cm$^3$ when densified), and in the case of airlaid's, the inclusion of heat bondable bi-component fibers (typically less than 6 mm in length) or latex based binders in addition to densification (airlaid's are typically in the 0.08-0.15 g/cm$^3$).

The problem of densification of cellulosic short fiber absorbent core systems is that these tend to significantly stiffen the absorbent core system. Unfortunately, the densification can have a negative impact on both comfort and the ability of the stiffened absorbent system to conform to the intimate body shape. The intimate area is characterized by significant topographic variations on a relatively short (sub centimeter) length scale. This complex geometry can be difficult to conform to due to the densification. Namely, as absorbent systems are densified, their bending modulus (ease of bending) and bending stiffness dramatically increase making intimate conformation to the labial (major and protruding minora) surfaces very difficult. And as noted, these short fiber cellulosic fiber structures significantly collapse in the dry to wet state.

The ability of an absorbent article to conform during use is generally governed by the stiffest layer within the absorbent article. To create an absorbent article which can provide good conformance to the body of a wearer, the stiffest layer of the absorbent article should be mechanically manipulated as described herein to create a more conforming structure. In some forms, this may comprise mechanical manipulation of the topsheet, optional FM layer, and absorbent core either across the entirety of the absorbent article or in zones as described herein. As noted previously, such manipulation of these layers may occur throughout the absorbent article or in zones as discussed herein. And, along with the benefit of increased conformity, the benefit of intimate contact and therefore good fluid management can also be realized.

For FIGS. 12A-12B and 13A-13C, a pattern of struts, nodes and depressions are shown. The nodes are interconnected to one another via struts which are spaced apart from one another via depressions. The nodes are essentially unmodified material of the modified web while the material associated with the struts and depressions is mechanically strained. There may be at least one strut that connects an adjacent node. Or, there may exist a plurality of struts between adjacent nodes. For example, the number of struts may be between about 2 to about 10. Or, more than 10 struts may be utilized.

Figure 12A:
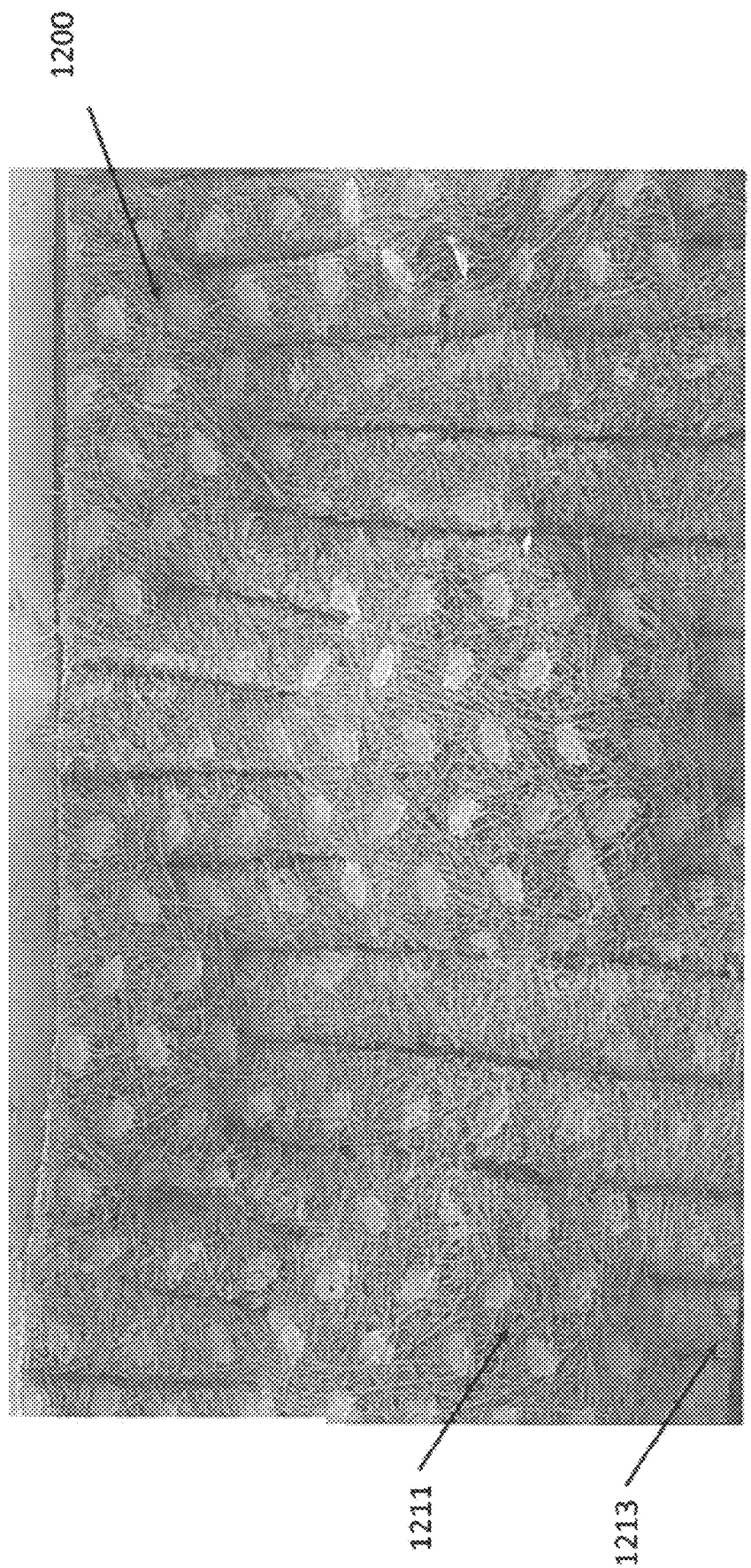
FIG. 12A is a photo showing a plan view of a web constructed in accordance with the present disclosure.
Figure 12B:
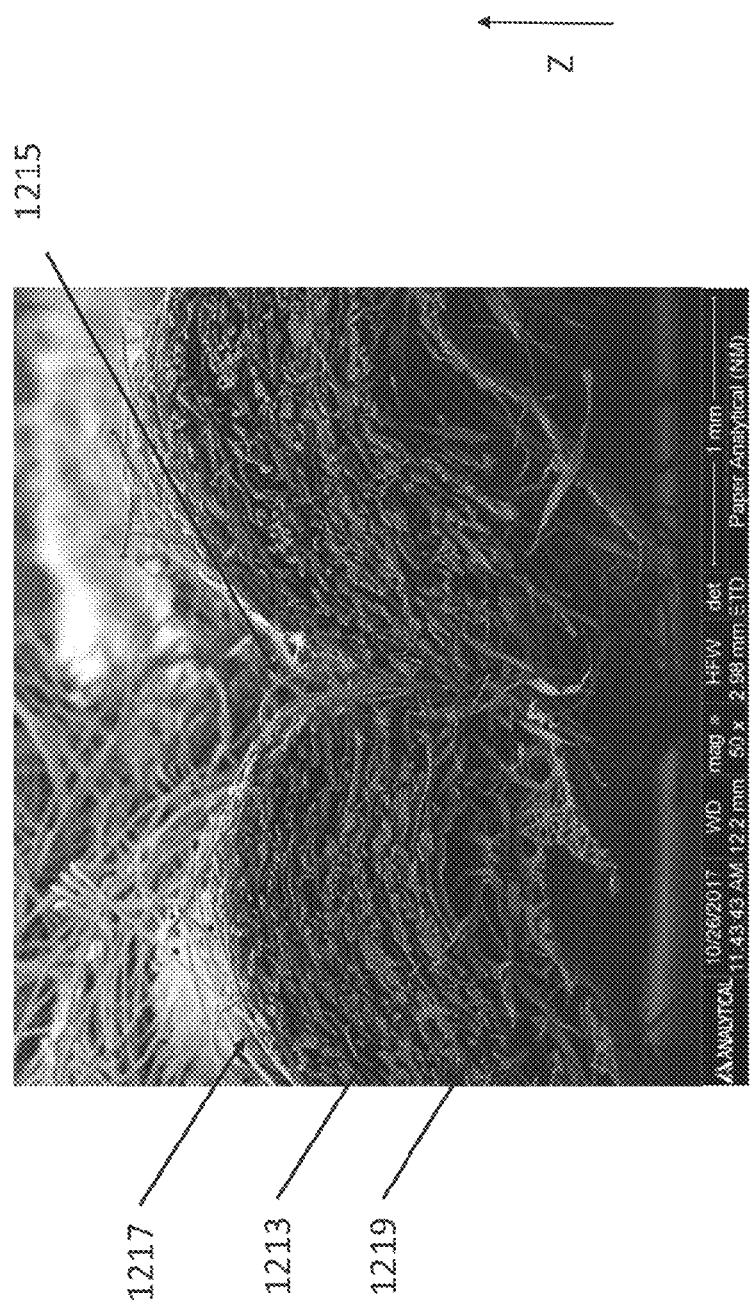
FIG. 12B is a photo showing a cross section of the web of FIG. 12A.

FIGS. 12A to 12B show a plan view of and a cross-sectional view, respectively, of a topsheet integrated with an absorbent core utilizing the tufting process described herein. The tufts were oriented in the negative Z-direction. As shown, a topsheet 1217 and absorbent core 1219 composite 1200 that not only provides good fluid management benefits but also provide good conformance to the body, comprises a plurality of nodes 1211 and a plurality of struts 1213 between adjacent nodes. Between adjacent struts 1213 are depressions 1215 which extend in a negative Z-direction. The depressions 1215 can be formed when the tooling described—see for example FIG. 6B regarding the protrusions herein—impacts the topsheet and absorbent core web. As shown fibers of the topsheet 1217 along with fibers of the absorbent core 1219 are disposed within the depressions 1215.

The sample of FIGS. 12A-12B comprised a 28 gsm calendar bonded, bi-component, spunbond fiber topsheet 1217. The absorbent core 1219 was coformed comprising 30 percent continuous, e.g. longer than staple fiber, about 5 to about 10 microns, or larger, polypropylene fibers. The tooling that created the depressions 1215 was as described regarding tufts. The DOE of the tooling was 1.9 mm.

Figure 13A:
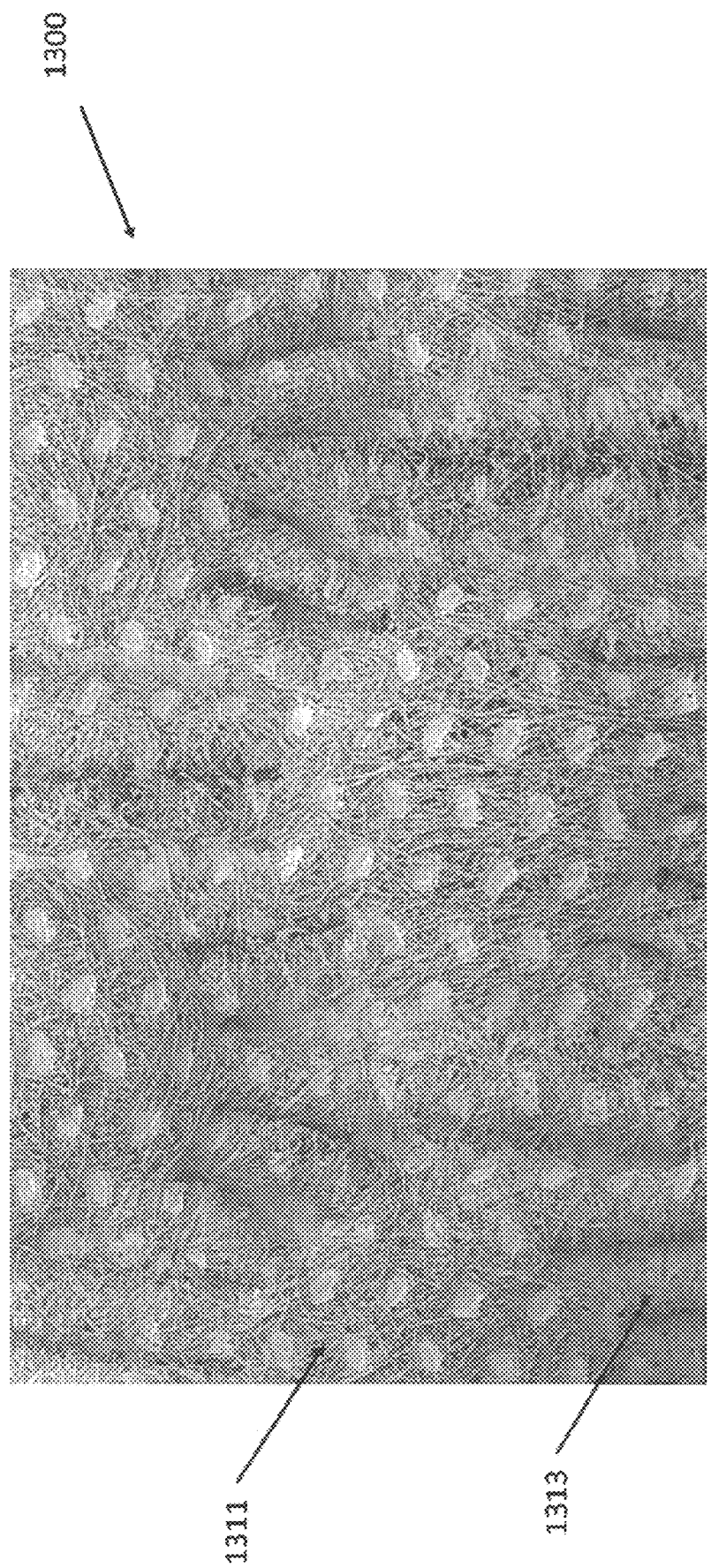
FIG. 13A is a photo showing a plan view of another web constructed in accordance with the present disclosure.
Figure 13B:
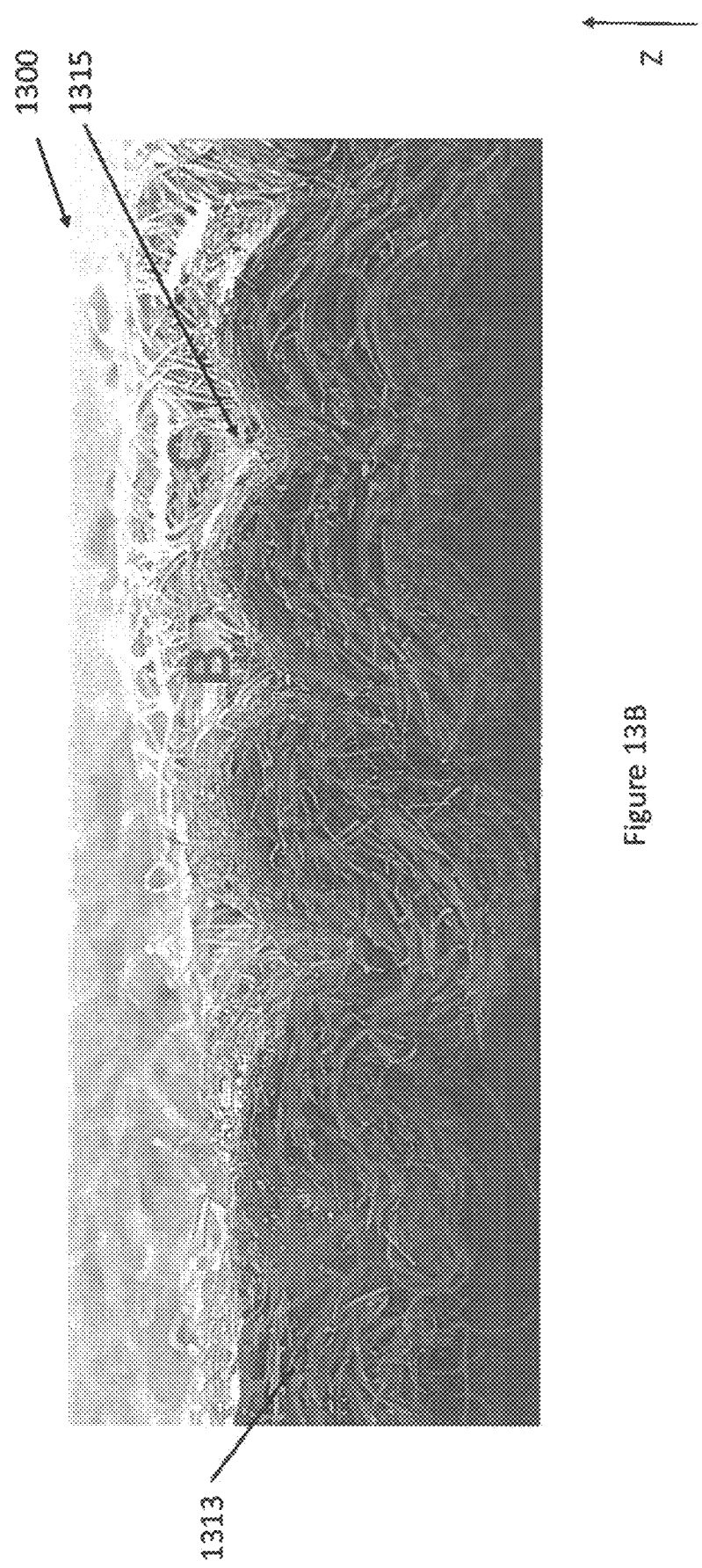
FIGS. 13B and 13C are photos showing a cross section of the web of FIG. 13A.
Figure 13C:
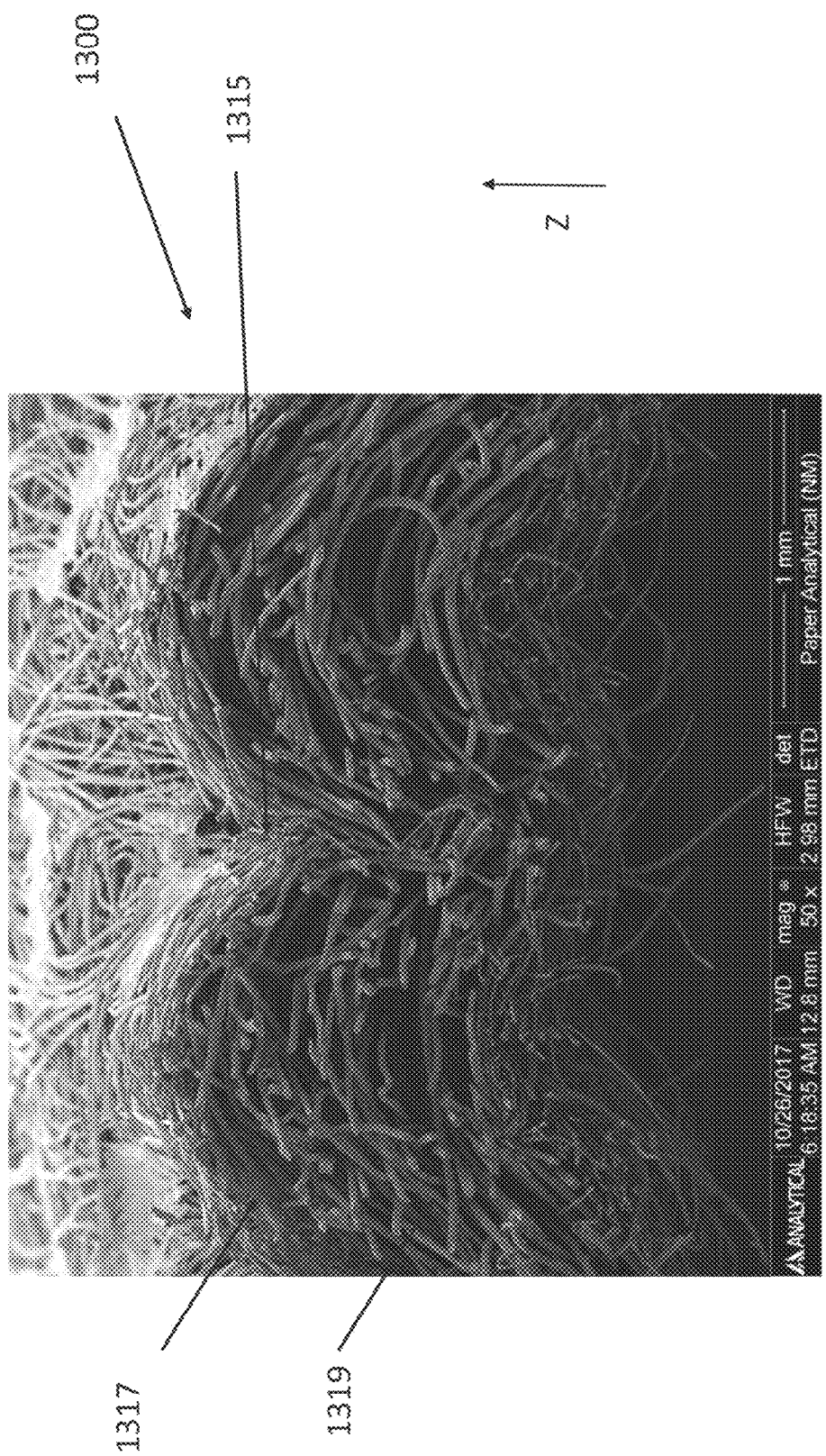

FIGS. 13A-13C show a plan view of and cross-sectional views, respectively, of a topsheet 1317 integrated with an absorbent core 1319. The tufts were oriented in the negative Z-direction. As shown, a composite web 1300 of the topsheet 1317 and absorbent core 1319 comprises nodes 1311 and struts 1313. Between adjacent struts 1313 are depressions 1315 which extend in the negative Z-direction. The depressions 1315 can be formed when the tooling described regarding protrusions herein, impacts the topsheet and absorbent core web. As shown fibers of the topsheet 1317 along with fibers of the absorbent core 1319 are disposed within the depressions 1315. The sample of FIGS. 13A-13C comprised a 28 gsm calendar bonded, bi-component spunbond fiber topsheet 1317. The absorbent core 1219 was a hydroentangled nonwoven with 38 mm fiber lengths. The tooling that created the depressions 1215 was as described with regard to tunnel tufts. The DOE of the tooling was 1.9 mm.

For both samples of FIGS. 12A-12B and 13A-13C, it is worth noting that the topsheet is displaced down into and between adjacent struts. As noted previously, micro-scale processing of the same, e.g. needlepunch or spunlace would only displace a few fibers of the topsheet within each depression. In contrast, the meso-scale processing described herein displaces a much larger amount of the constituent material of the topsheet into the absorbent core which can allow the resulting features to provide absorbent article conformance benefits. Further, via the meso-scale processing, the topsheet and absorbent core are in intimate contact with each other to provide good fluid management characteristics.

FIG. 14 shows a schematic close up cross section showing a topsheet and an absorbent core composite 1400. As shown the depressions 1415 (exaggerated for ease of visualization) do not extend through the thickness of the composite, but rather rearrange constituent material of the topsheet and/or absorbent core. So in other words, the depressions have a bottom 1421. As shown, the depression bottoms 1421 may be disposed between a first surface and a second surface of the composite 1400. Or, the bottom 1421 of at least one depression may be disposed subjacent to the second layer of the composite 1400. When the teeth of the rolls described in, for example, FIG. 6A or 6B engage the constituent material of the topsheet and/or absorbent core, some of the constituent material may extend, thin, and some may even break. In the case of nonwoven materials, fibers of the nonwoven may become thinner and some fibers may break. Similarly, in the absorbent core, some of the constituent material may break or become unattached to the constituent material of the absorbent core. So, the depressions 1415, in a sense form a weakened area between adjacent struts 1413. The weakened area, due to the reduced amount of material, can allow the struts 1413 to move, bend, and/or rotate somewhat independently from one another. However, the bottom 1421 ties adjacent struts 1413 together such that the absorbent core still retains some structural significance.

In addition to tying adjacent struts 1413 together, the bottoms 1421 also form a bridge between adjacent struts 1413. This bridge can serve as a fluid transport pathway which can help utilize more of the material of the absorbent core as opposed to where a bridge is absent.

Additionally, it is believed that with the urging of the material of the topsheet and absorbent core in a negative Z-direction, that material of the topsheet and absorbent core mix to some extent along the side walls of the depressions and in the bottoms of the depressions. As such, the depressions can provide a fluid management benefit via faster fluid acquisition. In contrast, while embossing may provide some mixing of material between the topsheet and the absorbent core, the densification of the area formed by embossing does not increase fluid acquisition speed in the densified areas.

Each of the depressions 1415 has a length which extends generally parallel to its long axis. As shown in the FIGS. 12A-12C and 13A-13C, the lengths of the depressions can vary. As shown, the long axis may be generally oriented in a direction which is parallel to a longitudinal axis of an absorbent article. However, the depressions 1415 can have a long axis which is generally parallel to a transverse axis of an absorbent article. The depressions 1415 may have a long axis which is at an angle with respect to the longitudinal axis of the absorbent article. For example, a first portion of depressions 1415 may have a long axis which is generally parallel to the longitudinal axis, and a second portion of depressions 1415 may have a long axis which is generally parallel to the transverse axis. A third portion of depressions 1415 may have a long axis which is generally at an angle with respect to the longitudinal axis. The depressions 1415 of the third portion may comprise depressions having a long axis which are at a variety of angles with respect to the longitudinal axis. As an example, a portion of the depressions 1415 may have a long axis which is at a first angle with respect to the MD, and a portion of depressions 1415 may have a long axis which is at a second angle with respect to the MD. A portion of the depressions' long axis may be at a third angle, and a portion of the depressions' long axis may be at a fourth angle, etc.

The spacing between adjacent depressions—generally perpendicular to the long axis of the depression—can be any suitable distance and depend on the spacing of the forming elements on the associated rolls. As there may be mechanical limits regarding the rolls regarding spacing, such limits may then impact the spacing between adjacent depressions. Additionally, the caliper of the layers being integrated may drive spacing between depressions as well. For example, thicker caliper materials may require a higher spacing between adjacent teeth. Closer spacing between teeth, depending on the materials being integrated, can cause shredding/tearing of the layers. In some specific forms, the depressions may be spaced apart by greater than about 1 mm in the CD and greater than about 2 mm in the MD.

In some forms, the bottoms 1421 may be bonded via heated teeth or other suitable mechanism. The bonded bottoms 1421 can provide additional stability to the web and ensure that the topsheet is firmly anchored to the absorbent core. A suitable process is described in additional detail in U.S. Pat. No. 7,682,686.

Even though the composites described regarding FIGS. 12A-12B and 13A-13C comprise topsheets and absorbent cores, topsheet and FM layer composites may be formed. Or, composites may comprise an FM layer and absorbent core. Or, composites may comprise a topsheet, FM layer, and absorbent core.

Figure 15A:
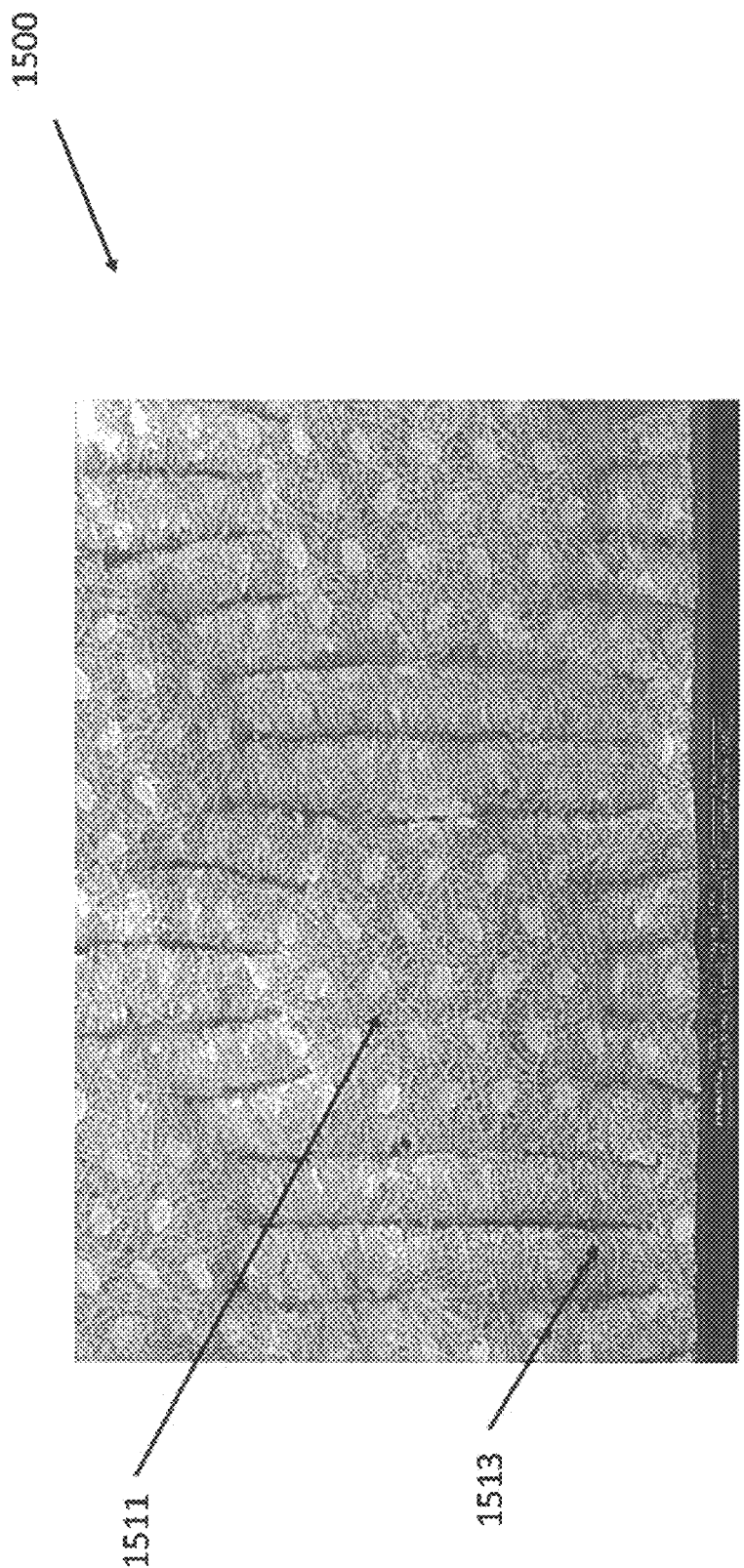
FIG. 15A is a photo showing a plan view of a web constructed from materials which lack a long fiber network of the present disclosure.
Figure 15B:
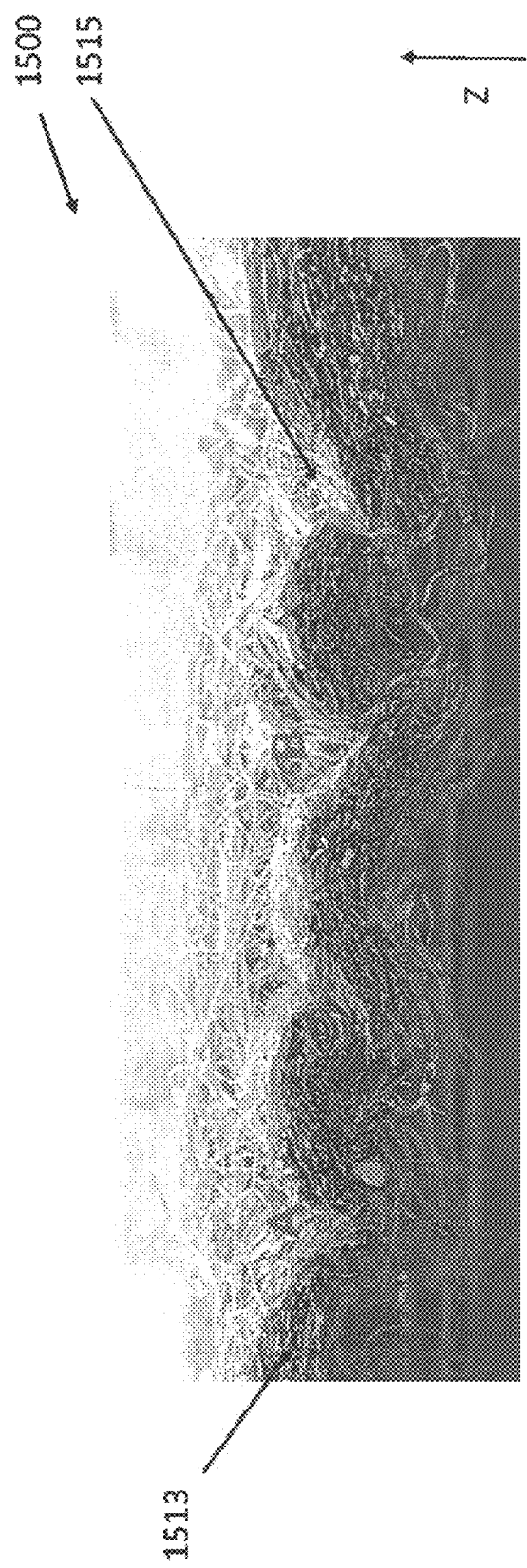
FIGS. 15B and 15C are photos showing cross sections of the web of FIG. 15A.
Figure 15C:
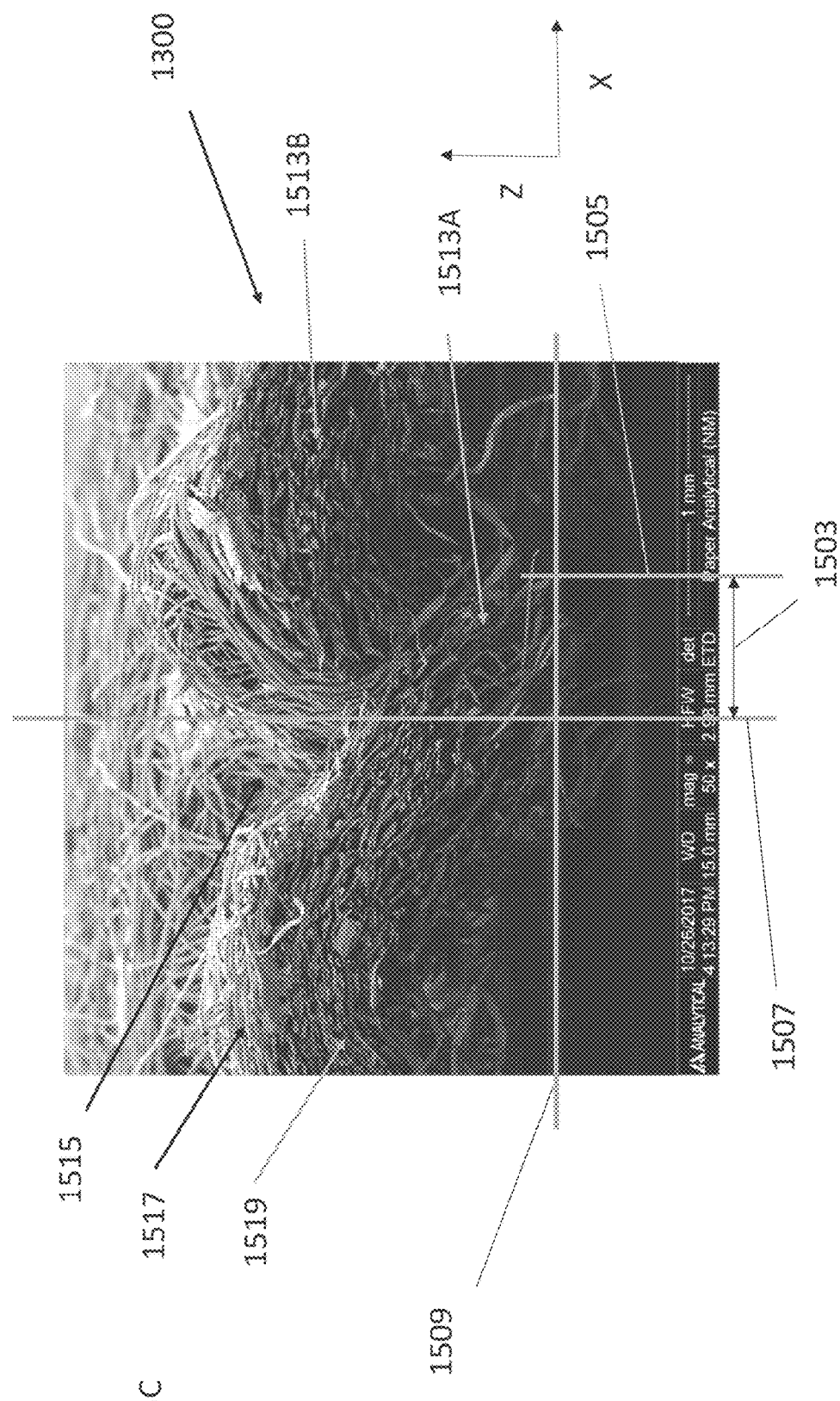

As noted previously, some cellulose based materials, when exposed to the meso-scale processes as described herein, may be torn, ripped, and/or shredded to some extent. An example of what happens to some materials when subjected to the meso-scale processes described herein is shown in FIGS. 15A-15C. As shown, from a plan view in FIG. 15A, the topsheet and absorbent core composite 1500 does not appear all that different from the composites 1200 and 1300 (shown in FIGS. 12A-12B and 13A-13C, respectively). The composite 1500 comprises a node 1511 and a plurality of struts 1513A and 1513B. Each strut forms a sidewall portion of the depression 1515 opposite one another. However, as shown in FIGS. 15B and 15C though, a depression 1515 extends all the way through the composite 1500 and acts like a slit between adjacent struts. From a mechanical standpoint, the depression 1515 can allow the struts 1513A and 1513B to move relative to one another without any tie connection to the adjacent struts. This can allow for great conformance initially. However as shown, without the connection between adjacent struts as described regarding FIG. 14 (present in FIGS. 12A-12B and 13A-13C), the struts 1513 can have too much flexibility in the degree of movement available. For example, as shown a portion of a first strut 1513A is disposed beneath a portion of a second strut 1513B. So, any movement of the absorbent core requires sufficient energy to overcome the sliding of the struts 1513A and 1513B over one another. And rather than being stored as potential energy within the core, the energy of the movement is dissipated in overcoming the relative movement of the struts one over the other—similar to friction loss. Because of the lost energy, once deformed, without the connected areas described in FIG. 14, the struts 1513A and 1513B may not have the requisite energy to recover to their undeformed state. And as such, the composite 1500 lacks sufficient integrity to withstand the mechanical stresses produced while the article is worn and ends up collapsing into a bunched state. This can create discomfort to the wearer as well. So too much conformance can lead to comfort issues during wear just as not enough conformance can.

In contrast, the materials selected in accordance with the present disclosure can reduce the friction loss of a portion of one strut disposed beneath another strut. Referring now to FIG. 15C, the adjacent struts overlap to a large extent. When materials are selected in accordance with the present disclosure, an overlap distance 1503 may be less than about 0.75 mm, less than about 0.5 mm, or less than about 0.2 mm, or about 0 mm. The overlap distance test is described in additional detail herein.

The materials utilized for the sample of FIGS. 15A-15C were a 28 gsm, bi-component 80 percent polypropylene and 20 percent polyethylene, spunbond, topsheet and an airlaid absorbent core comprising 180 gsm, 4.9 percent, 3 mm length, 1.7 dtex bi-component fiber, 14.7 percent of particle AGM and about 80 percent short cellulose fibers.

As noted previously, traditional fibrous absorbent core materials, comprise short cellulose fibers. It is believed that due to the length of the fibers, e.g. short, they are unable to form a substantial fiber network that can withstand the meso-scale processing described herein. It is believed that mechanical manipulation of these short fibers results in these short fiber materials being deformed and stretched (as they flow around the teeth for example) to such an extent that such processing typically leads to material tearing. The material tearing weakens the structure's ability to recover its shape when deformed while being worn as the user goes about their daily routine. For example, as shown regarding FIGS. 15A-15C, slits and tearing can occur where the fibers are too short.

As mentioned previously, to drive good conformance, the layer of the absorbent article which provides the most stiffness will likely be a good candidate for the formation of conforming features as described herein. So, as an example, an FM layer disposed between the topsheet and absorbent core may not need to be designed to withstand the meso-scale processes described herein. In such forms, if the absorbent core is the stiffest portion of the absorbent article, the breakage of constituent material of the FM layer, may not negatively impact the integrity of the absorbent article.

And the converse is also applicable. If an absorbent article includes an FM layer that is stiffer than its absorbent core counterpart, then the FM layer may be designed to withstand the meso-scale processes described herein. The absorbent core in such forms, however, may not need to be designed to withstand such processes. Or, in some instances, it may be beneficial to design the system to withstand the meso-scale processes described herein.

So, material selection can impact the level of conformance of the modified webs of the present disclosure. The inventors surprisingly have found that through the support of long fiber networks, e.g. longer than 6 mm, conformance features may be created in absorbent articles which provide fluid kinetic benefits along with desirable mechanical properties. These long fiber networks may be realized in the absorbent core, in the FM layer, and/or the topsheet, or any combination thereof. However, it is worth noting that a sufficient amount of long fibers/filaments should be utilized in order to create the long fiber network. Appropriate materials to accomplish the weakened areas between struts is described in additional detail hereafter.

As noted previously, the DOE between tooling impacts the level to which one layer is engaged with another layer. For example, as shown in FIG. 16, for lower DOE, a bottom 1621B of a depression may be disposed proximate to a wearer-facing surface of the absorbent core. In contrast, for a higher DOE, a bottom 1621A of a depression may be disposed more distal than the bottom 1621B. Forms are contemplated where variable depths of engagement are utilized. In such cases, depressions where the DOE is higher may be deeper than for depressions where the DOE was not as high.

Without wishing to be bound by theory it is believed that a long fiber network can reduce the likelihood of shredding of the absorbent core or shredding of the layer which dominates the flexibility of the absorbent article. It is believed that fibers within the absorbent core, the FM layer, and/or the topsheet should be greater than about 6 mm. It is further believed that longer thermoplastic fibers can span the depressions and support the bottoms of the depressions which connect adjacent struts. It is also believed that shorter fibers, e.g. cellulose, during mechanical manipulation, tend to separate from one another as they do not have sufficient length to tie into the fiber network of the absorbent system. It is worth noting that for a higher depth of engagement of the tooling mentioned herein, longer fibers may be required. Conversely for a lower depth of engagement, shorter fibers may be utilized; however, it is believed that a lower depth of engagement, below 5 mm, for example, may detrimentally impact the conformability of the absorbent article. In some forms, fiber lengths longer than tooling length, e.g. the length of the teeth 510 (shown in FIG. 6A), may be sufficient to create a long fiber network that can withstand the meso-scale processing. So, the depth of the depression may be shorter than the average length of thermoplastic fibers in the absorbent system, e.g. the FM layer and/or absorbent core.

The long fiber network is believed to allow the constituent material of the layers to more easily flow around the tooling utilized for the meso-scale processing. This flowing of the constituent material allows the constituent material to stay in-tact post processing without significant breakage of the fibers. It is further believed that extensible materials and/or crimped fibers can help the long fiber network maintain its structural integrity.

In addition to the length of fibers, it is believed that the way the fibers are tied together can also influence the fiber network. For example, it is believed that the density of bond sites (bond sites per square cm) via calendar bonding can impact the long fiber network. For example, where there is a high bond density, long fibers can effectively be made short due to the spacing of adjacent bond sites. In contrast, it is believed that air through bonding may beneficially impact the long fiber network as these types of bonds are seen as more easily broken during processing. As another example, ultrasonic bonding and/or thermal bonding of the fibers of these layers can be utilized to build a fiber network which can assist the long fiber network. Additional examples include spunlacing and needlepunching. Bond spacing, spunlacing and/or needlepunching can allow the long fiber network to flex/move and then recover. Appropriate bond spacing would ensure that effective fiber lengths are not less than about 6 mm. Some specific examples of sufficient fiber networks are described regarding Tables 1-4.

For the absorbent articles of the present disclosure, the dominant layer, i.e. the layer which most influences the flexibility of the article—generally the thickest material, may benefit from comprising a long fiber network. The "long" filaments or fibers of the long fiber network should make up between 15% and 50% by weight of the filaments and/or fibers in the fibrous structure, between 17% and 40% of the fibers in the fibrous structure, or between 20% and 30% of the fibers in the fibrous structure, specifically reciting all values within these ranges and any ranges created thereby. For example, long filaments, i.e. longer than 6 mm, may be in the absorbent core. In order for the absorbent core to survive the meso-scale processes described herein, it is believed that the basis weight of long fibers should be at least 15 percent of the basis weight of the absorbent core. However, where the absorbent core does not comprise the requisite long fiber percentage, layers of material adjacent to the absorbent core, e.g. fluid management layer and/or topsheet may contribute to the long fiber network. But it is believed that where the absorbent core lacks the requisite percentage of long fibers, a higher percentage than 15 percent may be required from the adjacent layers. For example, assuming that the fluid management layer and the absorbent core are provided with conforming features, if the absorbent core does not comprise at least 25 percent of long fibers, then the long fibers of the fluid management layer should also be assessed. In such instances, the cumulative basis weight of the long fibers should be evaluated against the cumulative basis weight of the fluid management layer and the absorbent core to determine the appropriate percentage of long fibers.

The filaments and/or fibers of the long fiber network may be capable of interconnecting or bonding with other filaments and/or fibers, such as, for example thermoplastic fibers. The filaments and/or fibers of the long fiber network should have an average length that is longer than the average strut height in the absorbent mesh and/or longer than the average depression depth. The average length of fibers of the long fiber network may be between about 6 mm to about 100 mm. Or, the long fiber network may comprise continuous filaments, e.g. meltblown, spun melt, spunbond, etc. Still, the long fiber network may comprise continuous filaments as well as fibers.

The filaments and/or fibers used to form the long fiber network may be bundles of filaments and/or fibers. For example, between 10 and 100 fibers may be in the form of a bundle such that at least 5% of the filaments and/or fibers will bond together. Bundling the filaments and/or fibers together allows for the filaments and/or fibers to form a fibrous network while maintaining desirable permeability.

Figure 17A:
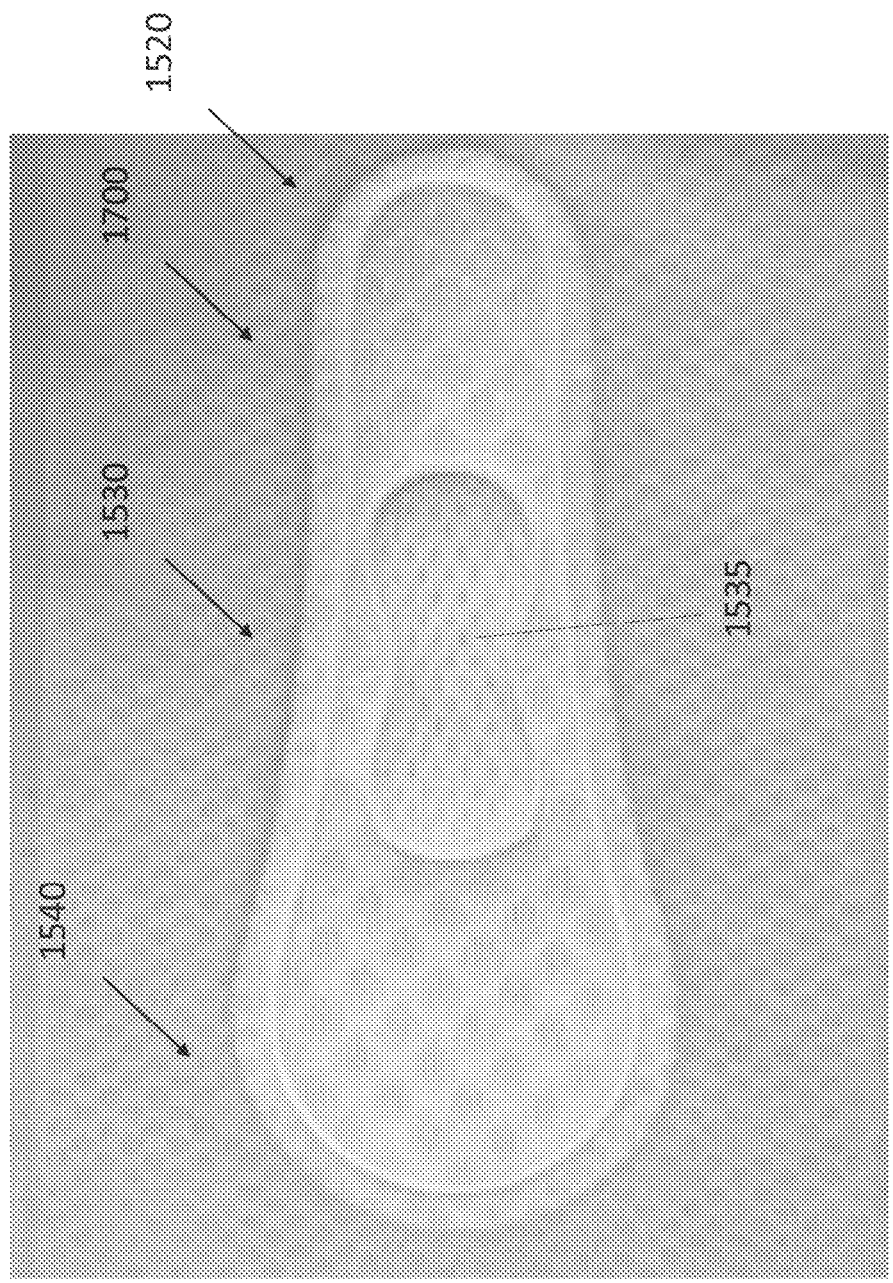
FIG. 17A is a photo showing a plan view of an absorbent article constructed in accordance with the present disclosure.

An exemplary absorbent article 1700 created in accordance with the present disclosure is shown in FIG. 17A. The article shown has been modified to provide good fluid acquisition in the target region 1530. As shown the target zone 1535 having a figure eight shape may comprise intimate contact between an FM layer and the absorbent core in the target zone 1535. Additionally, in some forms, the target zone 1535 may comprise apertures which extend through the topsheet, or through the topsheet and the FM layer.

Additionally, because the absorbent article 1700 may comprise conforming features as well in the target region 1530 which can allow the absorbent article 1700 to conform to the external labial structure of the wearer. Similarly, the first region 1520 and the second region 1540 may comprise conforming features which allow those portions of the absorbent article 1700 to conform to the complex surfaces of the user. However, the patterns utilized in the first and second regions 1520 and 1530 may provide more structural integrity to the absorbent article while the pattern in the target zone 1535 may provide more conformance to the body. Similarly, outboard of the target zone 1535, the target region 1530 may comprise the pattern of the first region 1520 and/or the second region 1540 or may comprise a pattern which provides additional structural integrity over that of the target zone 1535.

As shown, the first region 1520 and the second region 1540 may comprise conforming features which are generally diamond shape and which have a repeating pattern. Within each of the diamond shapes, there are a plurality of depressions of varying length. As shown, the depressions are generally oriented generally parallel to a long axis of the absorbent article 1700. However, the depressions may be oriented at an angle thereto or may be oriented generally parallel with a lateral axis of the absorbent article. Or, some of the diamonds within the pattern may comprise depression oriented in one direction while other diamonds within the pattern comprise depressions oriented in another direction. The same hold true regardless of the shape of units within the pattern, e.g. diamonds, circles, etc. Additional suitable shapes are disclosed below.

Also, as shown, the target region 1530, in a portion thereof, may comprise conforming features which are generally oriented in columns and staggered rows, where the columns are generally parallel to the long axis of the absorbent article 1700. The depressions may be longer than those of the diamond or longer than at least some of the depressions within the diamond pattern.

Figure 17B:
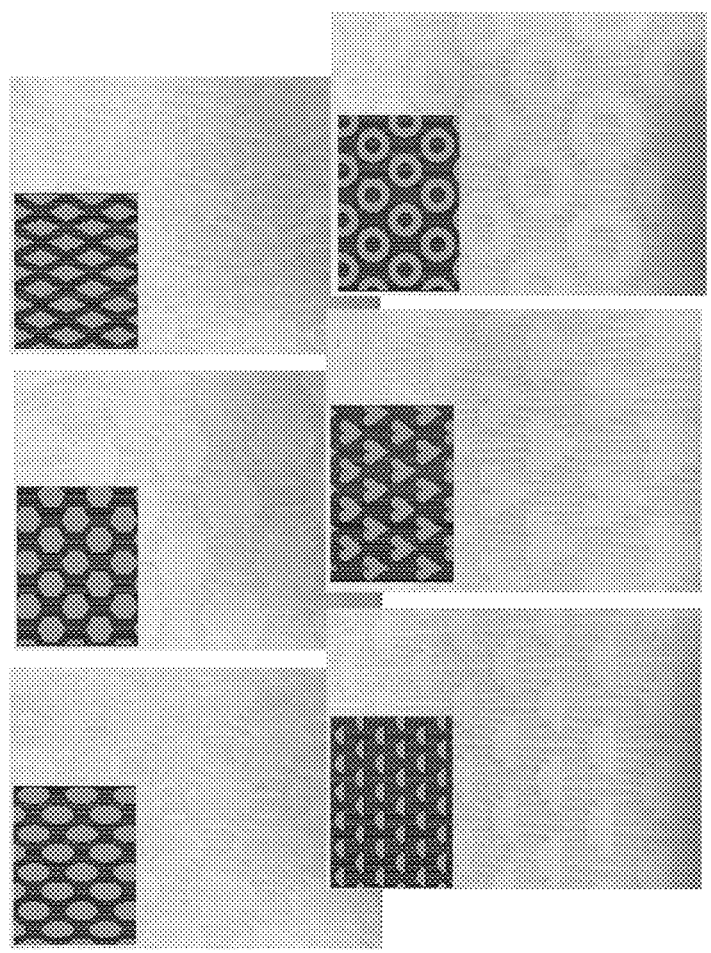
FIG. 17B is a schematic representation showing other potential pattern arrangements for the webs of the present disclosure.

Additional patterns which can be utilized for the webs of the present disclosure are provided regarding FIG. 17B. As shown, nodes may be any suitable shape, e.g. ovals, hexagons, diamonds, semicircles, hearts, donuts, rainbows, etc. Additional shaped include moons, clovers, balloons, stars, or combinations thereof. As shown, a plurality of struts extends between each of the nodes.

Absorbent Articles

Figure 18:
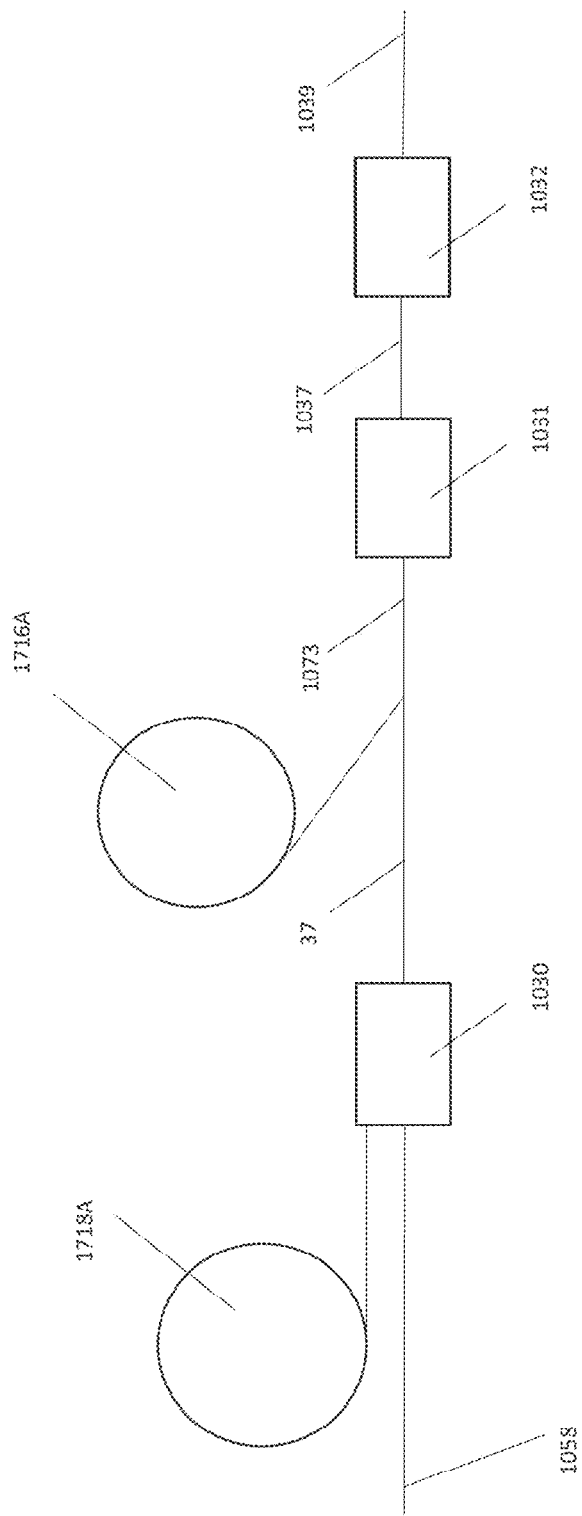
FIG. 18 is a schematic of a partial exemplary process for the creation of absorbent articles.

After the topsheet, FM layer, absorbent core, or any combination thereof, are provided with intimate contact and/or conforming features, the modified web may be further converted to produce an absorbent article. As shown in FIG. 18, a final web 1058 (which is inclusive of the final webs described herein) may be subsequently processed as described regarding FIG. 18 to create a plurality of absorbent articles 1039.

For example, for those forms where an absorbent core was not previously provided, an absorbent core web 1718A (shown as a roll) may be provided to a cut and place operation 1030 which cuts the absorbent core web 1718A and creates a plurality of discrete absorbent cores therefrom. The plurality of discrete absorbent cores may be placed on the plurality of discrete FM portions 20A (shown in FIG. 4) thereby forming the TFMAC laminate web 37. Subsequently, a backsheet 1716A (shown as a roll) may be placed on the TFMAC laminate web 37 thereby forming an absorbent article laminate web 1073. A joining operation 1031 may be utilized to join the backsheet with the TFMAC laminate web 37. Subsequently, the absorbent article laminate web 1073 may be subjected to a cutting operation 1032 which cuts the absorbent article laminate web 1037 into a plurality of discrete absorbent articles 1039. Cutting operations as well as cut and place operations are known in the art of disposable absorbent article production.

Topsheets of disposable absorbent articles are the wearer-facing surface of the article. The absorbent articles of the present disclosure may comprise any known or otherwise effective topsheet, such as one which is compliant, soft feeling, and non-irritating to the wearer's skin. Suitable topsheet materials include a liquid pervious material that is oriented towards and contacts the body of the wearer permitting bodily discharges to rapidly penetrate through it without allowing fluid to flow back through the topsheet to the skin of the wearer.

A suitable topsheet may be manufactured from a wide range of materials, such as porous foams, reticulated foams, apertured plastic films, woven materials, nonwoven materials, woven or nonwoven materials of natural fibers (e.g., wood or cotton fibers), synthetic fibers or filaments (e.g., polyester or polypropylene or bicomponent PE/PP fibers or mixtures thereof), or a combination of natural and synthetic fibers. Additional fibers or filaments include meltblown, nano, spunbond, carded, or the like. The topsheet may have one or more layers, for example a spunbond-meltblown-spunbond material. Any portion of the topsheet may be coated with a skin care composition, an antibacterial agent, a surfactant, and/or other beneficial agents. The topsheet may be hydrophilic or hydrophobic or may have hydrophilic and/or hydrophobic portions. If the topsheet is hydrophobic, typically apertures will be present so that bodily exudates may pass through the topsheet.

Where topsheet is desired to be mechanically manipulated, for example, for the formation of conforming features, the topsheet may comprise extensible material or material which comprises crimped fibers/filaments. If, non-extensible materials are utilized in the formation of conforming features, the topsheet may break or shred. Additional details of nonwoven webs with extensible fibers/filaments is provided in U.S. Patent No. US 2014/0170367. And, details of nonwoven webs with crimped fibers is provided in U.S. Patent Application Publication No. 2016/0166443.

Additionally, in some forms the idea of intimate contact can be applied to the topsheet. For example, the topsheet may comprise a film substrate and a nonwoven substrate. In such forms, the nonwoven substrate may be a carrier material upon which the film substrate may be extruded. Because the extruded film is in a semi-molten state, it is believed that the resultant composite provides intimate contact and performance benefits over a film and nonwoven laminate of the same constituent material. The film/nonwoven composite may then be processed as described herein, e.g. the addition of apertures to provide the ability to acquire fluid and the provision of conforming features may be performed on such film/nonwoven composites. Such film/nonwoven composites and processing thereof are described in additional detail in U.S. Patent Application Publication No. 2009/0026651, PCT Application Serial Nos. PCT/CN2017/089550, PCT/CN2017/089553, and PCT/CN2017/089554.

In some forms, the topsheet may comprise a composite of nonwoven materials. For example, a first nonwoven substrate may be created via a first spinbeam, and a second nonwoven substrate may be created via a second spinbeam. In some forms, the second spinbeam may form filaments on the filaments of the first spinbeam. It is believed that such creation of a composite nonwoven can create intimate contact between the substrates of the topsheet as opposed to creation via lamination of a first web to a second web. Such nonwoven webs and processes for forming such webs are described in U.S. Patent Application Publication No. 2017/0258651A1.

The FM layer and absorbent core may comprise any suitable material in some forms. For example, where the FM layer is not the stiffest layer of the absorbent article, the FM layer may comprise any suitable material which can rapidly absorb liquid insults from the topsheet and subsequently allow the liquid insults to be transferred to the absorbent core. Similarly, where the absorbent core is not the stiffest layer of the absorbent article, the absorbent core may comprise any suitable material which can absorb and retain liquid insults from the FM layer (where present) or the topsheet. There are many commercially available variants for the FM layer and absorbent core where conventional materials may be utilized.

However, where the FM layer or the absorbent core are the stiffest layers of the absorbent article, the materials of the FM layer or absorbent core should be carefully selected. Note that in some forms, the FM layer and the absorbent core may be designed to withstand the meso-scale processes described herein, e.g. comprising a long fiber network.

The absorbent system, either the FM layer and/or the absorbent core, may be webs such as, for example, nonwoven, a fibrous structure, a long thermoplastic filament and/or fiber reinforced airlaid web, a high loft nonwoven, a needlepunched web, a hydroentangled web, a fiber tow web, a woven web, a knitted web, a flocked web, a spunbond web, a layered spunbond/melt blown web, a carded fiber web, a coform web of cellulose fiber and melt blown or spun-melt fibers, a coform web of staple fibers and melt blown or spun-melt fibers, and layered webs that are layered combinations thereof.

The constituent filaments and/or fibers of the absorbent system can be comprised of polymers such as polyethylene, polypropylene, polyester, and blends thereof. The filaments can be spunbond. The filaments can be meltblown. The filaments and/or fibers can comprise cellulose, rayon, cotton, or other natural materials or blends of polymer and natural materials. The filaments and/or fibers can also comprise a super absorbent material such as polyacrylate or any combination of suitable materials. The filaments and/or fibers can be monocomponent, bi-component, and/or bi-constituent, non-round (e.g., capillary channel fibers), and can have major cross-sectional dimensions (e.g., diameter for round fibers) ranging from 0.1-500 microns. The constituent filaments and/or fibers of the absorbent system web may also be a mixture of different fiber types, differing in such features as chemistry (e.g. polyethylene and polypropylene), components (mono-and bi-), dtex (micro dtex and >20 dtex), shape (i.e. capillary and round) and the like. The constituent filaments and/or fibers can range from about 0.1 dtex to about 100 dtex.

Suitable thermoplastic filaments and/or fibers can be made from a single polymer (monocomponent fibers) or can be made from more than one polymer (e.g., bi-component fibers). The polymer comprising the sheath often melts at a different, typically lower, temperature than the polymer comprising the core. As a result, these bi-component filaments and/or fibers provide thermal bonding due to melting of the sheath polymer, while retaining the desirable strength characteristics of the core polymer.

Suitable bi-component filaments and/or fibers for use in the present invention can include sheath/core fibers having the following polymer combinations: polyethylene/polypropylene, polyethylvinyl acetate/polypropylene, polyethylene/polyester, polypropylene/polyester, copolyester/polyester, and the like. Particularly suitable bi-component thermoplastic filaments and/or fibers for use herein are those having a polypropylene or polyester core, and a lower melting copolyester, polyethylvinyl acetate or polyethylene sheath (e.g., DANAKLON.RTM., CELBOND.RTM. or CHISSO.RTM. bi-component fibers). These bi-component filaments and/or fibers can be concentric or eccentric. As used herein, the terms "concentric" and "eccentric" refer to whether the sheath has a thickness that is even, or uneven, through the cross-sectional area of the bi-component fiber. Eccentric bi-component filaments and/or fibers can be desirable in providing more compressive strength at lower fiber thicknesses. Suitable bi-component filaments and/or fibers for use herein can be either uncrimped (i.e. unbent) or crimped (i.e. bent). Bi-component fibers can be crimped by typical textile means such as, for example, a stuffer box method or the gear crimp method to achieve a predominantly two-dimensional or "flat" crimp.

The length of bi-component fibers can vary depending upon the particular properties desired for the fibers and the web formation process. Ideally, in an air formed web such as a long fiber reinforced airlaid web, these thermoplastic fibers have a length from about 6 mm to about 15 mm long, preferably from greater than about 6 mm long to about 12 mm long. The properties-of these thermoplastic fibers can also be adjusted by varying the diameter (caliper) of the fibers. The diameter of these thermoplastic fibers is typically defined in terms of either denier (grams per 9000 meters) or decitex (grams per 10,000 meters). Suitable bi-component thermoplastic fibers as used in an airlaid making machine such as a DanWeb machine can have a decitex in the range from about 1.0 to about 16, preferably from about 1.4 to about 10, and most preferably from about 1.7 to about 7 decitex.

Without wishing to be bound by theory, it is believed that FM layers and/or absorbent cores with good long fiber networks can withstand meso-scale processing. And, as noted previously, topsheets may contribute to the long fiber network to some extent as well. It is believed that fibers 6 mm or longer may be utilized to help provide the good long fiber network. For example, coform utilizes continuous filaments which measure well over 6 mm. It is further believed that thermoplastic bondable filaments and/or fibers are better to utilize than latex bonding.

For those forms of the absorbent system that comprise an FM layer and absorbent core, the FM layer and/or the absorbent core may be constructed as described herein. In one particular example, the absorbent core may comprise a substrate which comprises superabsorbent polymeric material. For example, a tissue web may comprise absorbent gelling material granules or fibers disposed on the tissue web.

The backsheet is generally that portion of the absorbent article positioned proximate to the garment-facing surface of the absorbent core. The backsheet may be joined to portions of the topsheet, the absorbent core, and/or any other layers of the absorbent article by any attachment methods known to those of skill in the art. The backsheet prevents, or at least inhibits, the bodily exudates absorbed and contained in the absorbent core from soiling articles such as bedsheets, undergarments, and/or clothing. The backsheet is typically liquid impermeable, or at least substantially impermeable. The backsheet may, for example, be or comprise a thin plastic film, such as a thermoplastic film having a thickness of about 0.012 mm to about 0.051 mm. Other suitable backsheet materials may include breathable materials which permit vapors to escape from the absorbent article, while still preventing, or at least inhibiting, bodily exudates from passing through the backsheet.

Figure 19:
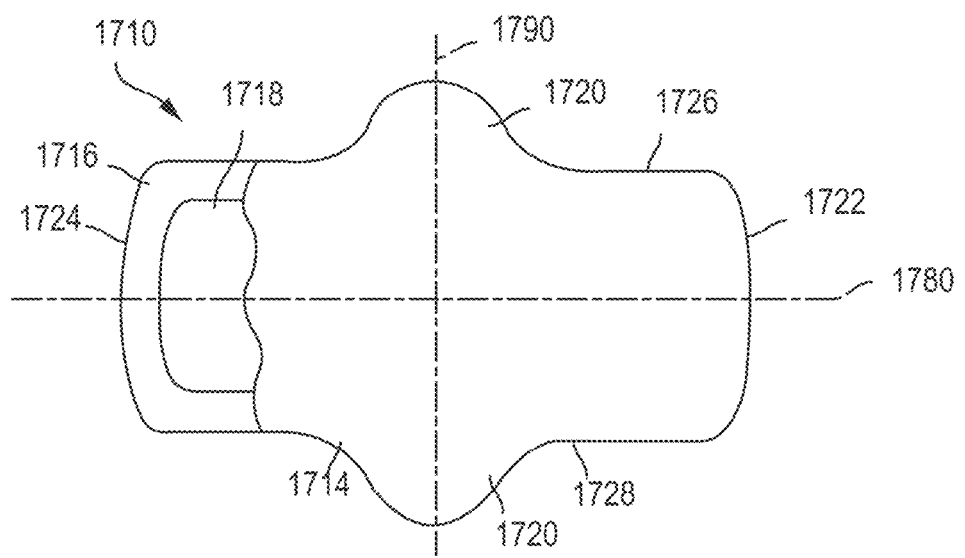
FIG. 19 is a top view of a feminine hygiene article, i.e. sanitary napkin, constructed in accordance with the present disclosure.

Exemplary absorbent articles of the present invention include diapers and/or feminine pads. Referring to FIG. 19, an absorbent article 1710 which may utilize the material webs described herein may be a sanitary napkin/feminine hygiene pad. As shown, the sanitary napkin 1710 may comprise a liquid permeable topsheet 1714, a liquid impermeable, or substantially liquid impermeable, backsheet 1716, and an absorbent core 1718 positioned intermediate the topsheet 1714 and the backsheet 1716. The sanitary napkin 1710 may comprise wings 1720 extending outwardly with respect to a longitudinal axis 1780 of the sanitary napkin 1710. The sanitary napkin 1710 may also comprise a lateral axis 1790. The wings 1720 may be joined to the topsheet 1714, the backsheet 1716, and/or the absorbent core 1718. The sanitary napkin 1710 may also comprise a front edge 1722, a rear edge 1724 longitudinally opposing the front edge 1722, a first side edge 1726, and a second side edge 1728 laterally opposing the first side edge 1726. The longitudinal axis 1780 may extend from a midpoint of the front edge 1722 to a midpoint of the rear edge 1724. The lateral axis 1790 may extend from a midpoint of the first side edge 1726 to a midpoint of the second side edge 1728. The sanitary napkin 1710 may also be provided with additional features commonly found in sanitary napkins as is known in the art. In some forms of the present invention, the wings may be provided with zones of extensibility as described in U.S. Pat. No. 5,972,806.

The absorbent article 1710 may further comprise an FM layer disposed between the topsheet 1714 and the absorbent core 1718. The FM layer may be configured as described herein. Similarly, the absorbent core may be configured as described herein.

One suitable material for the backsheet can be a liquid impervious thermoplastic film having a thickness of from about 0.012 mm (0.50 mil) to about 0.051 mm (2.0 mils), for example including polyethylene or polypropylene. Typically, the backsheet can have a basis weight of from about 5 g/m² to about 35 g/m². However, it should be noted that other flexible liquid impervious materials may be used as the backsheet. Herein, "flexible" refers to materials which are compliant and which will readily conform to the general shape and contours of the wearer's body.

The backsheet can be typically positioned adjacent an outer-facing surface of the absorbent core and can be joined thereto by any suitable attachment device known in the art. For example, the backsheet may be secured to the absorbent core by a uniform continuous layer of adhesive, a patterned layer of adhesive, or an array of separate lines, spirals, or spots of adhesive. Illustrative, but non-limiting adhesives, include adhesives manufactured by H. B. Fuller Company of St. Paul, Minn., U.S.A., and marketed as HL-1358J. An example of a suitable attachment device including an open pattern network of filaments of adhesive is disclosed in U.S. Pat. No. 4,573,986 entitled "Disposable Waste-Containment Garment", which issued to Minetola et al. on Mar. 4, 1986. Another suitable attachment device including several lines of adhesive filaments swirled into a spiral pattern is illustrated by the apparatus and methods shown in U.S. Pat. No. 3,911,173 issued to Sprague, Jr. on Oct. 7, 1975; U.S. Pat. No. 4,785,996 issued to Ziecker, et al. on Nov. 22, 1978; and U.S. Pat. No. 4,842,666 issued to Werenicz on Jun. 27, 1989. Alternatively, the attachment device may include heat bonds, thermal fusion bonds, pressure bonds, ultrasonic bonds, dynamic mechanical bonds, or any other suitable attachment device or combinations of these attachment devices. The backsheet may be additionally secured to the topsheet by any of the above-cited attachment devices/methods.

Still another example of a disposable absorbent article which may utilize the material webs of the present invention are diapers which include non-refastenable pants, re-fastenable pants and/or re-fastenable diapers. Diapers have can have a similar construction to that of sanitary napkins. An exemplary diaper is described below.

Figure 20:
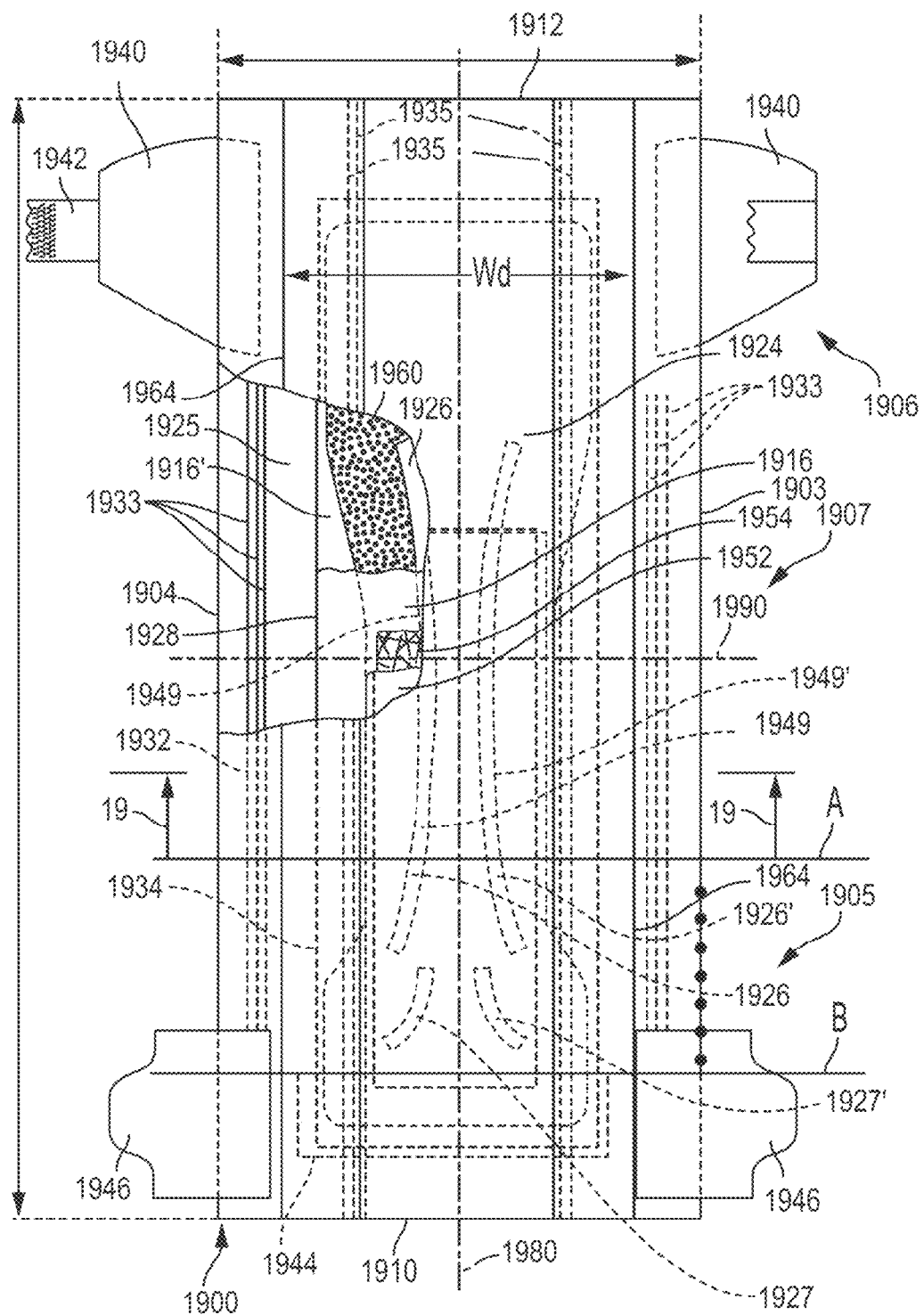
FIG. 20 is a top view of an absorbent article with some layers partially removed in accordance with the present disclosure.

Referring to FIG. 20, a plan view of an example absorbent article that is a diaper 1900 in its flat-out, uncontracted state (i.e., with elastic induced contraction pulled out) with portions of the structure being cut-away to more clearly show the construction of the diaper 1900 and with its wearer-facing surface toward the viewer. This diaper is shown for illustration purpose only as the present disclosure may be used for making a wide variety of diapers and other absorbent articles.

The absorbent article may comprise a liquid permeable topsheet 1924, a liquid impermeable backsheet 1925, an absorbent core 1928 positioned at least partially intermediate the topsheet 1924 and the backsheet 1925, and barrier leg cuffs 1934. The absorbent article may also comprise a distribution layer 1954 and an acquisition layer 1952 that will both be further discussed below. In various forms, the acquisition layer 1952 may instead distribute bodily exudates and the distribution layer 1954 may instead acquire bodily exudates or both layers may distribute and/or acquire bodily exudates. The absorbent article may also comprise elasticized gasketing cuffs 1932 joined to the chassis of the absorbent article, typically via the topsheet and/or backsheet, and substantially planar with the chassis of the diaper.

The Figures also show typical taped diaper components such as a fastening system comprising adhesive tabs 1942 or other mechanical fasteners attached towards the rear edge of the absorbent article 1900 and cooperating with a landing zone on the front of the absorbent article 1900. The absorbent article may also comprise other typical elements, which are not represented, such as a rear elastic waist feature and a front elastic waist feature, for example.

The absorbent article 1900 may comprise a front waist edge 1910, a rear waist edge 1912 longitudinally opposing the front waist edge 1910, a first side edge 1903, and a second side edge 1904 laterally opposing the first side edge 1903. The front waist edge 1910 is the edge of the absorbent article 1900 which is intended to be placed towards the front of the user when worn, and the rear waist edge 1912 is the opposite edge. Together the front waist edge 1910 and the rear waist edge form waist opening when the absorbent article 1900 is donned on a wearer. The absorbent article 1900 may have a longitudinal axis 1980 extending from the lateral midpoint of the front waist edge 1910 to a lateral midpoint of the rear waist edge 1912 of the absorbent article 1900 and dividing the absorbent article 1900 in two substantially symmetrical halves relative to the longitudinal axis 1980, with article placed flat and viewed from the wearer-facing surface as illustrated FIG. 20. The absorbent article may also have a lateral axis 1990 extending from the longitudinal midpoint of the first side edge 1903 to the longitudinal midpoint of the second side edge 1904. The length L of the absorbent article 1900 may be measured along the longitudinal axis 1980 from the front waist edge 1910 to the rear waist edge 1912. The crotch width of the absorbent article 1900 may be measured along the lateral axis 1990 from the first side edge 1903 to the second side edge 1904. The absorbent article 1900 may comprise a front waist region 1905, a rear waist region 1906, and a crotch region 1907. The front waist region, the rear waist region, and the crotch region each define ⅓ of the longitudinal length of the absorbent article. Front and back portions may also be defined on opposite sides of the lateral axis 1990.

The backsheet 1925 may be joined to the topsheet 1924, the absorbent core 1928, and/or any other element of the absorbent article 1900 by any attachment methods known to those of skill in the art. Suitable attachment methods are described above with respect to methods for joining the topsheet 1924 to other elements of the absorbent article 1900.

The absorbent article 1900 may comprise a pair of barrier leg cuffs 1934. Each barrier leg cuff may be formed by a piece of material which is bonded to the absorbent article so it can extend upwards from the inner surface of the absorbent article and provide improved containment of liquids and other bodily exudates approximately at the junction of the torso and legs of the wearer. The barrier leg cuffs 1934 are delimited by a proximal edge 1964 joined directly or indirectly to the topsheet 1924 and/or the backsheet 1925 and a free terminal edge 1966, which is intended to contact and form a seal with the wearer's skin. The barrier leg cuffs 1934 extend at least partially between the front waist edge 1910 and the rear waist edge 1912 of the absorbent article on opposite sides of the longitudinal axis 1980 and are at least present in the crotch region 1907. The barrier leg cuffs 1934 may be joined at the proximal edge 1964 with the chassis of the absorbent article by a bond 1965 which may be made by gluing, fusion bonding, or combination of other suitable bonding processes. The bond 1965 at the proximal edge 64 may be continuous or intermittent. The bond 1965 closest to the raised section of the leg cuffs 1934 delimits the proximal edge 1964 of the standing up section of the leg cuffs 1934.

The barrier leg cuffs 1934 may be integral with the topsheet 1924 or the backsheet 1925 or may be a separate material joined to the absorbent article's chassis. The material of the barrier leg cuffs 1934 may extend through the whole length of the diapers but may be "tack bonded" to the topsheet 1924 towards the front waist edge 1910 and rear waist edge 1912 of the absorbent article so that in these sections the barrier leg cuff material remains flush with the topsheet 1924.

Each barrier leg cuff 1934 may comprise one, two or more elastic strands or strips of film 1935 close to this free terminal edge 1966 to provide a better seal.

In addition to the barrier leg cuffs 1934, the absorbent article may comprise gasketing cuffs 1932, which are joined to the chassis of the absorbent article, in particular to the topsheet 1924 and/or the backsheet 1925 and are placed externally relative to the barrier leg cuffs 1934. The gasketing cuffs 1932 may provide a better seal around the thighs of the wearer. Each gasketing leg cuff may comprise one or more elastic strings 1933 or elastic elements in the chassis of the absorbent article between the topsheet 1924 and backsheet 1925 in the area of the leg openings. All or a portion of the barrier leg and/or gasketing cuffs may be treated with a lotion or skin care composition. The barrier leg cuffs may be constructed in a number of different configurations, including those described in U.S. Pat. App. Publ. No. 2012/0277713.

In a form, the absorbent article may comprise front ears 1946 and rear ears 1940. The ears may be an integral part of the chassis, such as formed from the topsheet 1924 and/or backsheet 1925 as side panel. Alternatively, as represented on FIG. 19, the ears (1946, 1940) may be separate elements attached by gluing, heat embossing, and/or pressure bonding. The rear ears 1940 may be stretchable to facilitate the attachment of the tabs 1942 to the landing zone 1944 and maintain the taped diapers in place around the wearer's waist. The rear ears 1940 may also be elastic or extensible to provide a more comfortable and contouring fit by initially conformably fitting the absorbent article to the wearer and sustaining this fit throughout the time of wear well past when absorbent article has been loaded with exudates since the elasticized ears allow the sides of the absorbent article to expand and contract.

Data regarding various samples is provided in the tables below. A description of the samples is provided after the presentation of all the data tables. In Table 1, data is provided regarding the mechanical properties of modified (Samples 6a-8c) and unmodified samples (no conforming features—Samples 1-5). The samples listed in Table 1 are absorbent core samples only. And, the values of the mechanical properties listed in Table 1 are with regard to the three point bend test described herein and the bunch compression test described herein. The three point bend test measures the fundamental bending properties and stiffness that relate to the material or the product's ability to conform to complex anatomical features. A lower number is indicative of a more conforming material. In contrast, the bunch compression test is a measure of a material's ability to recover its original shape or form following compression, particularly as measured, when wet. For this data, a higher value indicates the ability of a material to recover to its initial shape even when wet. A higher number can indicate conformance of a material even after being insulted with liquid.

TABLE 1

| Sample No. | Bending Modulus Dry (N/mm$^2$) | Bending Stiffness Dry (N * mm$^2$) | Recovery Energy Wet (mJ) | Recovery Percentage Wet (%) |
|---|---|---|---|---|
| 1 - unmodified | 0.68 | 30.9 | 3.51 | 64 |
| 2 - unmodified | 0.126 | 13.02 | 1.06 | 38 |
| 3 - unmodified | 0.121 | 8.79 | 0.34 | 31 |
| 4 - unmodified | 2.12 | 11.72 | 0.50 | 28 |
| 5 - unmodified | 0.085 | 11.39 | 1.86 | 63 |
| 6a | 0.062 | 3.42 | 0.65 | 43 |
| 6b | 0.022 | 1.30 | 0.59 | 43 |
| 6c | 0.024 | 2.16 | 0.79 | 50 |
| 7a | 0.06 | 3.255 | 0.04 | 26 |
| 7b | 0.016 | 1.139 | 0.05 | 23 |
| 7c | 0.023 | 1.95 | 0.18 | 25 |
| 8a | 0.088 | 1.63 | Collapse | Collapse |
| 8b | 0.014 | 0.326 | Collapse | Collapse |
| 8c | 0.038 | 0.81 | Collapse | Collapse |

Table 2 includes data regarding the three point bend test and the bunch compression test as disclosed herein. The samples of table 2 include an absorbent core and a fluid management layer which comprise conforming features as described herein. The data illustrates that some samples while exhibiting great conformance during initial use, e.g.

low bending modulus, low bending stiffness, their in-use states do not show the same promise. For example, these same samples may exhibit an extremely low recovery energy which suggests that in use, these products may collapse and actually lead to leakage problems. However, without additional investigation regarding their potential issues in use, some may be tempted by "fool's gold" and simply rely on the great initial conformance of the product.

TABLE 2

| Sample No. | Bending Modulus Dry (N/mm$^2$) | Bending Stiffness Dry (N * mm$^2$) | Recovery Energy Wet (mJ) | Recovery Percentage Wet (%) |
|---|---|---|---|---|
| 9a | 0.064 | 4.72 | 0.84 | 58 |
| 9b | 0.026 | 1.79 | 0.81 | 56 |
| 9c | 0.027 | 2.77 | 1.35 | 52 |
| 10a | 0.085 | 7.49 | 0.33 | 37 |
| 10b | 0.015 | 1.47 | 0.31 | 34 |
| 10c | 0.03 | 3.26 | 0.76 | 30 |
| 11a | 0.093 | 7.83 | 0.40 | 48 |
| 11b | 0.026 | 2.77 | 0.38 | 40 |
| 11c | 0.033 | 3.74 | 0.62 | 48 |

The data from Table 2 shows that the addition of a fluid management layer increases the values associated with recovery energy and recovery percentage. It is worth noting that the addition of the fluid management layer also increased the values of the bending modulus and bending stiffness. However, the increases in bending modulus and bending stiffness as compared to the recovery energy and recovery percentage, is not 1 to 1.

Table 3 includes data regarding integration of topsheet, fluid management layer, and absorbent core regarding the three point bend test and bunch compression test disclosed herein. In each sample, the topsheet, fluid management layer, and absorbent cores comprised conforming features which integrated all three layers. Additionally, there are some samples of currently marketed products which have been tested as well.

Ratio 1 is between Bending Stiffness and Recovery Energy. In samples 12a-14d, the Samples illustrate that in most cases, the embossed only samples have a high stiffness to drive acceptable Recovery Energy. Whereas on the Samples comprising conforming features, acceptable recovery energy is achieved at lower stiffness levels. Additionally, the ratio of "stiffness/energy of recovery" is almost 50% reduced or better for the Samples comprising conforming features. So, it is believed that the Samples which comprise these conforming features can recover from bunching, maintain pad shape to be more comfortable and conformable without relying on stiffness to do this. It is believed that a wet recovery energy of below 0.4 mJ, the absorbent article may have conformance and possibly performance issues during use due to its inability to recover its shape when wet.

The bending stiffness to wet recovery energy ratio of less than 17 may be achieved as demonstrated by the data regardless of the type of absorbent system. Specifically, where the absorbent core comprised a coformed absorbent core with continuous filaments (Sample 2), a bending stiffness to wet recovery energy ratio of than 4 and even less than 3 was achieved. For those absorbent cores of the airlaid variety, e.g. Samples 3 and 4, a much lower bending stiffness to wet recovery energy was achieved. For example, regarding Sample 3, by utilizing the conforming features as described herein, the bending stiffness to wet energy recovery ratio was lower than 17, lower than 15, and even lower than 10. Regarding Sample 4, by utilizing the conforming features described herein, the bending stiffness to wet recovery ratio was lower than 13, lower than 10, and even lower than 8.

Ratio 2 is between bending stiffness and caliper. As the data illustrates, there is a significant reduction in stiffness for the products comprising conforming features compared to those which are embossed. Even where the Samples have a higher caliper, which in theory should increase stiffness, many of the Samples with conforming features exhibit a 50% reduction in stiffness over the Samples which were embossed.

TABLE 3

| Sample No. | Bending Modulus Dry (N/mm$^2$) | Bending Stiffness Dry (N * mm$^2$) | Recovery Energy Wet (mJ) | Recovery Percentage Wet (%) | Caliper (mm) | Ratio 1 | Ratio 2 |
|---|---|---|---|---|---|---|---|
| 12a-emboss | 0.136 | 12.55 | 2.63 | 53 | 2.80 | 4.77 | 4.5 |
| 12b-DIA | 0.042 | 4.57 | 1.97 | 72 | 2.96 | 2.32 | 1.5 |
| 12c-CEN | 0.032 | 2.77 | 1.79 | 49 | 2.74 | 1.55 | 1.0 |
| 12d-ALT | 0.053 | 4.23 | 2.58 | 57 | 2.67 | 1.64 | 1.6 |
| 13a-emboss | 0.177 | 15.3 | 0.88 | 35 | 2.74 | 17.39 | 5.6 |
| 13b-DIA | 0.035 | 4.72 | 1.04 | 41 | 3.17 | 4.54 | 1.5 |
| 13c-CEN | 0.033 | 3.74 | 0.86 | 39 | 2.99 | 4.35 | 1.3 |
| 13d-ALT | 0.084 | 10.25 | 1.10 | 37 | 3.07 | 9.32 | 3.3 |
| 14a-emboss | 0.605 | 43.46 | 3.16 | 54 | 2.57 | 13.75 | 16.9 |
| 14b-DIA | 0.061 | 7.32 | 1.99 | 58 | 3.05 | 3.68 | 2.4 |
| 14c-CEN | 0.052 | 5.7 | 1.68 | 58 | 2.96 | 3.39 | 1.9 |
| 14d-ALT | 0.102 | 11.32 | 1.81 | 57 | 2.95 | 6.25 | 3.8 |
| Conventional Sample 1 | 0.21 | 55.6 | 0.58 | 46 | 2.36 | 95.8 | 23.6 |
| Conventional Sample 2 | 0.68 | 69.4 | 1.90 | 33 | 2.54 | 36.52 | 27.3 |

The stiffness to caliper ratio of 4 or less may be achieved as demonstrated by the data. Specifically, where the absorbent core comprised a coformed absorbent core with continuous filaments (Sample 2), a stiffness to caliper ratio of 4 or less was achieved and even less than 2. For those absorbent cores of the airlaid variety, e.g. Samples 3 and 4, a much lower stiffness to caliper ratio was achieved. For example, regarding Sample 3, by utilizing the conforming features as described herein, the stiffness to caliper ratio was lower than 5 and even lower than 4. Regarding Sample 4, by utilizing the conforming features described herein, the stiffness to caliper ratio was lower than 15, lower than 10, lower than 5, and lower than 4.

Additionally, the data illustrates the fact that bending stiffness and bending modulus can be affected based on the conforming features provided to the article to enable customizable fit to a user's unique anatomical shape. Additionally, the data shows that the arrangement of the zones in the absorbent article can similarly impact the bending stiffness and the bending modulus to provide the most comfortable conforming fit to her body. The same holds true for recovery energy and recovery percentage.

Regarding bending stiffness, the absorbent articles comprising conforming features as described herein showed lower bending stiffness than their conventional counterparts. For example, for those products which comprised the Sample 2 absorbent core, bending stiffness was less than 12, less than 8, and even less than 5. For Sample 3, the bending stiffness was less than 15 and even less than 12. For Sample 4, the bending stiffness was less than 40, less than 20, and even less than 15.

Data regarding fluid kinetics of the samples listed in Table 3 is provided below in Table 4. The data is derived from the NMR mouse method, the free fluid acquisition test, and the blot test described herein. The NMR test measures the ability of a product to drain fluid from the area closest to the body. A low value on this test suggests that the user may experience a dry feeling. Additionally, a low value on the NMR test suggests that the article is able to regenerate void volume for the next insult. The Free Fluid Acquisition test measures the speed of absorbing fluid insults to the topsheet. A lower number suggests that the article can absorb liquid insults quickly. The Blot test measures the residual fluid that would remain on the body as well as how much of the area of the product would likely be stained.

Ratio 3 is between Blot Residual versus caliper. In the Samples 12a-14d, the Samples comprising conforming features lead to at least a 50% reduction in residual fluid compared to embossing only. So we can achieve not just less fluid on skin analog but we can achieve this in a thin, more conforming and comfortable absorbent article.

The blot to caliper ratio of less than 11 may be achieved as demonstrated by the data regardless of the type of absorbent system. Specifically, where the absorbent core comprised a coformed absorbent core with continuous filaments (Sample 2), a blot to caliper ratio of less than 12, less than 11, less than 8, and even less than 7 was achieved. For those absorbent cores of the airlaid variety, e.g. Samples 3 and 4, a much lower blot to caliper ratio was achieved. For example, regarding Sample 3, by utilizing the conforming features as described herein, the blot to caliper ratio was lower than 19, lower than 15, and even lower than 10. Regarding Sample 4, by utilizing the conforming features described herein, the blot to caliper ratio was lower than 20, lower than 15, and even lower than 10.

Additionally, the data illustrates the fact that residual fluid (NMR), free fluid acquisition time, blot residual and blot stain size, can be improved over conventional methods of layer attachment or as shown over embossing based on the conforming features provided to the article. For example, NMR data regarding the absorbent cores of Sample 4, were much lower than 200 µl, much lower than 100 µl, much lower than 50 µl, and lower than 30 µl, than those measured for absorbent articles which did not comprise the conforming features of the present disclosure. Similarly, for the absorbent cores of Sample 3, NMR data showed a reduction with the provision of conforming features, i.e. less than 20 µl and even less than 17 µl. Regarding the products which comprised the Sample 2 absorbent cores, they demonstrated NMR data that was less than about 7 µl while also having a free fluid acquisition time of less than 100 seconds.

Regarding the blot test, the data also demonstrates that those products comprising conforming features consistently had lower values than their conventional counterparts. For example, for those products utilizing the absorbent core of Sample 2, the blot residual values were less than 30 mg, less than 20 mg, and even less than 18 mg. For each of Samples 3 and 4, the blot residual values were less than 50 mg, less than 40 mg, and even less than 30 mg.

TABLE 4

| Sample No. | Fluid Remaining 0.5 mm (µl) | Free Fluid Acquisition (seconds) | Blot Residual (mg) | Blot Stain (mm^3) | Caliper (mm) | Ratio 3 |
| --- | --- | --- | --- | --- | --- | --- |
| 12a-emboss | 5.0 | 120 | 34 | 1192 | 2.80 | 12.1 |
| 12b-DIA | 6.0 | 38 | 13 | 1405 | 2.96 | 4.4 |
| 12c-CEN | 5.0 | 76 | 16 | 1473 | 2.74 | 5.8 |
| 12d-ALT | 13.0 | 63 | 16 | 1365 | 2.67 | 6.0 |
| 13a-emboss | 23.0 | 37 | 54 | 1400 | 2.74 | 19.7 |
| 13b-DIA | 15.0 | 39 | 28 | 1625 | 3.17 | 8.8 |
| 13c-CEN | 7.0 | 61 | 22 | 1501 | 2.99 | 7.4 |
| 13d-ALT | 15.0 | 17 | 20 | 1647 | 3.07 | 6.5 |
| 14a-emboss | 262.0 | 64 | 56 | 1733 | 2.57 | 21.8 |
| 14b-DIA | 14.0 | 43 | 27 | 1733 | 3.05 | 8.9 |
| 14c-CEN | 5.0 | 44 | 21 | 1732 | 2.96 | 7.1 |
| 14d-ALT | 25.0 | 16 | 27 | 1734 | 2.95 | 9.2 |
| Conventional Sample 1 | 5.0 | | 73 | 5033 | 2.36 | 30.9 |
| Conventional Sample 2 | 17.0 | | 66 | 4033 | 2.54 | 25.9 |

Additionally, the data shows that the arrangement of the zones in the absorbent article can similarly impact the bending stiffness and the bending modulus. The same holds true for recovery energy and recovery percentage.

The absorbent articles comprising conforming features as described herein, demonstrated at blot residual value of Samples:

Sample 1: A coformed absorbent core having a total basis weight of 224 gsm. The coformed absorbent core comprised 121.8 gsm cellulose fibers, 52.2 gsm of 3.0 micron continuous polypropylene fibers, and 50 gsm of superabsorbent polymer (AGM). These materials were homogenously blended.

Sample 2: A coformed absorbent core having a total basis weight of 186 gsm. The coformed absorbent core comprised 105 gsm cellulose, 45 gsm, 3.0 micron, continuous polypropylene fibers with 36 gsm of AGM. These materials were homogeneously blended.

Sample 3: A 150 gsm airlaid absorbent on a carded nonwoven material. The material comprised 4 mm polyethylene/polyethylene terephthalate fibers, cellulose fibers, and latex binder material. This material did not include superabsorbent polymer.

Sample 4: A unitary airlaid absorbent core having a basis weight of 160 gsm. The absorbent core comprises cellulosic fibers and superabsorbent polymer and includes a low percentage of bondable fibers. Available from Gladfelter GmbH, Falkenhagen Germany. Fibrous super absorbent may be utilized in some cases.

Sample 5: A carded spunlace (38-40 mm fiber length) material having a basis weight of 140 gsm comprising 21.8 percent viscose rayon, 35.4 percent bicomponent fibers (polyethylene terephthalate and copolyethylene terephthalate), and 42.9 percent polyethylene terephthalate monocomponent fibers.

Figure 21:
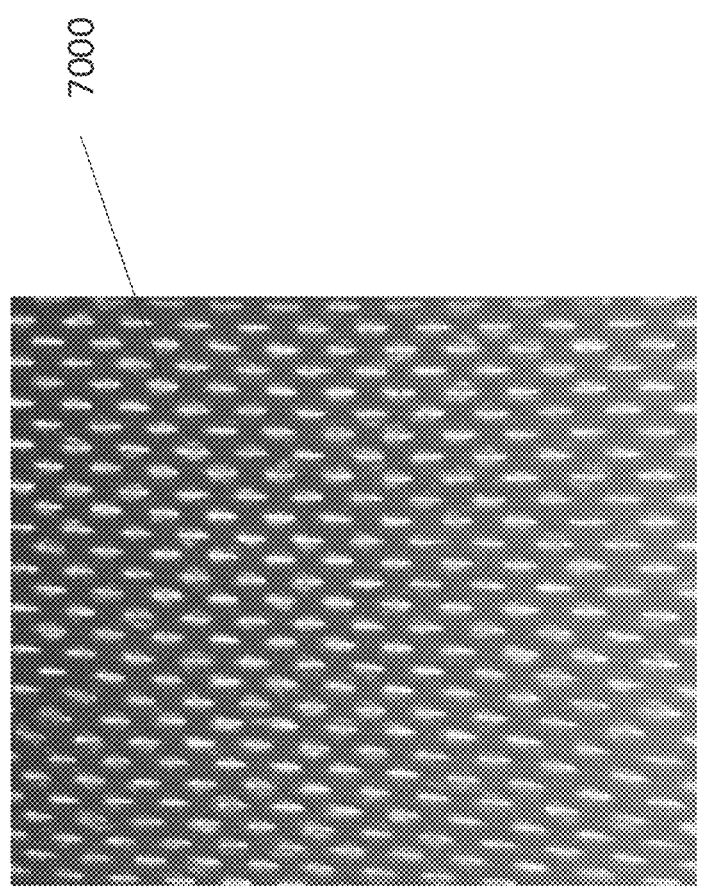
FIG. 21 is a photograph which shows tooling for making conforming features as described herein.

Regarding the Samples 6a-14d many were provided with conforming features oriented in a negative Z-direction in accordance with the following patterns. DIAMOND—shown in FIG. 17A in the first zone 1520 and the second zone 1540. The tooling for the DIAMOND pattern comprises teeth of differing lengths. The depth of engagement for the tooling was 2.54 mm and spacing between the teeth was 2.03 mm. CENTER— shown in FIG. 17A (within the figure eight looking area) in a portion of the target region 1530. The teeth of the CENTER pattern are staggered. The depth of engagement for the tooling was 2.54 mm and spacing between the teeth was 2.03 mm. ALT— This pattern is formed by teeth 7000 shown in FIG. 21. As shown, teeth are provided in columns and staggered rows. The depth of engagement was 2.54 mm and the spacing between teeth was 2.54 mm.

Samples 6a, 6b, and 6c: The material of Sample 2 was provided with conforming features comprising the DIAMOND pattern for 6a, the CENTER pattern for 6b, and the ALT pattern for 6c.

Samples 7a, 7b, and 7c: The material of Sample 3 was provided with conforming features comprising the DIAMOND pattern for 7a, the CENTER pattern for 7b, and the ALT pattern for 7c.

Samples 8a, 8b, and 8c: The material of Sample 4 was provided with conforming features comprising the DIAMOND pattern for 8a, the CENTER pattern for 8b, and the ALT pattern for 8c.

Samples 9a, 9b, and 9c: A 24 gsm hydrophilic carded nonwoven and the material of Sample 2 were provided with conforming features comprising the DIAMOND pattern for 9a, the CENTER pattern for 9b, and the ALT pattern for 9c. The 24 gsm nonwoven was utilized as a fluid management layer in these Samples and positioned superjacent to the absorbent cores.

Samples 10a, 10b, and 10c: The material of Sample 3 and a 35 gsm laminate material comprising AGM and a tissue layer were provided with conforming features comprising the DIAMOND pattern for 10a, the CENTER pattern for 10b, and the ALT pattern for 10c.

Samples 11a, 11b, and 11c: A 110 gsm carded spunlace (38-40 mm fiber length) material comprising 35.9 percent viscose, 34.1 percent polyethylene terephthalate, and 30 percent polyethylene terephthalate/copolyethylene terephthalate bicomponent fibers and the material of Sample 4 were provided with conforming features comprising the DIAMOND pattern for 11a, the CENTER pattern for 11b, and the ALT pattern for 11c.

Figure 22:
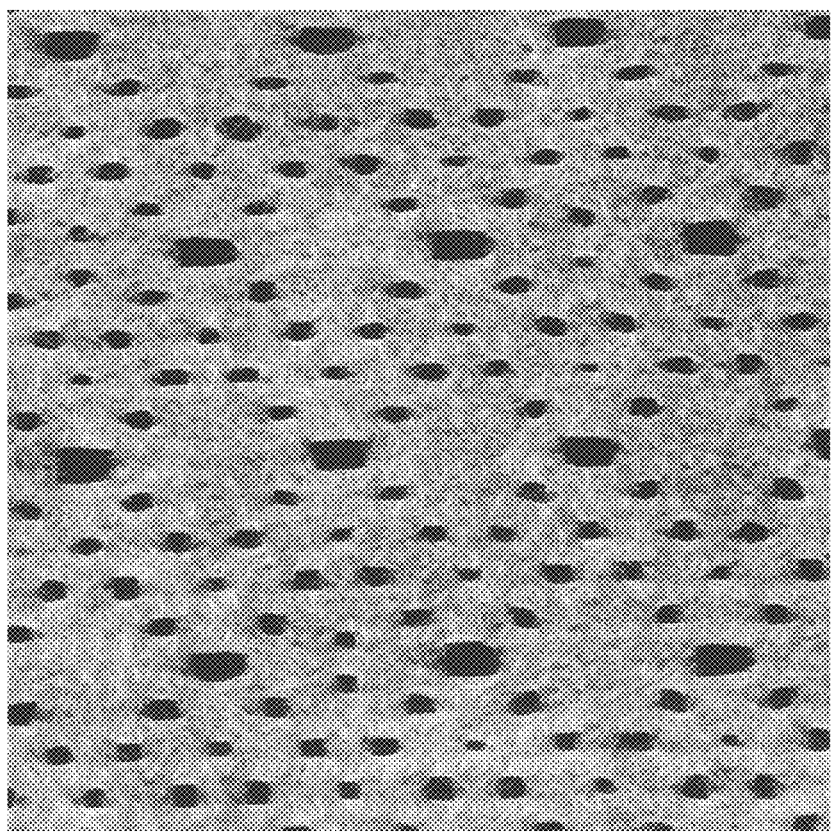
FIG. 22 is a photograph of a nonwoven web comprising an aperture pattern as described herein.

Each of Samples 12a-14d comprised a hydrophobic 24 gsm carded air through bonded nonwoven having bi-component fibers with polyethylene and polyethylene terephthalate and a lower layer of 25 gsm spunbond web comprising bi-component fibers having polyethylene and polypropylene components, wherein the lower layer was treated with a surfactant at 0.45 percent by weight. The upper and lower layers were apertured via the overbonding process described in FIGS. 9A and 9B and comprised the aperture pattern shown in FIG. 22. This material will collectively be referred to as the TOPSHEET in the description of the remainder of the Samples.

Additionally, some of the Samples, namely 12a, 13a, and 14a, were provided with embossing, which as noted previously, is not considered a conforming feature for the sake of this disclosure. In order to facilitate review of this data, the terms "emboss"; "DIA" (for DIAMOND); "CEN" (for CENTER); or "ALT" are utilized in the Tables regarding Samples 12a-14d.

Samples 12a, 12b, 12c, and 12d: The TOPSHEET and the material described in Samples 9a, 9b, and 9c, were provided with embossing for 12a, the DIAMOND pattern for 12b, the CENTER pattern for 12c, and the ALT pattern for 12d.

Samples 13a, 13b, 13c, and 13d: The TOPSHEET and the material described in Samples 10a, 10b, and 10c, were provided with embossing for 13a, the DIAMOND pattern for 13b, the CENTER pattern for 13c, and the ALT pattern for 13d.

Samples 14a, 14b, 14c, and 14d: The TOPSHEET and the material described in Samples 11a, 11b, an 11c, were provided with embossing for 14a, the DIAMOND pattern for 14b, the CENTER pattern for 14c, and the ALT pattern for 14d.

Conventional Sample 1—Always Ultra Thin size 1 available in market in Western Europe.

Conventional Sample 2—SCA Bodyform size 1 available in market in Western Europe.

Test Methods

Layers of Interest

For any of the methods below in which all the component layers of an article will not be tested, the layers of interest may be separated using cryo-spray as needed from layers which will not be tested.

AMF (Artificial Menstrual Fluid)

The Artificial Menstrual Fluid (AMF) is composed of a mixture of defibrinated sheep blood, a phosphate buffered saline solution and a mucous component. The AMF is prepared such that it has a viscosity between 7.15 to 8.65 centistokes at 23° C.

Viscosity on the AMF is performed using a low viscosity rotary viscometer (a suitable instrument is the Cannon LV-2020 Rotary Viscometer with UL adapter, Cannon Instrument Co., State College, PA, or equivalent). The appropriate size spindle for the viscosity range is selected, and instrument is operated and calibrated as per the manufacturer. Measurements are taken at 23° C.±1 C° and at 60 rpm. Results are reported to the nearest 0.01 centistokes.

Reagents needed for the AMF preparation include: defibrinated sheep blood with a packed cell volume of 38% or greater (collected under sterile conditions, available from Cleveland Scientific, Inc., Bath, OH, or equivalent), gastric mucin with a viscosity target of 3-4 centistokes when prepared as a 2% aqueous solution (crude form, available from Sterilized American Laboratories, Inc., Omaha, NE, or equivalent), 10% v/v lactic acid aqueous solution, 10% w/v potassium hydroxide aqueous solution, sodium phosphate dibasic anhydrous (reagent grade), sodium chloride (reagent grade), sodium phosphate monobasic monohydrate (reagent grade) and distilled water, each available from VWR International or an equivalent source.

The phosphate buffered saline solution consists of two individually prepared solutions (Solution A and Solution B). To prepare 1 L of Solution A, add 1.38±0.005 g of sodium phosphate monobasic monohydrate and 8.50±0.005 g of sodium chloride to a 1000 mL volumetric flask and add distilled water to volume. Mix thoroughly. To prepare 1 L of Solution B, add 1.42±0.005 g of sodium phosphate dibasic anhydrous and 8.50±0.005 g of sodium chloride to a 1000 mL volumetric flask and add distilled water to volume. Mix thoroughly. To prepare the phosphate buffered saline solution, add 450±10 mL of Solution B to a 1000 mL beaker and stir at low speed on a stir plate. Insert a calibrated pH probe (accurate to 0.1) into the beaker of Solution B and add enough Solution A, while stirring, to bring the pH to 7.2±0.1.

The mucous component is a mixture of the phosphate buffered saline solution, potassium hydroxide aqueous solution, gastric mucin and lactic acid aqueous solution. The amount of gastric mucin added to the mucous component directly affects the final viscosity of the prepared AMF. To determine the amount of gastric mucin needed to achieve AMF within the target viscosity range (7.15-8.65 centistokes at 23° C.) prepare 3 batches of AMF with varying amounts of gastric mucin in the mucous component, and then interpolate the exact amount needed from a concentration versus viscosity curve with a least squares linear fit through the three points. A successful range of gastric mucin is usually between 38 to 50 grams.

To prepare about 500 mL of the mucous component, add 460±10 mL of the previously prepared phosphate buffered saline solution and 7.5±0.5 mL of the 10% w/v potassium hydroxide aqueous solution to a 1000 mL heavy duty glass beaker. Place this beaker onto a stirring hot plate and while stirring, bring the temperature to 45° C.±5 C°. Weigh the pre-determined amount of gastric mucin (±0.50 g) and slowly sprinkle it, without clumping, into the previously prepared liquid that has been brought to 45° C. Cover the beaker and continue mixing. Over a period of 15 minutes bring the temperature of this mixture to above 50° C. but not to exceed 80° C. Continue heating with gentle stirring for 2.5 hours while maintaining this temperature range. After the 2.5 hours has elapsed, remove the beaker from the hot plate and cool to below 40° C. Next add 1.8±0.2 mL of the 10% v/v lactic acid aqueous solution and mix thoroughly. Autoclave the mucous component mixture at 121° C. for 15 minutes and allow 5 minutes for cool down. Remove the mixture of mucous component from the autoclave and stir until the temperature reaches 23° C.±1 C°.

Allow the temperature of the sheep blood and mucous component to come to 23° C.±1 C°. Using a 500 mL graduated cylinder, measure the volume of the entire batch of the previously prepared mucous component and add it to a 1200 mL beaker. Add an equal volume of sheep blood to the beaker and mix thoroughly. Using the viscosity method previously described, ensure the viscosity of the AMF is between 7.15-8.65 centistokes. If not the batch is disposed and another batch is made adjusting the mucous component as appropriate.

The qualified AMF should be refrigerated at 4° C. unless intended for immediate use. AMF may be stored in an air-tight container at 4° C. for up to 48 hours after preparation. Prior to testing, the AMF must be brought to 23° C.±1 C°. Any unused portion is discarded after testing is complete.

Blot Test

The Blot test measures the amount of AMF transferred to an article from a blotter sheet (as the residual AMF left on the blotter sheet), and the size of the stain as measured on the article's surface. This blot is repeated on the same specimen for a total of five times, with the cumulative blot dimension and individual residual mass on the blotter sheet recorded after each blot. A blotter sheet (available as Apollo Plain Paper Copier Transparency Film, ACCO brands, Ronkonkoma, NY, or equivalent) is used as a blotting surface. The surface energy as determined by ASTM D7490-13 of the blotter sheet should be approximately 50 $mJ/m^2$. The blotter sheets are cut to a dimension of 76 mm long by 63 mm wide for testing. A nylon plate 76 mm long by 63 mm wide by 3 mm thick is paired with a weight, which together have a combined mass to provide a confining pressure of 0.69 KPa on the specimen. AMF as described herein is used for the test fluid.

Using a cutting die (76 mm long by 63 mm wide) cut a specimen from the longitudinal and lateral midpoint of the article. Remove the release paper and lightly talc the adhesive to reduce stickiness. Measure the mass of a single blotter sheet and record to the nearest 0.0001 g. Place the sheet onto a bench top. Pipet 1.00 mL of AMF onto the center of the blotter sheet. Lineup the specimen with the edges of the sheet and lower the specimen, body facing side down, onto the blotter sheet. Place the nylon plate with weight onto the specimen and wait 15 min. Afterwards remove the plate and weight, then the specimen. Place the specimen body side facing upwards onto the bench. Measure the mass of the blotter sheet and residual AMF and record to the nearest 0.0001 g. Subtract the blotter sheet's original mass from the total mass and report as AMF residual to the nearest 0.0001 g. Using a calibrated ruler, measure a bounding box (rectangle) that encompasses the stain as observed from the top surface of the specimen and record as length in the CD direction and length in the MD direction. Calculate and record the stain area (CD×MD) as observed from the top and record to the nearest 1 $mm^2$. Turn the specimen over and measure a bounding box (rectangle) that encompasses the stain as observed from the bottom of the specimen and record as length in the CD direction and length in the MD direction. Calculate and record the stain area (CD×MD) as observed from the bottom and record to the nearest 1 $mm^2$.

In like fashion, using the same blotter sheet and specimen, dose the specimen four (4) additional times using a 1.00 mL aliquot for each cycle. Report the residual AMF from the blotter sheet and the stain area as seen from both top and bottom of the specimen for each cycle.

Bunch Compression

Bunched Compression of a sample is measured on a constant rate of extension tensile tester (a suitable instrument is the MTS Alliance using Testworks 4.0 software, as available from MTS Systems Corp., Eden Prairie, MN, or equivalent) using a load cell for which the forces measured are within 10% to 90% of the limit of the cell. All testing is performed in a room controlled at 23° C.±3 C° and 50%±2% relative humidity. The test can be performed wet or dry.

Referring to FIGS. 25-27B, the bottom stationary fixture 3000 consists of two matching sample clamps 3001 each 100 mm wide each mounted on its own movable platform 3002a, 3002b. The clamp has a "knife edge" 3009 that is 110 mm long, which clamps against a 1 mm thick hard rubber face 3008. When closed, the clamps are flush with the interior side of its respective platform. The clamps are aligned such that they hold an un-bunched specimen horizontal and orthogonal to the pull axis of the tensile tester. The platforms are mounted on a rail 3003 which allows them to be moved horizontally left to right and locked into position. The rail has an adapter 3004 compatible with the mount of the tensile tester capable of securing the platform horizontally and orthogonal to the pull axis of the tensile tester. The upper fixture 2000 is a cylindrical plunger 2001 having an overall length of 70 mm with a diameter of 25.0 mm. The contact surface 2002 is flat with no curvature. The plunger 2001 has an adapter 2003 compatible with the mount on the load cell capable of securing the plunger orthogonal to the pull axis of the tensile tester.

Samples are conditioned at 23° C.±3 C° and 50%±2% relative humidity for at least 2 hours before testing. When testing a whole article, remove the release paper from any panty fastening adhesive on the garment facing side of the article. Lightly apply talc powder to the adhesive to mitigate any tackiness. If there are cuffs, excise them with scissors, taking care not to disturb the top sheet of the product. Place the article, body facing surface up, on a bench. On the article identify the intersection of the longitudinal midline and the lateral midline. Using a rectangular cutting die, cut a specimen 100 mm in the longitudinal direction by 80 mm in the lateral direction, centered at the intersection of the midlines. When testing just the absorbent body of an article, place the absorbent body on a bench and orient as it will be integrated into an article, i.e., identify the body facing surface and the lateral and longitudinal axis. Using a rectangular cutting die, cut a specimen 100 mm in the longitudinal direction by 80 mm in the lateral direction, centered at the intersection of the midlines.

The specimen can be analyzed both wet and dry. The dry specimen requires no further preparation. The wet specimens are dosed with 7.00 mL ±0.01 mL 10% w/v saline solution (100.0 g of NaCl diluted to 1L deionized water). The dose is added using a calibrated Eppendorf-type pipettor, spreading the fluid over the complete body facing surface of the specimen within a period of approximately 3 sec. The wet specimen is tested 15.0 min ±0.1 min after the dose is applied.

Program the tensile tester to zero the load cell, then lower the upper fixture at 2.00 mm/sec until the contact surface of the plunger touches the specimen and 0.02 N is read at the load cell. Zero the crosshead. Program the system to lower the crosshead 15.00 mm at 2.00 mm/sec then immediately raise the crosshead 15.00 mm at 2.00 mm/sec. This cycle is repeated for a total of five cycles, with no delay between cycles. Data is collected at 100 Hz during all compression/decompression cycles.

Position the left platform 3002a 2.5 mm from the side of the upper plunger (distance 3005). Lock the left platform into place. This platform 3002a will remain stationary throughout the experiment. Align the right platform 3002b 50.0 mm from the stationary clamp (distance 3006). Raise the upper probe 2001 such that it will not interfere with loading the specimen. Open both clamps. Place the specimen with its longitudinal edges (i.e., the 100 mm long edges) within the clamps. With the specimen laterally centered, securely fasten both edges. Move the right platform 3002b toward the stationary platform 3002a a distance 20.0 mm. Allow the specimen to bow upward as the movable platform is positioned. Manually lower the probe 2001 until the bottom surface is approximately 1 cm above the top of the bowed specimen.

Start the test and collect displacement (mm) verses force (N) data for all five cycles. Construct a graph of Force (N) versus displacement (mm) separately for all cycles. A representative curve is shown in FIG. 27A. From the curve record the Maximum Compression Force for each Cycle to the nearest 0.01N. Calculate the % Recovery between the First and Second cycle as (TD-E2)/(TD-E1)*100 where TD is the total displacement and E2 is the extension on the second compression curve that exceeds 0.02 N. Record to the nearest 0.01%. In like fashion calculate the % Recovery between the First Cycle and other cycles as $(TD-E_i)/(TD-E1)*100$ and report to the nearest 0.01%. Referring to FIG. 27B, calculate the Energy of Compression for Cycle 1 as the area under the compression curve (i.e., area A+B) and record to the nearest 0.1 mJ. Calculate the Energy Loss from Cycle 1 as the area between the compression and decompression curves (i.e., Area A) and report to the nearest 0.1 mJ. Calculate the Energy of Recovery for Cycle 1 as the area under the decompression curve (i.e. Area B) and report to the nearest 0.1 mJ. In like fashion calculate the Energy of Compression (mJ), Energy Loss (mJ) and Energy of Recovery (mJ) for each of the other cycles and record to the nearest 0.1 mJ For each sample, analyze a total of five (5) replicates and report the arithmetic mean for each parameter. All results are reported specifically as dry or wet including test fluid (0.9% or 10%).

Caliper

Caliper at 0.69 KPa can be performed on the whole product or specific layers of interest. Layers of interest are separated using cryo-spray as needed. Samples are conditioned at 23° C.±3 C° and 50%±2% relative humidity for two hours prior to testing. Unless otherwise specified calipers are performed centered at the visibly identifiable zones.

The caliper of a specimen is measured using a calibrated digital linear caliper (e.g. Ono Sokki GS-503 or equivalent fitted with a 24.2 mm diameter foot with an anvil that is large enough that the specimen can lie flat. The foot applies a confining pressure of 0.69 KPa to the specimen. Zero the caliper foot against the anvil. Lift the foot and insert the specimen flat against the anvil with the body facing side facing upward and the site of interest centered under the foot. Lower the foot at about 5 mm/sec onto the specimen. Read the caliper (mm) 5.0 sec after resting the foot on the specimen and record to the nearest 0.01 mm.

Long Fiber Basis Weight

The long fiber basis weight determines the basis weight of fibers longer than 6.0 mm found in the top sheet, secondary top sheet and core of an article. Nonwovens such as spunlace, spunbond, or film laminates used as top sheets or fluid management layers will be treated as long fibers.

Cut a specimen 25.4 mm by 25.4 mm at the longitudinal and lateral center of the article through the entire article using a cutting die. The edges of the specimen are cut parallel and perpendicular to the longitudinal and lateral axis of the article. Remove the back sheet from the cut specimen then measure the mass of the remaining specimen to the nearest 0.0001 g and record. Calculate the basis weight of the specimen and record to the nearest 0.01 gsm. Separate the top sheet, secondary top sheet, and core into individual specimens to be tested. Measure the mass of each layer to the nearest 0.0001 g and record as TS1, STS1 and C1 respectively. Inspect each layer to determine if it contains cellulosic fibers.

Layers containing cellulosic fibers are analyzed as follows. Prepare a stock Schweizer reagent by dissolving Copper(II) hydroxide in ammonium hydroxide (%50 v/v) at a ratio of 1:4 w/w. Submerge the specimen in a volume of the reagent in excess of 30 g of reagent for each 1 g of cellulose in the specimen. Place the mixture on an orbital rocker to digest for 16 hrs. Afterward collect the polymeric fibers from the mixture and place into 50 mL of water. Repeat wash step until blue reagent is removed from the fibers. Transfer the fibers into a tared petri dish and with the aid of a stereomicroscope determine if the lengths of the fibers are longer than 6.0 mm. Dry the fibers that are longer than 6.0 mm and measure and record their mass to the nearest 0.001 g. Calculate the basis weight of the layers that do not contain cellulose fibers and record to the nearest 0.01 gsm. For layers that do contain cellulose, calculate the basis weight of the fibers that are longer than 6.0 mm and record to the nearest 0.001 gsm. Sum the basis weights for each of the layers to determine the overall basis weight of fibers over 6.0 mm and report to the nearest 0.01 gsm.

Three Point Bend

The bending properties of a sample are measured on a constant rate of extension tensile tester (a suitable instrument is the MTS Insight HSEL using Testworks 4.0 Software, as available from MTS Systems Corp., Eden Prairie, MN) using a load cell for which the forces measured are within 2% to 90% of the limit of the cell. All testing is performed in a room controlled at 23° C.±3 C° and 50%±2% relative humidity.

The bottom stationary fixture consists of two bars 3.175 mm in diameter by 60 mm in length, made of polished stainless steel each mounted on its own vertical fork. These 2 bars are mounted horizontally, aligned front to back and parallel to each other, with top radii of the bars vertically aligned. Furthermore, the fixture allows for the two bars to be move horizontally away from each other on a track so that a span can be set between them while maintaining their orientation. The top movable fixture consists of a third bar also 3.175 mm in diameter by 60 mm in length, made of polished stainless steel mounted on a vertical fork. When in place the bar of the top fixture is parallel to and aligned front to back with the bars of the bottom fixture. Both fixtures include an integral adapter appropriate to fit the respective position on the tensile tester frame and lock into position such that the bars are orthogonal to the motion of the crossbeam of the tensile tester.

Set the span between the bars of the lower fixture to 25 mm±0.05 mm (center of bar to center of bar) with the upper bar centered at the midpoint between the lower bars. Set the gage (bottom of top bar to top of lower bars) to 1.0 cm.

Samples are conditioned at 23° C.±3 C° and 50%±2% relative humidity two hours prior to testing. Remove the overwrap and release papers were removed from pads. Dust the exposed adhesive surfaces on the back sheet and if present wings with talcum powder to eliminate adhesive tack. Remove in excess talc from the surfaces. Lay the pads flat, top sheet facing upward on a lab bench, and mark the longitudinal midline of the product. Next, mark a lateral line across the product using the longitudinal midline of the wings. If no wings are present mark a lateral line at the midpoint of the core. Remove rectangular specimens from the front (Zone A), middle (Zone B) and rear (Zone C). Each specimen is centered along the longitudinal axis of the sample, is 50.8 mm in the longitudinal direction by 30 mm in the lateral direction and is the entire thickness of the product. Zone A specimen is centered 45.4 mm from the front edge of the product. Zone B is centered at the lateral mark on the sample. Zone C is centered at 45.4 mm from the rear of the product. For each specimen measure the caliper at its center as described and record to the nearest 0.01 mm.

Program the tensile tester for a compression test, to move the crosshead down at a rate of 1.0 mm/sec for 25 mm collecting force (N) and displacement (m) data at 50 Hz and return the crosshead to its original gage. Load a specimen such that it spans the two lower bars centered under the upper bar. A CD bend refers to bending along the longitudinal axis of the pad (longitudinal direction parallel to bars) and MD bend refers to bending along the lateral axis of the pad (lateral direction parallel to bars). Zero the crosshead and load cell. Start the run and collect data.

Construct a graph of force (N) verses displacement (mm). Read the maximum Peak Force from the graph and divide by the specimen width (m). Record as the Peak Force/Width to nearest 0.1 N/m. From the curve, calculate the Slope as the greatest slope of a linear segment fitted to the curve, wherein the length of the segment incorporates 20% of the curve then divide by the width of the specimen and report to the nearest 0.1 N/mm. From the slope calculate:

Modulus $(N/mm^2)$=Slope*$[25^3/(4*Sample Width*Caliper^3)]$

Moment of Inertia $(mm^4)$=(Sample Width*$Caliper^3$)/12

Bending Stiffness $(N*mm^2)$=Modulus*Moment of Inertia where caliper and sample width are in mm.

Measures are repeated in like fashion for 10 MD and 10 CD specimens and report the average separately for each of the ten values for Modulus to the nearest 0.01 $N/m^2$ and Bending Stiffness to the nearest 0.01 $N*mm^2$.

NMR MOUSE

Figure 23:
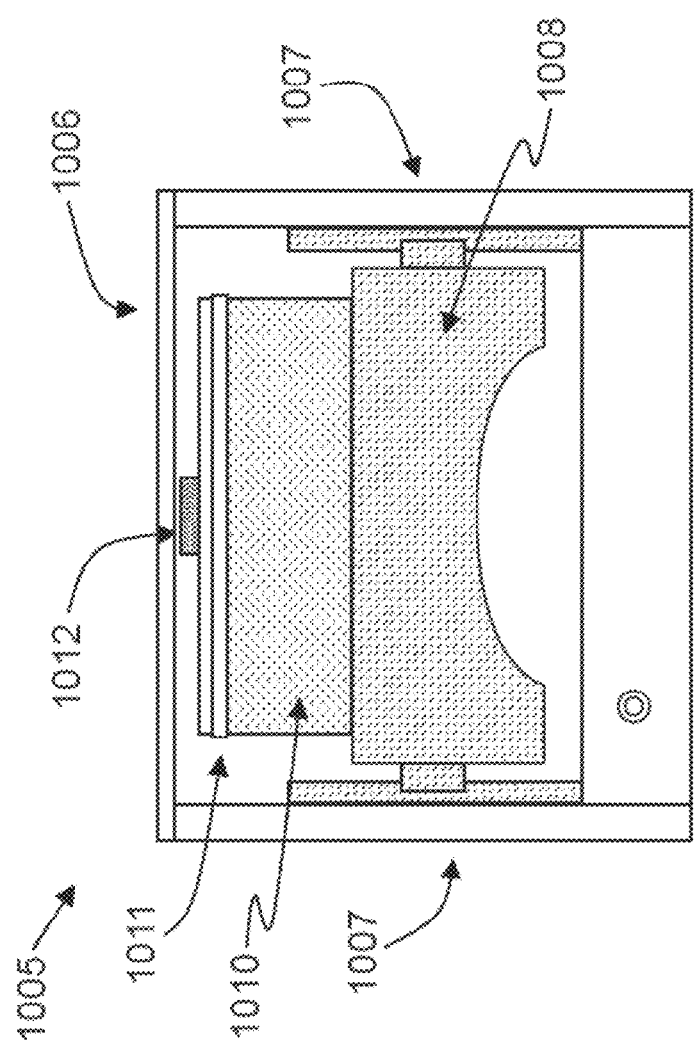
FIG. 23 is a schematic representation of an apparatus for the NMR mouse test method described herein.
Figure 24:
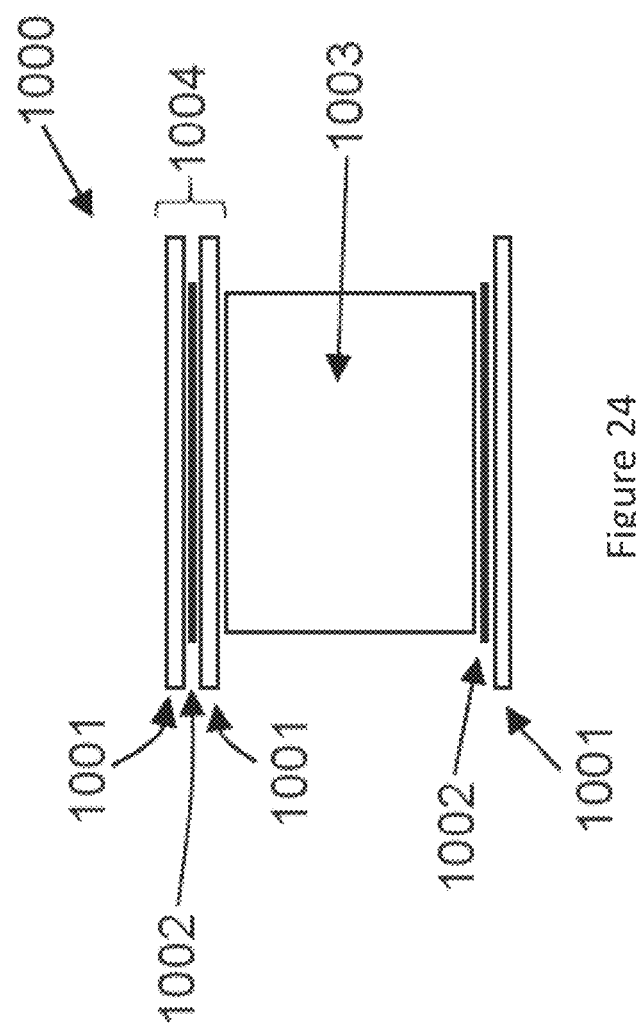
FIG. 24 is a schematic representation of a specimen setup for the apparatus of FIG. 23.
Figure 25:
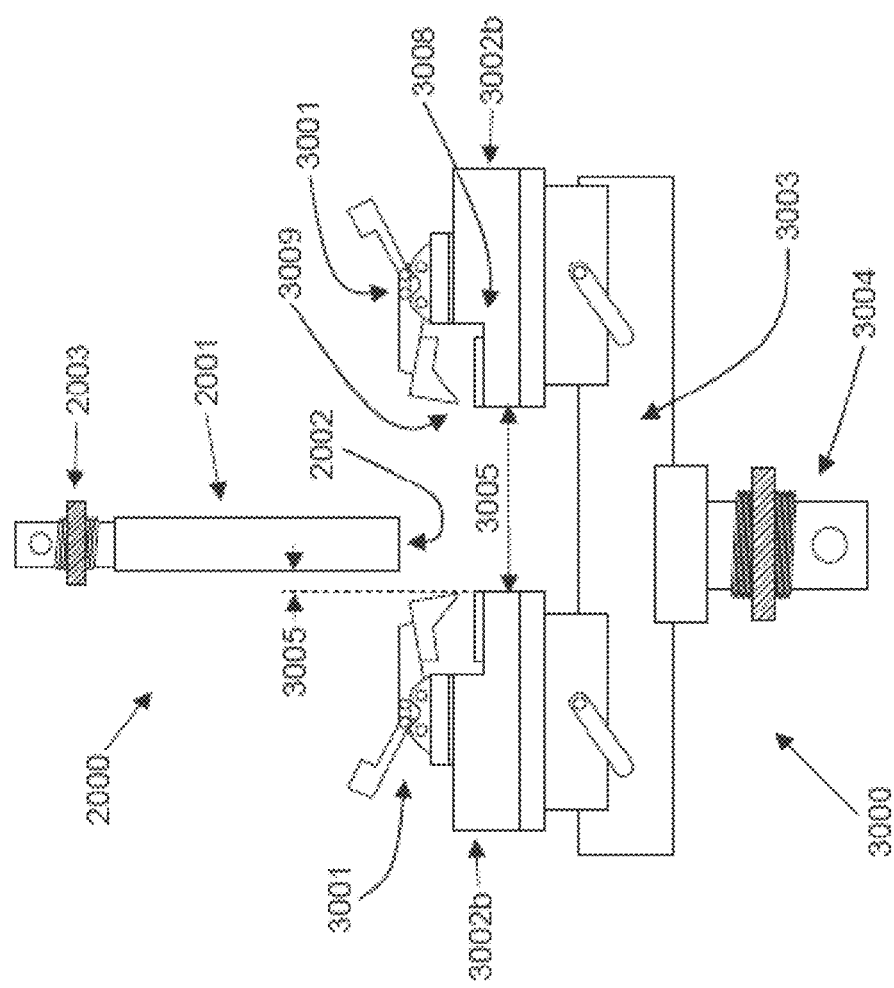
FIG. 25 is a schematic depiction showing an apparatus for the Bunch Compression test method as described herein.

The NMR-MOUSE (Mobile Universal Surface Explorer) is a portable open NMR sensor equipped with a permanent magnet geometry that generates a highly uniform gradient perpendicular to the scanner surface. Referring to FIGS. 23 and 24, a frame 1007 with horizontal plane 1006 supports the specimen and remains stationary during the test. A flat sensitive volume of the specimen is excited and detected by a surface rf coil 1012 placed on top of the magnet 1010 at a position that defines the maximum penetration depth into the specimen. By repositioning the sensitive slice across the specimen by means of a high precision lift 1008, the scanner can produce one-dimensional profiles of the specimen's structure with high spatial resolution.

An exemplary instrument is the Profile NMR-MOUSE model PM25 with High-Precision Lift available from Magritek Inc., San Diego, CA. Requirements for the NMR-MOUSE are a 100 μm resolution in the z-direction, a measuring frequency of 13.5 MHz, a maximum measuring depth of 25 mm, a static gradient of 8 T/m, and a sensitive volume (x-y dimension) of 40 by 40 mm². Before the instrument can be used, perform phasing adjustment, check resonance frequency and check external noise level as per the manufacturer's instruction. A syringe pump capable of delivering test fluid in the range of 1 mL/min to 5 mL/min ±0.01 mL/min is used to dose the specimen. All measurements are conducted in a room controlled at 23° C.±0.5° C. and 50%±2% relative humidity.

The test solution is Paper Industry Fluid (PIF) prepared as 15 g carboxymethylcellulose, 10 g NaCl, 4 g $NaHCO_3$, 80 g glycerol (all available from SigmaAldrich) in 1000 g distilled water. 2 mM/L of Diethylenetriaminepentaacetic acid gadolinium (III) dihydrogen salt (available from SigmaAldrich) is added to each. After addition the solutions are stirred using a shaker at 160 rpm for one hour. Afterwards the solutions are checked to assure no visible undissolved crystals remain. The solution is prepared 10 hours prior to use.

Products for testing are conditioned at 23° C.±0.5° C. and 50%±2% relative humidity for two hours prior to testing. Identify the intersection of the lateral and longitudinal center line of the product. Cut a 40.0 mm by 40.0 mm specimen from the product, centered at that intersection, with the cut edges parallel and perpendicular to the longitudinal axis of the product. The garment facing side of the specimen 1003 is mounted on a 50 mm×50 mm×0.30 mm glass slide 1001 using a 40.0 mm by 40.0 mm piece of double-sided tape 1002 (tape must be suitable to provide NMR Amplitude signal). A top cap 1004 is prepared by adhering two 50 mm×50 mm×0.30 mm glass slides 1001 together using a 40 mm by 40 mm piece of two-sided tape 1002. The cap is then placed on top of the specimen. The two tape layers are used as functional markers to define the dimension of the specimen by the instrument.

First a 1-D Dry Distribution Profile of the specimen is collected. Place the prepared specimen onto the instrument aligned over top the coils. Program the NMR-MOUSE for a Carr-Purcell-Meiboom-Gill (CPMG) pulse sequence consisting of a 90° x-pulse follow by a refocusing pulse of 180° y-pulse using the following conditions:

Repetition Time=500 ms
Number of Scans=8
Number of Echoes=8
Resolution=100 μm
Step Size=−100 μm Collect NMR Amplitude data (in arbitrary units, a.u.) versus depth (μm) as the high precision lift steps through the specimen's depth.

The second measure is the Kinetic Experiment of the test fluid moving though the sensitive NMR volume as test fluid is slowly added to the top of the specimen. The "trickle" dose is followed by a "gush" dose added using a calibrated dispenser pipet. Program the NMR-MOUSE for a CPMG pulse sequence using the following conditions:

Measurement Depth=5 mm
Repetition Time=200 ms
90° Amplitude=−7 dB
180° Amplitude=0 dB
Pulse Length=5 μs Echo Time=90 μs
Number of Echoes=128
Echo Shift=1 μs
Experiments before trigger=50
Experiments after trigger=2000
Rx Gain=31 dB
Acquisition Time=8 μs
Number of Scans=1

Rx Phase is determined during the phase adjustment as described by the vendor. A value of 230° was typical for our experiments. Pulse length depends on measurement depth which here is 5 mm. If necessary the depth can be adjusted using the spacer 1011.

Using the precision lift adjust the height of the specimen so that the desired target region is aligned with the instruments sensitive volume. Target regions can be chosen based on SEM cross sections. Program the syringe pump to deliver 1.00 mL/min±0.01 mL for 1.00 min for PIF test fluid or 5.00 mL/min±0.01 mL for 1.00 min for 0.9% Saline test fluid. Start the measurement and collect NMR Amplitude (a.u.) for 50 experiments before initiating fluid flow to provide a signal baseline. Position the outlet tube from the syringe pump over the center of the specimen and move during applying liquid over the total sample surface, but do not touch the borders of the sample. Trigger the system to continue collection of NMR amplitude data while simultaneously initiating fluid flow for 1 mL over 60 sec. At 300 sec after the trigger, add 0.50 mL of test fluid at approximately 0.5 mL/sec to the center of the specimen via a calibrated Eppendorf pipet. Utilizing the generated NMR Amplitude versus time graph following the second insult that is the 'gush dose' the % change in signal Amplitude versus time can be determined as well as the time required to reduce the Amplitude signal from its peak following the 'gush dose' by for example 20%, 30%, 50%, 75% or 100% can be determined. Reduction of signal amplitude occurs as fluid is absorbed and distributed beyond preset NMR viewing range.

The third measurement is a 1-D Wet Distribution Profile. Immediately after the Kinetic measurement is complete, replace the cap on the specimen. The Wet Distribution is run under the same experimental conditions as the previous Dry Distribution, described above.

Calibration of the NMR Amplitude for the Kinetic signal can be performed by filling glass vials (8 mm outer diameter and a defined inner diameter by at least 50 mm tall) with the appropriate fluid. Set the instrument conditions as described for the kinetics experiment. A calibration curve is constructed by placing an increasing number of vials onto the instrument (vials should be distributed equally over the 40 mm×40 mm measurement region) and perform the kinetic measurements. The volumes are calculated as the summed cross sectional area of the vials present multiplied by the z-resolution where Resolution (mm) is calculated as 1/Acquisition Time (s) divided by the instruments Gradient Strength (Hz/mm). The Calibration of the NMR Amplitude for the Distribution Profile is performed as an internal calibration based on the dry and wet profiles. In this procedure, the area beneath wet and dry profile were calculated and after subtracting them the total area (excluding markers) was obtained. This total area is correlated to the amount of applied liquid (here 1.5 mL). The liquid amount (μL) per 100 μm step can then be calculated. From the 1-D Wet Distribution Profile calculate the volume in the top 0.5 mm of the sample and report as microliter to the nearest 0.1 microliter.

Free Fluid Acquisition

Artificial menstrual fluid (AMF), prepared as described herein, is dosed onto the surface of an article. All measurements are performed at constant temperature (23° C.±2 C°) and relative humidity (50%±2%).

Absorbent article samples are conditioned at 23° C.±2 C° and 50%±2% relative humidity for 2 hours prior to testing. Place a sample article flat, with the top sheet of the product facing upward. Position the tip of a mechanical pipette about 1 cm above the center (longitudinal and lateral midpoint) of the article's absorbent core, and accurately pipette 1.00 mL±0.05 mL of AMF onto the surface. The fluid is dispensed without splashing, within a period of 2 seconds. As soon as the fluid makes contact with the test sample, start a timer accurate to 0.01 seconds. After the fluid has been acquired (no pool of fluid left on the surface), stop the timer and record the Acquisition Time to the nearest 0.01 second. Wait 2 minutes. In like fashion, a second and third dose of AMF are applied to the test sample and the acquisition times are recorded to the nearest 0.01 second.

This entire procedure is repeated on five substantially similar replicate articles. The reported value is the average of the five individual recorded measurements for Free Fluid Acquisition Time (first, second and third) to the nearest 0.01 second.

Overlap Distance Test

A Scanning Electron Microscope (SEM) is used to obtain an image of the cross-section of an absorbent article where an intentional depression has been made. From this image, the amount of overlap of fiber masses directly adjacent to the depression is measured. All measurements are performed in a laboratory maintained at 23° C.±2 C° and 50%±2% relative humidity and test specimens are conditioned in this environment for at least 2 hours prior to testing.

Obtain a test specimen by excising the layer(s) of interest from an absorbent article, if necessary. When excising an individual layer (or layers), use care to not impart any contamination or distortion to the test region during the process. The test region contains the area where an intentional depression has been made. A razor blade (such as VWR Single Edge Industrial, 0.009" thick surgical carbon steel available from VWR Scientific, Radnor, PA, USA, or equivalent) is used to section the test specimen. Using the razor blade, a cut is made along the lateral axis of a depression at its longitudinal midpoint so that a cross-section of the depression can be imaged. The test specimen is then adhered to a mount using double-sided Cu tape, with the cross-section face up, and sputter AU coated.

Secondary Electron (SE) images of the cross-sectioned test specimen are obtained using an SEM (such as FEI Quanta 450 available from FEI Company, Hillsboro, OR, USA, or equivalent), operated in high-vacuum mode using acceleration voltages between 3 and 5 kV and a working distance of approximately 12-18 mm. This methodology assumes the analyst is skilled in SEM operation so that images are obtained with sufficient contrast for analysis. The instrument is calibrated according to the manufacturer's specifications prior to use to ensure an accurate distance scale.

The test specimen is viewed at a magnification that enables clear visualization of the full depth of the depression along with the fiber masses on each side of the depression, and an image is acquired. The image is then analyzed to determine the overlap of the fiber masses. Referring back to FIG. 15C, first draw a Center Line 1507 on the image that runs parallel to the z-direction (thickness) of the test specimen and intersects the center of the depression (e.g. where the fiber masses meet). Draw a Base Line 1509 on the image that runs parallel to the x-y direction of the test specimen at the base of the depression. Along the contour of the fiber mass along its edge nearest the depression, determine where the fiber mass edge reaches the Base Line and mark as "OD" (line 1505). Measure the distance 1503 between the Center Line and location "OD" to the nearest 0.01 mm and record as Overlap Distance. In like fashion, repeat for a total of 5 replicates. Calculate the arithmetic mean for Overlap Distance and report to the nearest 0.01 mm.

Surface Energy/Contact Angle Method

Contact angles on substrates are determined using ASTM D7490-13 modified with the specifics as describe herein, using a goniometer and appropriate image analysis software (a suitable instrument is the FTA200, First Ten Angstroms, Portsmouth, VA, or equivalent) fitted with a 1 mL capacity, gas tight syringe with a No. 27 blunt tipped stainless steel needle. Two test fluids are used: Type II reagent water (distilled) in accordance with ASTM Specification D1193-99 and 99+% purity diiodomethane (both available from Sigma Aldrich, St. Louis, MO). Contact angles from these two test fluids can further be used to calculate surface energy based on the Owens-Wendt-Kaelble equation. All testing is to be performed at about 23° C.±2 C° and a relative humidity of about 50%±2%.

Set up the goniometer on a vibration-isolation table and level the stage according to the manufacturer's instructions. The video capture device must have an acquisition speed capable of capturing at least 10-20 images from the time the drop hits the surface of the specimen to the time it cannot be resolved from the specimen's surface. A capture rate of 900 images/sec is typical. Depending on the hydrophobicity/hydrophilicity of the specimen, the drop may or may not rapidly wet the surface of the nonwoven sample. In the case of slow acquisition, the images should be acquired until 2% of the volume of the drop is absorbed into the specimen. If the acquisition is extremely fast, the first resolved image should be used if the second image shows more than 2% volume loss.

Place the specimen on the goniometer's stage and adjust the hypodermic needle to the distance from the surface recommended by the instrument's manufacturer (typically 3 mm). If necessary, adjust the position of the specimen to place the target site under the needle tip. Focus the video device such that a sharp image of the drop on the surface of the specimen can be captured. Start the image acquisition. Deposit a 5 µL±0.1 µL drop onto the specimen. If there is visible distortion of the drop shape due to movement, repeat at a different, but equivalent, target location. Make two angle measurements on the drop (one on each drop edge) from the image at which there is a 2% drop volume loss. If the contact angles on two edges are different by more than 4°, the values should be excluded and the test repeated at an equivalent location on the specimen. Identify five additional equivalent sites on the specimen and repeat for a total of 6 measurements (12 angles). Calculate the arithmetic mean for this side of the specimen and report to the nearest. 0.01°. In like fashion, measure the contact angle on the opposite side of the specimen for 6 drops (12 angles) and report separately to the nearest 0.01°.

To calculate surface energy, the contact angle for both water and diiodomethane must be tested as described above. The value for each test fluid is then substituted into two separate expressions of the Owens-Wendt-Kaelble equation (one for each fluid). This results in two equations and two unknowns, which are then solved for the dispersion and polar components of surface tension.

The Owens-Wendt-Kaelble equation:

$$\frac{\gamma_l(1+\cos\theta)}{2} + (\gamma_l^d + \gamma_s^d)^{0.5} + (\gamma_l^p + \gamma_s^p)^{0.5}$$

where:

θ=the average contact angle for the test liquid on the test specimen $\gamma_l$ and $\gamma_s$=the surface tension of the test liquid and test specimen, respectively, in dyn/cm $\gamma^d$ and $\gamma^p$=the dispersion and polar components of the surface tension, respectively, in dyn/cm

|  | Surface Tension ($\gamma_l$) (dyn/cm) | | |
| --- | --- | --- | --- |
| Solvent | Dispersion | Polar | Total |
| Diiodomethane | 50.8 | 0.0 | 50.8 |
| Water | 21.8 | 51.0 | 72.8 |

The Owens-Wendt-Kaelble equation is simplified to the following when a dispersive solvent such as diiodomethane is used since the polar component is zero:

$$\frac{\gamma_l(1+\cos\theta)}{2} + \left(\gamma_l^d + \gamma_s^d\right)^{0.5}$$

Using the values from the table and θ (measured) for diiodomethane, the equation can be solved for the dispersive component of surface energy ($\gamma_s^d$). Now using the values from the table and θ (measured) for water, and the calculated value ($\gamma_s^d$), the Owens-Wendt-Kaelble equation can be solved for the polar component of surface energy ($\gamma_s^p$). The sum of $\gamma_s^d + \gamma_s^p$ is the total solid surface tension and is reported to the nearest 0.1 dyn/cm.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

The invention claimed is:

1. A disposable absorbent article having a longitudinal centerline and a lateral centerline, the disposable absorbent article further comprising:
    a topsheet;
    a backsheet;
    an absorbent core comprising a plurality of absorbent fibers disposed between the topsheet and the backsheet; and
    a first plurality of conforming features in at least the absorbent core or a combination of the absorbent core and the topsheet, wherein the conforming features do not extend through the absorbent core, wherein the disposable absorbent article has blot residual value of less than 30 mg and a bending stiffness of less than 12, wherein the conforming features do not include embossing features.

2. The disposable absorbent article of claim 1, wherein the absorbent article has a blot residual to caliper ratio of less than 11.

3. The disposable absorbent article of claim 1, wherein the absorbent article has a stiffness to caliper ratio of 4 or less.

4. The disposable absorbent article of claim 1, wherein the first plurality of conforming features is comprised by the combination of at least the absorbent core and the topsheet.

5. The disposable absorbent article of claim 4, wherein the absorbent core is unitary airlaid absorbent core comprising a plurality of cellulosic fibers and super absorbent particles, and wherein a ratio of bending stiffness to wet recovery energy is less than 13.

6. The disposable absorbent article of claim 4, wherein the conforming features are further comprised by a fluid management layer disposed between the topsheet and the absorbent core, wherein the fluid management layer comprises an airlaid material comprising a plurality of cellulosic fibers, wherein the absorbent article has a ratio of bending stiffness to wet recovery energy that is less than 15 as measured by the three point bending test and the bunch compression test as described herein.

7. The disposable absorbent article of claim 4, wherein the absorbent article comprises a coformed absorbent core comprising continuous fibers and wherein the absorbent article has a ratio of bending stiffness to wet recovery energy that is less than 4 as measured by the three point bending test and the bunch compression test as described herein.

8. The disposable absorbent article of claim 4, wherein the absorbent article has a blot to caliper ratio of less than 11.

9. The disposable absorbent article of claim 4, wherein the absorbent article has a blot to caliper ratio of less than 19, and wherein the absorbent core comprises an airlaid absorbent core.

10. The disposable absorbent article of claim 4, wherein the absorbent core is a unitary airlaid absorbent core comprising a plurality of cellulosic fibers and super absorbent particles, and wherein a ratio of bending stiffness to caliper is less than 15.

11. The disposable absorbent article of claim 4, wherein the conforming features are further comprised by a fluid management layer disposed between the topsheet and the absorbent core, wherein the fluid management layer comprises an airlaid material comprising a plurality of cellulosic fibers, wherein the disposable absorbent article has a ratio of bending stiffness to caliper of less than 5.

12. The disposable absorbent article of claim 4, wherein the absorbent core is a coformed absorbent core comprising continuous fibers, and wherein the absorbent article has a ratio of bending stiffness to caliper of 4 or less.

13. The disposable absorbent article of claim 1, wherein the absorbent core is a unitary airlaid absorbent core comprising a plurality of cellulosic fibers and super absorbent particles, and wherein the disposable absorbent article has a residual fluid in the top 0.5 mm of a total caliper of the disposable absorbent article of less than 200 µl.

14. The disposable absorbent article of claim 1, further comprising a fluid management layer disposed between the topsheet and the absorbent core, wherein the fluid management layer is an airlaid material comprising a plurality of cellulose fibers, wherein the disposable absorbent article has a residual fluid in the top 0.5 mm of a total caliper of the disposable absorbent article of less than 20 µl.

15. The disposable absorbent article of claim 1, wherein the absorbent core is a coformed absorbent core comprising continuous fibers, and wherein the absorbent article has a residual fluid in the top 0.5 mm of a total caliper of the disposable absorbent article of less than 7 µl and a free fluid acquisition time of less than 100 seconds.

16. The disposable absorbent article of claim 1, wherein the absorbent article has a wet recovery energy of at least 0.4 mJ, as measured by the bunch compression test described herein.

17. The disposable absorbent article of claim 1, wherein the absorbent core is a unitary airlaid absorbent core comprising a plurality of cellulosic fibers and super absorbent particles, and wherein the disposable absorbent article has a free fluid acquisition time of less than 60 seconds as measured by the free fluid acquisition test.

18. The disposable absorbent article of claim 1, further comprising a fluid management layer disposed between the topsheet and the absorbent core, wherein the fluid management layer is an airlaid material comprising a plurality of cellulose fibers, and wherein the absorbent article has a residual fluid in the top 0.5 mm of a total caliper of the disposable absorbent article of less than 20 µl and a free fluid acquisition time of less than 40 seconds.

19. The disposable absorbent article of claim 1, wherein the average length of the long fibers is greater than about 6 mm.

20. A disposable absorbent article having a longitudinal centerline and a lateral centerline, the disposable absorbent article further comprising:
   a topsheet;
   a backsheet;
   an absorbent core comprising a plurality of absorbent fibers disposed between the topsheet and the backsheet; and
   a first plurality of conforming features in at least the absorbent core or a combination of the absorbent core and the topsheet, wherein the disposable absorbent article has blot residual value of less than 30 mg and a bending stiffness of less than 12, wherein the conforming features do not include embossing features.

* * * * *